US012788398B2

(12) United States Patent
Batty et al.

(10) Patent No.: US 12,788,398 B2
(45) Date of Patent: Nov. 10, 2026

(54) ROBOTIC STAPLING AND CUTTING SYSTEMS AND METHODS

(71) Applicant: CILAG GMBH INTERNATIONAL, Zug (CH)

(72) Inventors: Christopher Batty, Cincinnati, OH (US); Robert Jason Simms, Cincinnati, OH (US); Jonathan Von Stein, Cincinnati, OH (US); Maria Lupp, Cincinnati, OH (US); Jason C. Bryant, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/775,545

(22) Filed: Jul. 17, 2024

(65) Prior Publication Data

US 2025/0025169 A1 Jan. 23, 2025

Related U.S. Application Data

(60) Provisional application No. 63/515,001, filed on Jul. 21, 2023, provisional application No. 63/514,972,
(Continued)

(51) Int. Cl.
*A61B 17/072* (2006.01)
*A61B 17/064* (2006.01)
(Continued)

(52) U.S. Cl.
CPC ........ *A61B 17/072* (2013.01); *A61B 17/0643* (2013.01); *A61B 17/07207* (2013.01); *A61B 34/30* (2016.02); *A61B 2017/00017* (2013.01); *A61B 2017/00367* (2013.01); *A61B 2017/00398* (2013.01); *A61B 2017/00411* (2013.01); *A61B 2017/00477* (2013.01); *A61B 2017/00831* (2013.01); *A61B 2017/00862* (2013.01); *A61B 17/068* (2013.01); *A61B 17/0686* (2013.01); *A61B 2017/07257* (2013.01);
(Continued)

(58) Field of Classification Search
CPC .......... A61B 17/07207; A61B 17/0643; A61B 34/30
See application file for complete search history.

(56) References Cited

U.S. PATENT DOCUMENTS

| | | | |
|---|---|---|---|
| 8,292,150 | B2 | 10/2012 | Bryant |
| 8,460,275 | B2 | 6/2013 | Taylor et al. |

(Continued)

FOREIGN PATENT DOCUMENTS

| | | | |
|---|---|---|---|
| EP | 2768418 | B1 | 7/2017 |
| EP | 2811932 | B1 | 6/2019 |

(Continued)

*Primary Examiner* — Nathaniel C Chukwurah
(74) *Attorney, Agent, or Firm* — Troutman Pepper Locke LLP

(57) ABSTRACT

Systems and subsystems for cutting and stapling tissue are disclosed. More specifically, the present disclosure relates to systems, devices, and subsystems for attachments for robotic surgeries. The surgical instrument is a robotic attachment. The surgical instrument includes a closure subsystem, an articulation subsystem, a roll subsystem, and a transection subsystem that are operable independently of each other.

20 Claims, 70 Drawing Sheets

Related U.S. Application Data filed on Jul. 21, 2023, provisional application No. 63/634,171, filed on Apr. 15, 2024, provisional application No. 63/634,201, filed on Apr. 15, 2024.

(51) Int. Cl.

| | |
|---|---|
| ***A61B 34/30*** | (2016.01) |
| *A61B 17/00* | (2006.01) |
| *A61B 17/068* | (2006.01) |
| *A61B 17/29* | (2006.01) |

(52) U.S. Cl.

CPC ............... *A61B 2017/07271* (2013.01); *A61B 2017/07285* (2013.01); *A61B 2017/2903* (2013.01); *A61B 2217/007* (2013.01)

(56) References Cited

U.S. PATENT DOCUMENTS

| | | | |
|---|---|---|---|
| 8,800,838 | B2 | 8/2014 | Shelton, IV et al. |
| 9,232,979 | B2 | 1/2016 | Parihar et al. |
| 10,085,748 | B2 | 10/2018 | Morgan et al. |
| 10,143,524 | B2 | 12/2018 | Koch |
| 10,251,716 | B2 | 4/2019 | Overmyer |
| 10,307,215 | B2 | 6/2019 | Swayze |
| 10,327,854 | B2 | 6/2019 | Overmyer |
| 10,376,276 | B2 | 8/2019 | Overmyer |
| 10,433,920 | B2 | 10/2019 | Overmyer |
| 10,542,982 | B2 | 1/2020 | Beckman |
| 10,675,025 | B2 | 6/2020 | Swayze |
| 10,702,349 | B2 | 7/2020 | Overmyer |
| 10,918,385 | B2 | 2/2021 | Overmyer |
| 10,987,177 | B2 | 4/2021 | Overmyer et al. |
| 11,033,344 | B2 | 6/2021 | Overmyer |
| 11,058,477 | B2 | 7/2021 | Messerly et al. |
| 11,141,150 | B2 | 10/2021 | Shelton, IV et al. |
| 11,191,539 | B2 | 12/2021 | Overmyer |
| 11,191,543 | B2 | 12/2021 | Overmyer |
| 11,191,560 | B2 | 12/2021 | Overmyer |
| 11,419,605 | B2 | 8/2022 | Denzinger |
| 11,419,606 | B2 | 8/2022 | Overmyer |
| 11,439,474 | B2 | 9/2022 | Kallenberger |
| 11,446,098 | B2 | 9/2022 | Swayze |
| 11,471,228 | B2 | 10/2022 | Overmyer |
| 11,547,494 | B2 | 1/2023 | Swayze |
| 11,559,366 | B2 | 1/2023 | Overmyer |
| 11,622,825 | B2 | 4/2023 | Overmyer |
| 11,813,032 | B2 | 11/2023 | Overmyer |
| 11,813,746 | B2 | 11/2023 | Overmyer |
| 11,864,954 | B2 | 1/2024 | Overmyer |
| 12,023,116 | B2 | 7/2024 | Overmyer |
| 12,070,287 | B2 | 8/2024 | Overmyer |
| 2003/0130677 | A1 | 7/2003 | Whitman et al. |
| 2007/0023476 | A1 | 2/2007 | Whitman et al. |
| 2009/0114699 | A1 | 5/2009 | Viola |
| 2014/0263541 | A1 | 9/2014 | Leimbach et al. |
| 2014/0303645 | A1 | 10/2014 | Morgan et al. |
| 2016/0067001 | A1 | 3/2016 | Parihar et al. |
| 2016/0174976 | A1 | 6/2016 | Morgan et al. |
| 2016/0174978 | A1 | 6/2016 | Overmyer et al. |
| 2016/0213438 | A1 | 7/2016 | Jogasaki et al. |
| 2019/0021752 | A1 | 1/2019 | Boudreaux et al. |
| 2019/0105117 | A1 | 4/2019 | Brisson et al. |
| 2019/0183491 | A1* | 6/2019 | Shelton, IV ........... A61B 34/30 |
| 2019/0183504 | A1 | 6/2019 | Shelton, IV et al. |
| 2019/0183592 | A1* | 6/2019 | Shelton, IV ........... A61B 34/37 |
| 2019/0183597 | A1* | 6/2019 | Shelton, IV ..... A61B 17/07207 |
| 2020/0093489 | A1 | 3/2020 | Parihar et al. |
| 2020/0330120 | A1* | 10/2020 | Koch, Jr. ........ A61B 17/320016 |
| 2020/0375596 | A1 | 12/2020 | Corsetto |
| 2020/0375674 | A1 | 12/2020 | Overmyer et al. |
| 2021/0059664 | A1 | 3/2021 | Hensel et al. |
| 2021/0059773 | A1 | 3/2021 | Overmyer et al. |
| 2021/0059777 | A1* | 3/2021 | Overmyer .............. A61B 34/71 |
| 2021/0346050 | A1 | 11/2021 | Boudreaux et al. |
| 2022/0031321 | A1 | 2/2022 | Sun et al. |
| 2022/0105638 | A1 | 4/2022 | Zhang et al. |
| 2022/0105639 | A1 | 4/2022 | Zhang et al. |
| 2022/0125538 | A1 | 4/2022 | Overmyer et al. |
| 2022/0192707 | A1 | 6/2022 | Barakat et al. |
| 2022/0346897 | A1 | 11/2022 | Black et al. |
| 2022/0409310 | A1 | 12/2022 | Overmyer et al. |
| 2023/0001579 | A1 | 1/2023 | Overmyer |
| 2023/0181275 | A1 | 6/2023 | Overmyer |
| 2023/0338051 | A1 | 10/2023 | Koch, Jr. |
| 2023/0355338 | A1 | 11/2023 | Overmyer |
| 2024/0081191 | A1 | 3/2024 | Beckman |
| 2024/0271574 | A1 | 8/2024 | Hill et al. |

FOREIGN PATENT DOCUMENTS

| | | | |
|---|---|---|---|
| EP | 2866697 | B1 | 12/2021 |
| KR | 20150100137 | A | 9/2015 |
| WO | 2020212875 | A1 | 10/2020 |
| WO | 2021038360 | A2 | 3/2021 |
| WO | 2022144818 | A1 | 7/2022 |
| WO | 2023225866 | A1 | 11/2023 |
| WO | 2024224333 | A2 | 10/2024 |

* cited by examiner

ROBOTIC STAPLING AND CUTTING SYSTEMS AND METHODS

CROSS-REFERENCE TO RELATED APPLICATIONS

The present application claims the benefit of, and priority to, U.S. Provisional Application Ser. No. 63/514,972 filed on Jul. 21, 2023, U.S. Provisional Application Ser. No. 63/515,001 filed on Jul. 21, 2023, U.S. Provisional Application Ser. No. 63/634,201 filed on Apr. 15, 2024, and U.S. Provisional Application Ser. No. 63/634,171 filed on Apr. 15, 2024, the disclosures of which are expressly incorporated herein by reference.

FIELD OF INVENTION

The present disclosure generally relates to systems, devices, and subsystems for cutting and stapling tissue. More specifically, the present disclosure relates to systems, devices, and subsystems for attachments for robotic surgeries.

BACKGROUND

Stapling is a crucial aspect of many surgical procedures, such as gastrointestinal, thoracic, and gynecological surgeries. Robotic surgical systems have gained significant recognition in recent years due to their potential to enhance surgical precision and dexterity. However, the development of a dedicated surgical stapling instrument that integrates seamlessly into the surgical workflow of a multi-purpose robot remains an unmet need for many surgeons.

SUMMARY

It is an object of the present designs to provide devices and methods to meet the above-stated needs. The designs can be for systems, devices, and subsystems for stapling attachments for robotic surgeries. The attachments can have several subsystems that can be independently actuated to provide a specific action, such as closing of an end effector of the stapler, articulation of the end effector, rolling of the end effector, and firing of the staples within the end effector.

In one example, the surgical instrument described herein includes an articulation subsystem for a surgical instrument. The articulation subsystem comprises a rotatable shaft having a longitudinal axis and a distal channel retainer coupled to an end effector, the distal channel retainer being pivotable about an articulation pivot point. The articulation subsystem further comprises an articulation bushing slidable between a proximal position and a distal position along the longitudinal axis of the rotatable shaft and an articulation rod extending distally from the articulation bushing and coupled at a distal end to the distal channel retainer. The articulation subsystem further comprises a rack movable with respect to the longitudinal axis of the rotatable shaft, wherein movement of the rack with respect to the longitudinal axis imparts an axial force onto the articulation bushing moving the articulation bushing between the proximal position and the distal position. Furthermore, movement of the articulation bushing between the distal position and the proximal position actuates the articulation rod causing the distal channel retainer to pivot about the articulation pivot point.

The disclosed technology includes a closure subsystem for a surgical instrument comprising a first closure input puck engageable with a first closure robotic output, a cam gear rotatably engaged with the first closure input puck, and a yoke pin coupled to a closure tube and movable from a first position to a second position in response to a rotation of the cam gear. Movement of the yoke pin from the first position to the second position translates the closure tube distally onto an anvil ramp of an anvil.

The disclosed technology includes a roll subsystem for a surgical instrument comprising a rotatable shaft having a longitudinal axis, a first roll input puck engageable with a roll robotic output, a worm gear coupled to and rotatable by the first roll input puck, and a worm follower coupled to the rotatable shaft. Rotation of the first roll input puck causes the worm gear to rotate the worm follower and thereby roll the rotatable shaft about its longitudinal axis.

The disclosed technology includes a transection subsystem for a surgical instrument comprising a rotatable shaft having a lumen, a firing rod extending at least partially through the lumen, and a firing rack coupled to a proximal end of the firing rod. The firing rod is rotationally independent of the firing rack. The transection subsystem further includes a firing gear engaged with the firing rack. Rotation of the firing gear can move the firing rack and the firing rod axially.

The disclosed technology further includes a method comprising attaching a surgical instrument to a robotic arm, rotating a first input puck and a second input puck of the robotic arm until a predetermined threshold indicator on both the first input puck and the second input puck is detected. The first input puck and the second input puck can be in mechanical communication with an articulation subsystem of the surgical instrument. The method can further include rotating the first input puck and the second input puck to a predetermined articulation home position.

The disclosed technology further includes a housing for a surgical instrument configured to engage with a robotic arm. The housing includes a first opening positioned to be engaged with at least a portion of a robotic arm, a second opening positioned proximate a rod extending from within the housing, and a fluid management system positioned within the housing proximate one of the first opening or the second opening. The fluid management system can be configured to hold or divert fluid within the housing.

The disclosed technology includes a surgical instrument comprising a housing, a closure subsystem engaged with a shaft, an articulation subsystem movable along the shaft and independently of the closure subsystem, and a fluid management system positioned between the closure subsystem and the articulation subsystem and in contact with the shaft.

The disclosed technology includes an articulation subsystem for a surgical instrument comprising a rotatable shaft having a longitudinal axis, an articulation rod extending along the longitudinal axis of the rotatable shaft and rotationally coupled to the rotatable shaft, and a first articulation bushing slidable from a first position to a second position along the longitudinal axis of the rotatable shaft. The first articulation bushing can be rotationally coupled to the rotatable shaft. The articulation subsystem can further include a first rack movable with respect to the longitudinal axis of the rotatable shaft with the first rack being rotationally independent of the rotatable shaft and the first articulation bushing. The articulation subsystem can further include a first rack gear engaged with the first rack. Rotation of the first rack gear can move the first rack with respect to the longitudinal axis and movement of the first rack with respect to the longitudinal axis can impart an axial force onto the first articulation bushing moving the first articulation bushing from the first position to the second position.

The disclosed technology can include a closure subsystem comprising a cam gear comprising a cam track, and a yoke pin coupled to a closure tube and movable from a first position to a second position in response to a rotation of the cam gear. The yoke pin can extend into the cam track and the cam track can be shaped to provide a non-linear movement profile of the yoke pin and comprises an open position, a high speed compression region, a high force region, and a constant force region. The high speed compression region, the high force region, and the constant force region can each have different curvatures and the constant force region can be shaped such that the yoke pin remains stationary when tracking through the constant force region as the cam gear rotates.

Other aspects of the present disclosure will become apparent upon reviewing the following detailed description in conjunction with the accompanying figures. Additional features or manufacturing and use steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

FIG. 9 is a perspective view of the surgical instrument while

FIG. 19A is a perspective view of the components of the roll subsystem, and FIG. 19B is a top, cross-sectional view of the components of the roll subsystem, according to aspects of the present disclosure.

FIG. 19C shows an example of a shaft with two flat sections (or "flats"), FIG. 19D shows an example of a shaft with a keyway and a worm follower with a corresponding key feature, FIG. 19E shows an example of a shaft with a keyway and a worm follower with a corresponding key feature, and FIG. 19F shows an example of a shaft and a worm follower with corresponding steps, according to aspects of the present disclosure.

FIG. 19G is a side cross sectional view thereof, and FIG. 19H is cross sectional view from the direction indicated in 19G, according to aspects of the present disclosure.

FIG. 22A shows the transection subsystem in home position, FIG. 22B shows the transection subsystem in a first firing position, and FIG. 22C shows the transection subsystem in a second firing position.

FIG. 24A shows a manual knife return key inside the compartment, FIG. 24B shows the manual knife return key removed from the compartment, and FIG. 24C shows the closure key attached to a retract key receiver.

FIG. 27A shows fluid management cavities surrounded by walls.

FIG. 27R shows a cross sectional view of the positioning of the seal extension, according to aspects of the present disclosure.

DETAILED DESCRIPTION

Specific examples of the present invention are now described in detail with reference to the Figures, where identical reference numbers indicate elements which are functionally similar or identical. The examples address many of the deficiencies associated with prior robotic attachment systems, for instance prior systems that did not provide integrated capabilities to close, articulate, roll, and fire, all with the actuation of their designated robotic outputs. The present surgical instrument includes a housing that contains the gearing and other components necessary to effect the close, articulate, roll, and fire features. In particular, the present disclosure provides a detailed discussion of the closure subsystem, articulation system, roll subsystem, and transection subsystem that are usable to close, articulate, roll, and fire an end effector of the device. Use of the term “fire” throughout this disclosure means to advance the distal portions of the transection subsystem distally. “Firing” the components shall be understood to mean cutting, stapling, or both.

Overview

Figure 1:
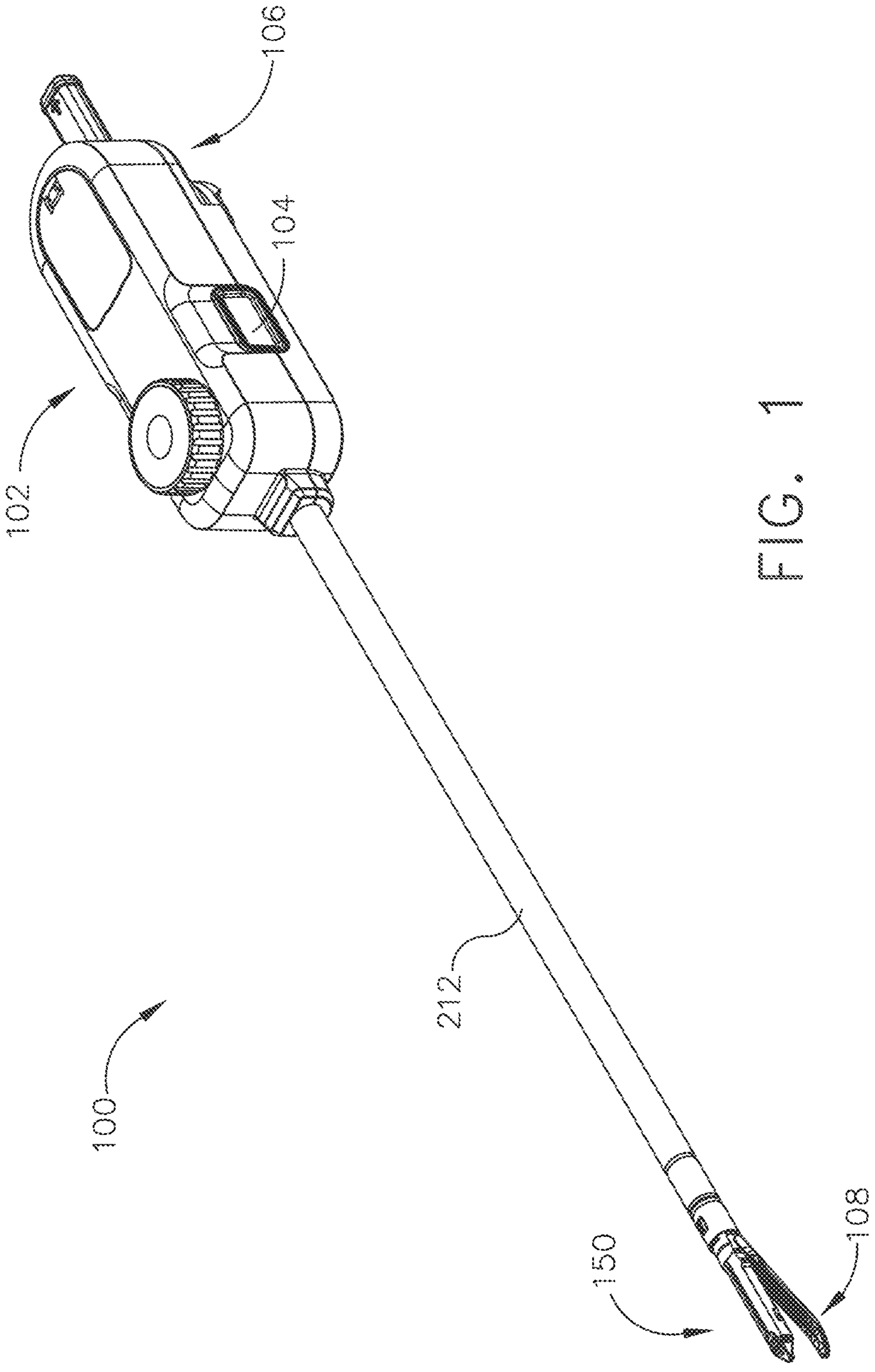
FIG. 1 shows a surgical instrument, according to aspects of the present disclosure.

Turning to the figures, FIG. 1 is a perspective view illustrating a surgical instrument 100, according to aspects of the present disclosure. A housing 102 of the surgical instrument 100 can be attachable to a robotic arm that includes a plurality of outputs, or rotatable disks, that can actuate pucks, or other disks, on the surgical instrument 100. The proximal end 106 of the surgical instrument 100 can be attached to a robotic arm and the distal end 108 of the surgical instrument 100 effects the transection and stapling of patient tissue. The proximal end 106 of the surgical instrument 100 includes a tail cover 114. The surgical instrument can include one or more release buttons 104 that allows the device to be detached from the robotic arm.

Figure 2A:
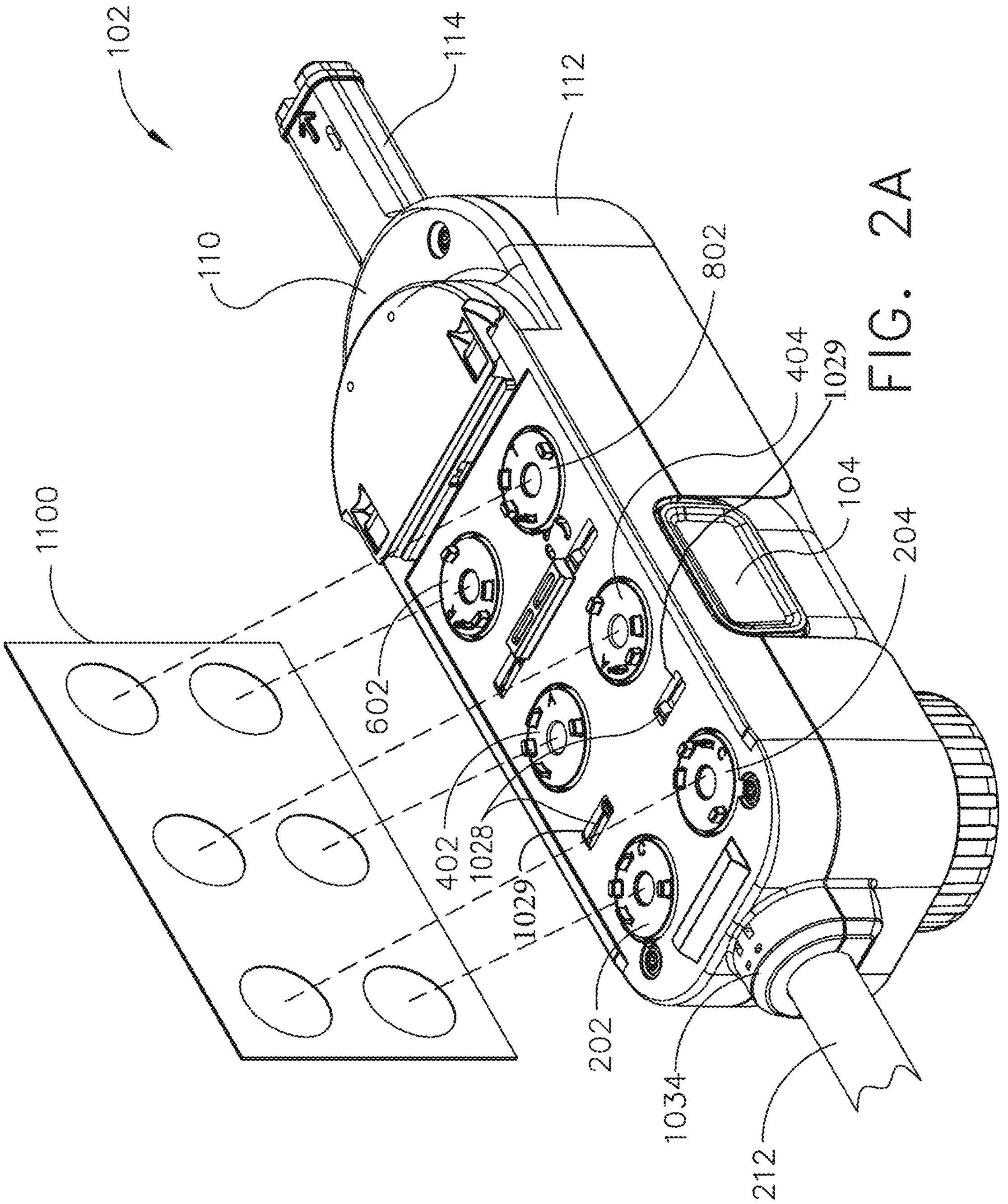
FIG. 2A shows a housing at a proximal end of a surgical instrument, according to aspects of the present disclosure.

FIG. 2A is a perspective view of the housing 102 as shown from the other side from what is shown in FIG. 1. The housing 102 can include a first portion 110 and a second portion 112. The housing 102 includes a series of pucks (e.g., first closure input puck 202, second closure input puck 204, first articulation input puck 402, second articulation input puck 404, roll input puck 602, and transection input puck 802). The pucks include features that enable them to engage with the rotating features of the robotic arm 1100 and a sterile adapter positioned between the surgical instrument 100 and the robotic arm 1100, such that rotation of the pucks can actuate the gears and other components of the closure subsystem 200, articulation subsystem 400, roll subsystem 600, and transection subsystem 800 described herein.

Figure 3A:
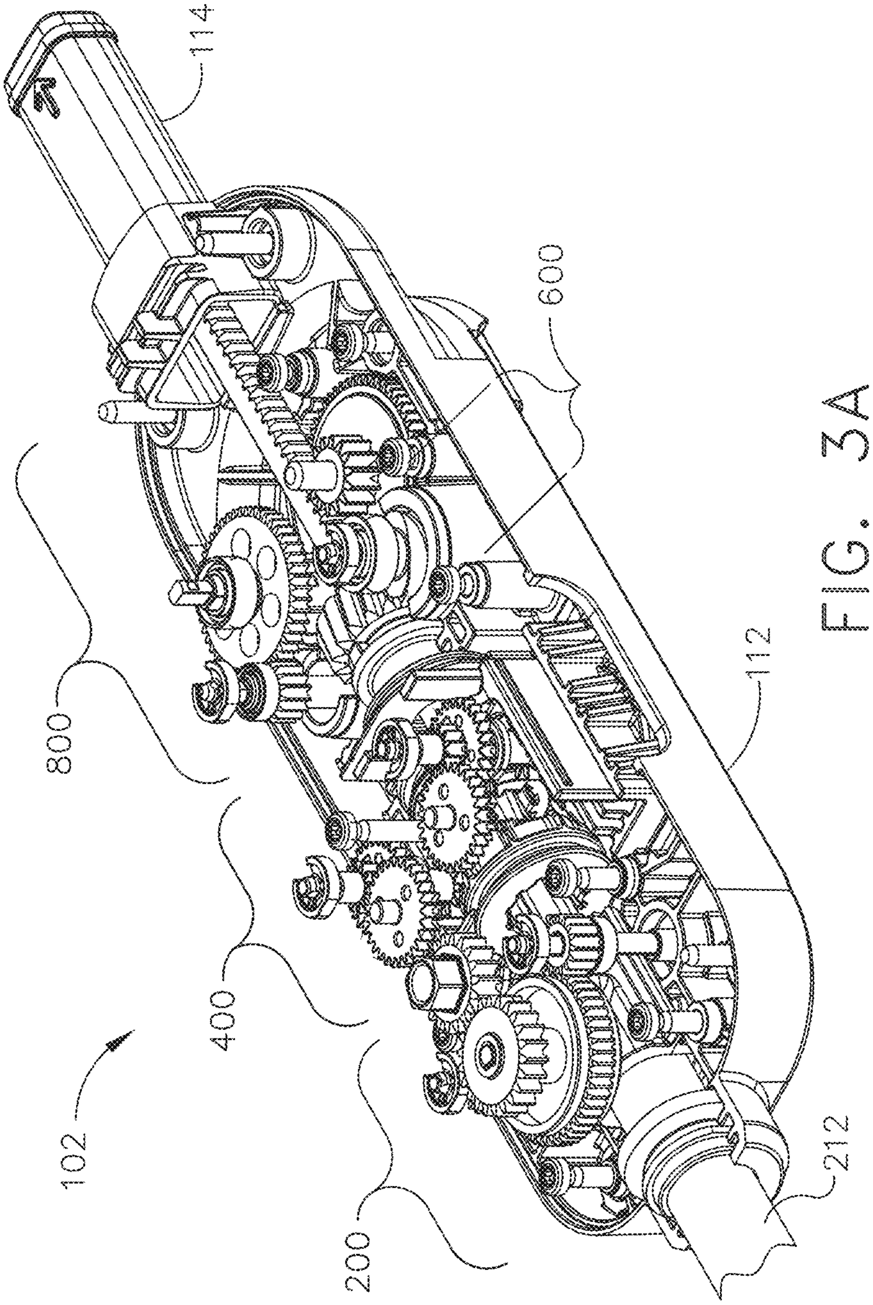
FIGS. 3A and 3B show internal components of a housing at a proximal end of a surgical instrument, according to aspects of the present disclosure.
Figure 3B:
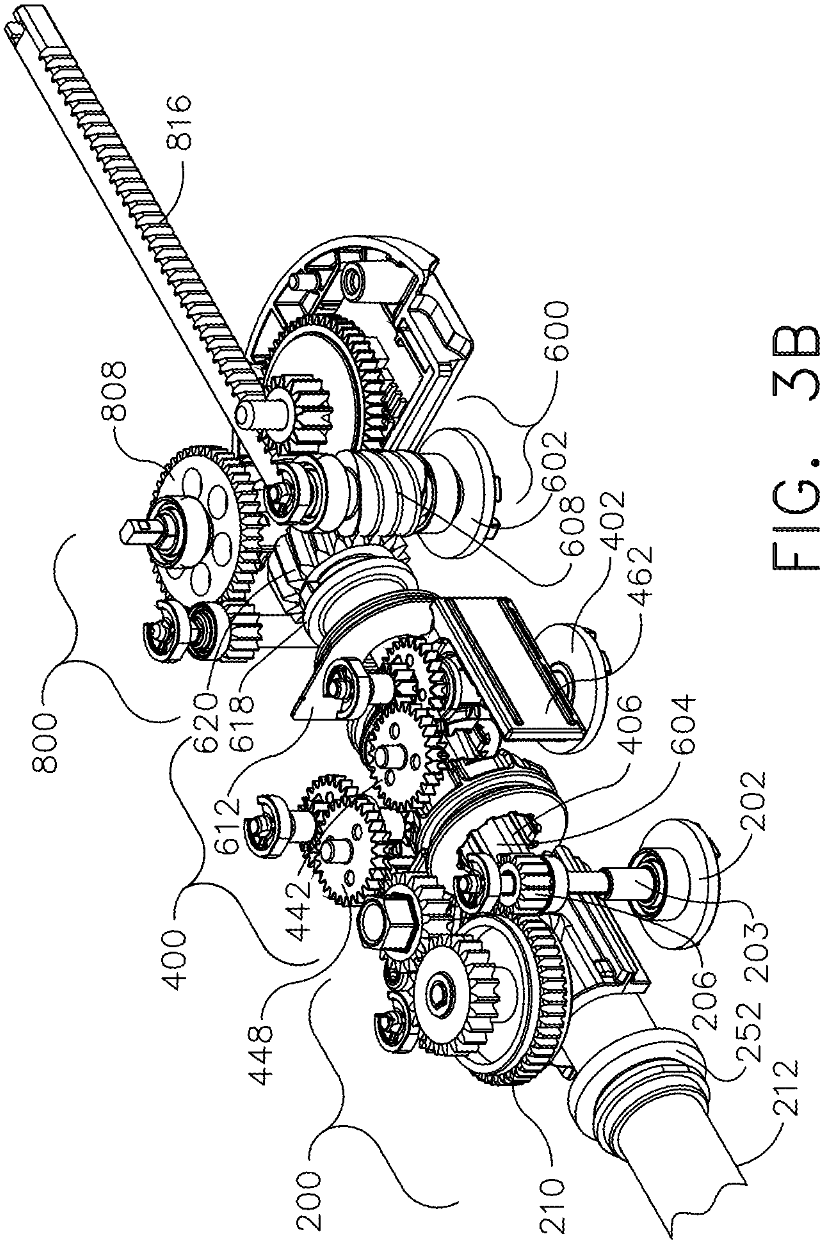

FIGS. 3A and 3B show internal components of the housing 102 at the proximal end 106 of the surgical instrument 100. As shown in FIG. 3A, housing 102 includes components of the closure subsystem 200, articulation subsystem 400, roll subsystem 600, and transection subsystem 800 described herein. As will be described in greater detail herein, the pucks (e.g., first closure input puck 202, second closure input puck 204, first articulation input puck 402, second articulation input puck 404, roll input puck 602, and transection input puck 802) can each be attached to components that extend through the housing 102 and rotationally engage respective components of the closure subsystem 200, articulation subsystem 400, roll subsystem 600, and transection subsystem 800. In this way, rotation of each individual puck causes the end effector to actuate (roll, close or open, articulate, fire staples, etc.) to enable physician to complete a surgery via a robotic system.

Figure 2B:
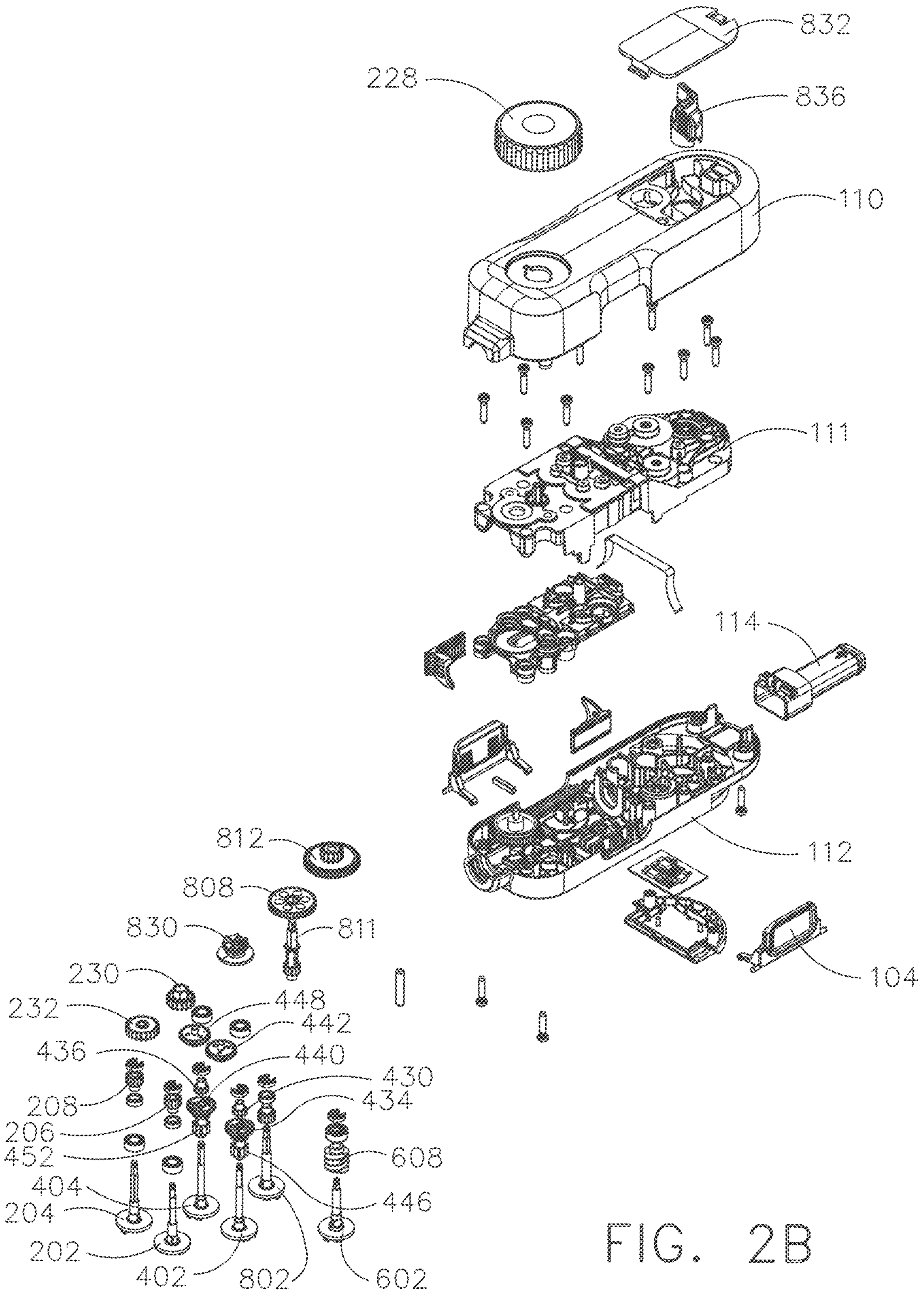
FIG. 2B is an exploded view of the components within a proximal end of a surgical instrument, according to aspects of the present disclosure.

FIG. 3B shows internal components of the surgical instrument 100 shown without an outer housing 102, according to aspects of the present disclosure. The closure subsystem 200 and the articulation subsystem 400 each utilize two different pucks (e.g., first closure input puck 202, second closure input puck 204, first articulation input puck 402, and second articulation input puck 404) for their respective actions, whereas the roll subsystem 600 and transection subsystem 800 each utilize only one puck (e.g., roll input puck 602 and transection input puck 802) for their respective actions. There are certain benefits to the closure subsystem 200 and the articulation subsystem 400 each utilizing two different pucks, including but not limited to providing additional force to increase the closure subsystem’s 200 ability to compress tissue and adding input torque and reducing lash to increase responsiveness for articulation. FIG. 2B is an exploded view of the components within a proximal end 106 of the surgical instrument 100. As shown in FIG. 2B, the outer housing 102 can further include an intermediate housing 111 that can be disposed between the first portion 110 and the second portion 112 and help to provide support to the various components in the outer housing 102 as described further herein.

Figure 4:
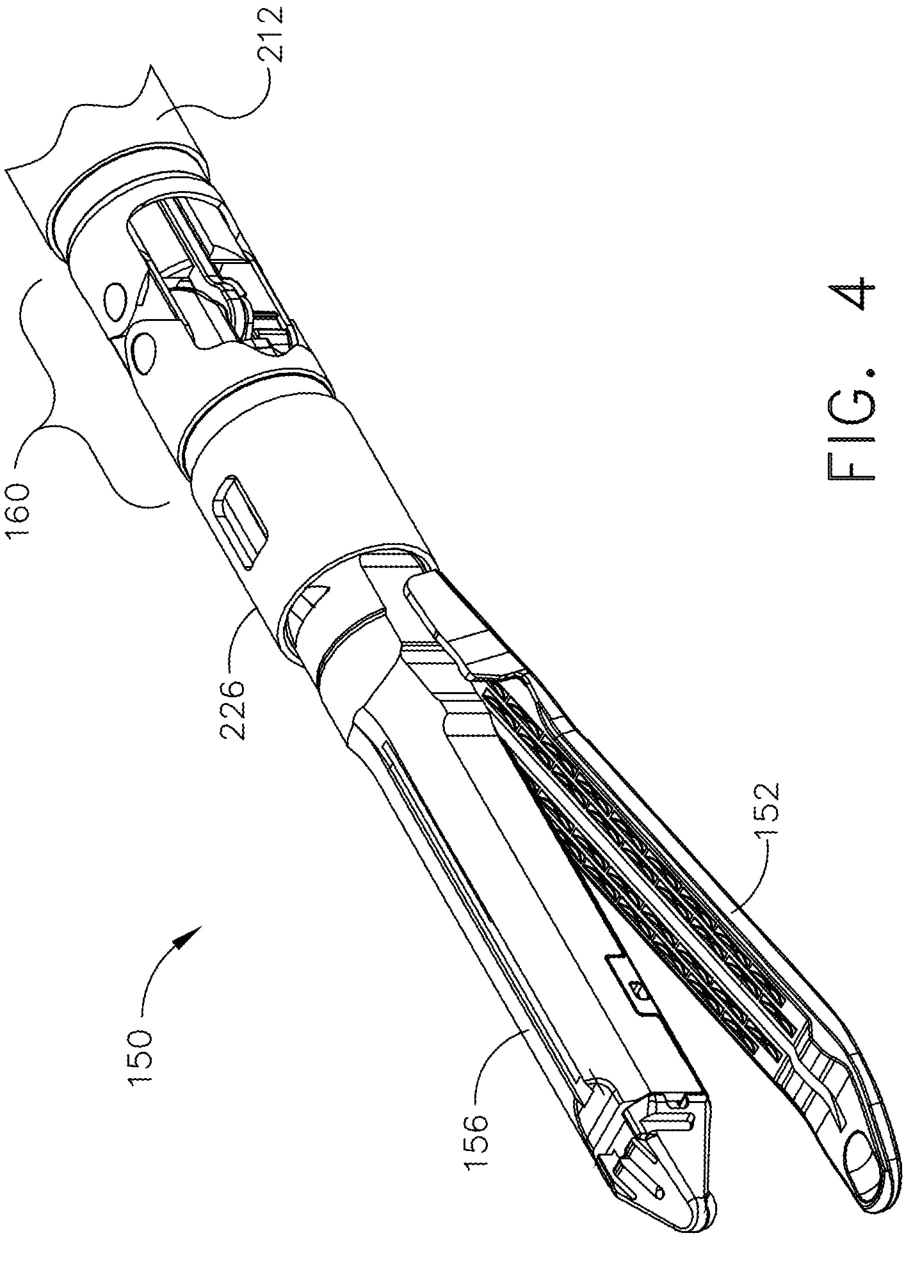
FIG. 4 shows a perspective view of an end effector of the surgical instrument, according to aspects of the present disclosure.

As shown in FIG. 4, the surgical instrument 100 includes an end effector 150 disposed at the distal end 108 of the surgical instrument 100. As shown, the end effector 150 includes an anvil 152 and a channel 156. As will be described in greater detail herein, the anvil 152 can be caused to move with respect to the channel 156 to open and close the end effector 150. Furthermore, as will be described in greater detail herein, the surgical instrument 100 includes a closure ring 226 and a closure tube 212 that can be actuated to cause the anvil 152 to open and close with respect to the channel 156. The anvil 152 can be opened by retracting the closure ring 226 from the anvil 152.

Figure 5A:
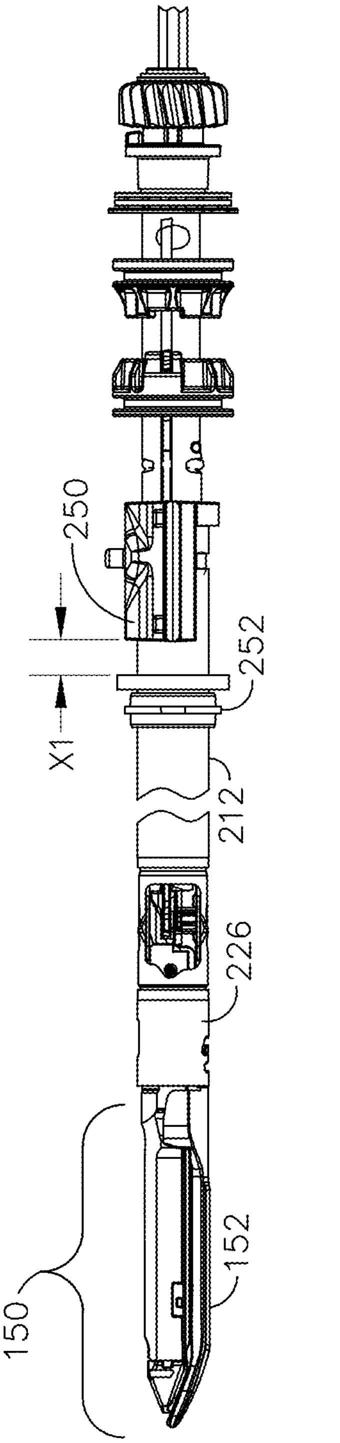
FIG. 5A shows a closure subsystem in a closed configuration, according to aspects of the present disclosure.
Figure 5B:
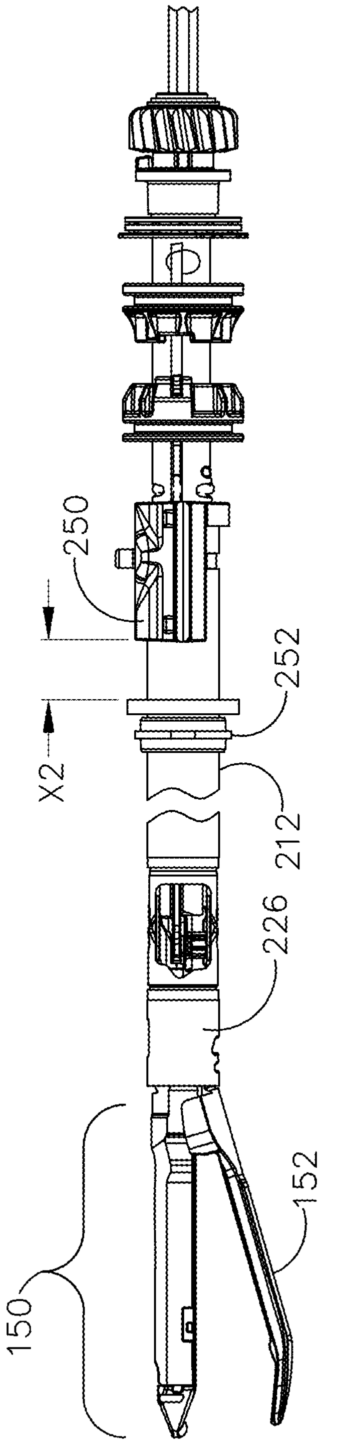
FIG. 5B shows a closure subsystem in an open configuration, according to aspects of the present disclosure.

FIG. 5A illustrates an end effector 150 in a closed configuration while FIG. 5B illustrates an end effector 150 in an open configuration. The anvil 152 of the end effector 150 can be opened and closed by operation of a closure ring 226 that is coupled to the anvil 152 and can be slid proximally and distally by the closure tube 212. As the closure ring 226 is slid distally the closure ring 226 causes the anvil 152 to close. As the closure ring 226 is slid proximally, the closure ring 226 causes the anvil 152 to open. The closure ring 226 can be caused to move between the opened and closed position by actuation of the closure tube 212. As the closure tube 212 is slid proximally and distally, the closure tube 212, which is engaged with the closure ring 226, causes the closure ring 226 to also slide proximally and distally, thereby opening and closing the anvil 152.

As shown in FIGS. 5A and 5B, the closure tube 212 can be actuated by movement of a closure yoke 250 between an open position in which the anvil 152 is opened and a closed position in which the anvil 152 is closed. The closure yoke 250 can slide axially in a proximal direction to open the anvil 152 and slide axially in a distal direction to cause the anvil 152 to close. In other words, when the closure yoke is in the open position, a distance X1 between the closure yoke 250 and a distal roll bushing 252 (which remains stationary) will be less than when the closure yoke 250 is in the closed position and a distance between the closure yoke 250 and the distal roll bushing 252 is X2. As will be described in greater detail herein, the closure yoke 250 can be transitioned between the open and closed positions by actuation of several gears.

Figure 6A:
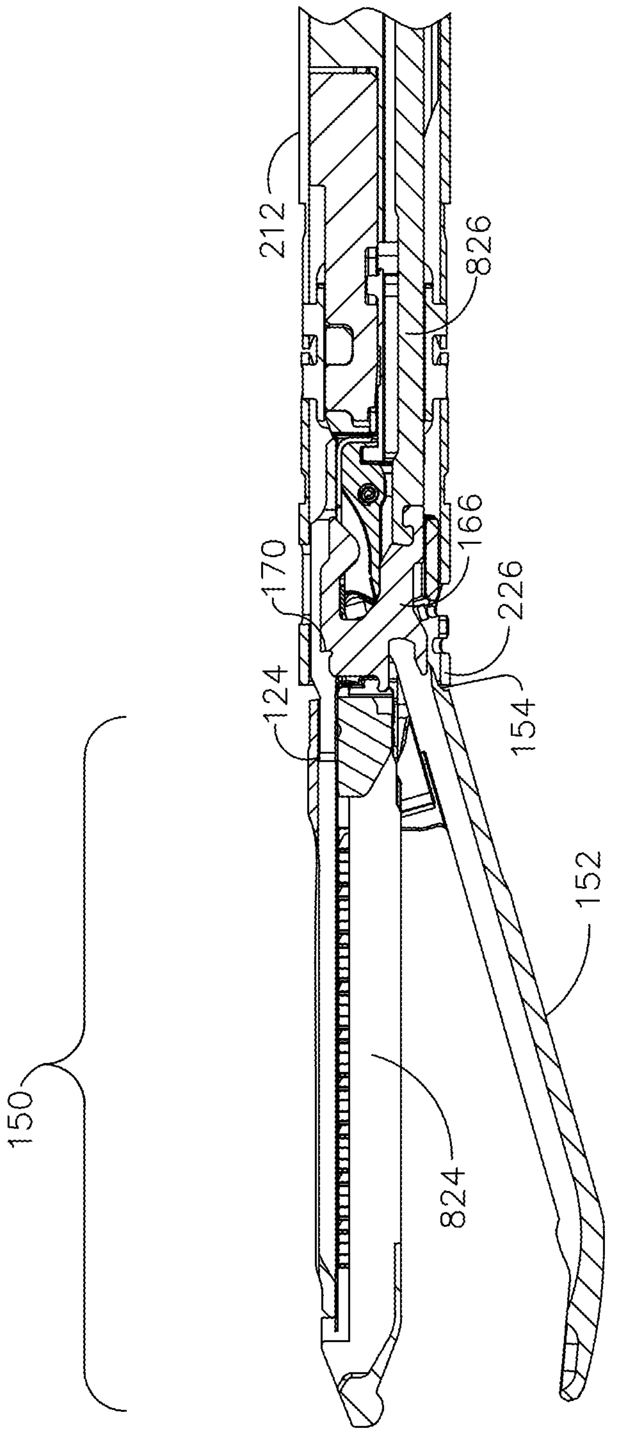
FIG. 6A shows a section view of the end effector and closure subsystem, according to aspects of the present disclosure.

FIG. 6A is a cross sectional view of the end effector 150 showing the end effector 150, the closure ring 226 and the closure tube 212. The closure ring 226 can be coupled to the anvil 152 such that the anvil 152 is caused to open when the closure ring 226 is slid proximally and caused to close when the closure ring 226 is slid distally. In this way, the closure subsystem 200 must be actuated between the opened and closed position to transition the anvil 152 between the open and closed position. In other words, it is not possible to open or close the anvil 152 without also actuating the other components of the closure subsystem 200.

Figure 6B:
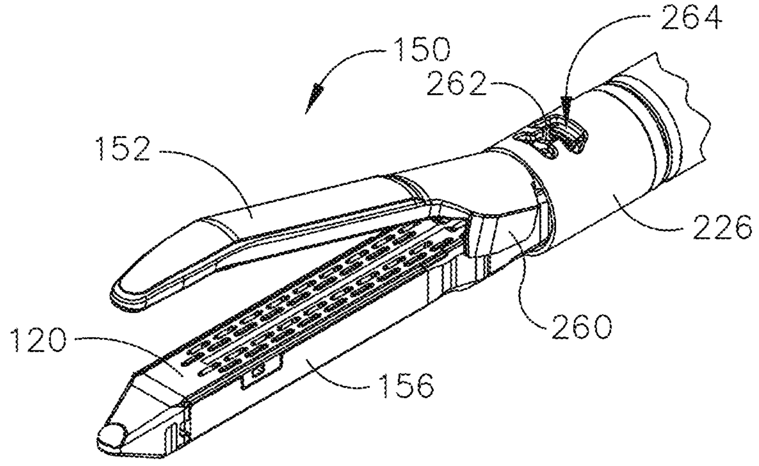
FIG. 6B is a perspective view of the end effector and closure system, according to aspects of the present disclosure.
Figure 6C:
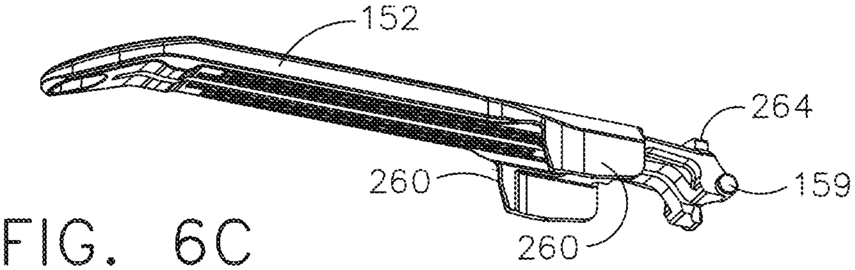
FIG. 6C is a perspective view of the anvil, according to aspects of the present disclosure.
Figure 6D:
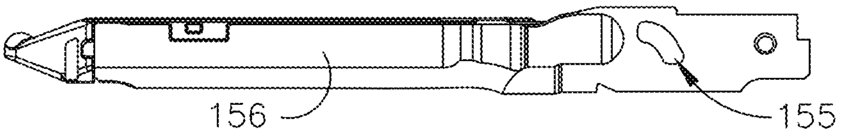
FIG. 6D is a perspective view of the channel, according to aspects of the present disclosure.

FIG. 6B is a perspective view of the end effector showing the anvil 152, the channel 156, a cartridge installed in the channel 120, and the closure ring 226. The anvil 152 includes flanges 260 that can extend outwardly at a proximal end of the anvil 152. As shown in FIG. 6C, the anvil 152 further includes an anvil tab 264 positioned at a proximal end of the anvil 152. The anvil tab 264 is configured to contact one or more closure ring tabs 262 that can extend inwardly from the closure ring 226 to cause the anvil 152 to open and close.

As shown in FIG. 6C, the anvil 152 includes one or more anvil pins 159 that can extend into an opening 155 in the channel 156. Opening 155 is an elongate slot in this example. It should therefore be understood that anvil pin 159 slides along opening 155 in addition to pivoting about its own axis within opening 155. This action may still be regarded as "pivoting" as defined herein, even though the pivot axis translates with anvil pin 159 along opening 155 and is not in a fixed position.

As closure ring 226 translates distally in response to advancement of closure tube 212, closure ring 226 translates relative to anvil 152 to engage anvil 152. Closure ring 226 engages anvil 152 to translate anvil 152 distally by contacting the anvil ramp 154 and causing the anvil 152 to pivot. As anvil 152 continues to translate distally, the closure ring 226 causes the anvil 152 to close. Once end effector 150 is closed, the tissue captured between anvil 152 and channel 156 may be cut and stapled.

Once tissue positioned in the end effector 150 is cut and stapled, anvil 152 may be opened to release the tissue. End effector 150 may then be opened to replace staple cartridge 120 with a new staple cartridge. To open end effector 150, the closure ring 226 can be translated proximally by the closure subsystem 200. As closure ring 226 translates proximally, the one or more closure ring tabs 262 engage the anvil tab 264 to pull anvil 152 proximally. As anvil 152 translates proximally, the anvil 152 pivots away from channel 156 to an open position.

Closure Subsystem

Figure 7A:
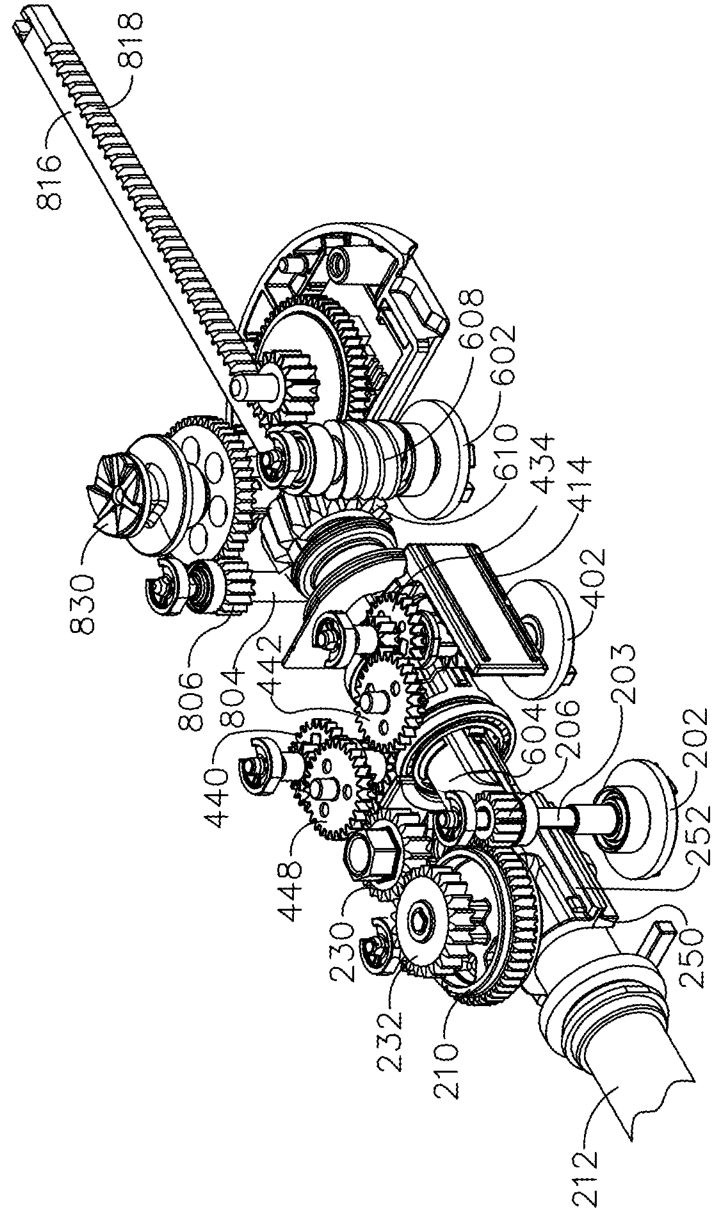
FIG. 7A is a detail view of a closure subsystem, according to aspects of the present disclosure.
Figure 7B:
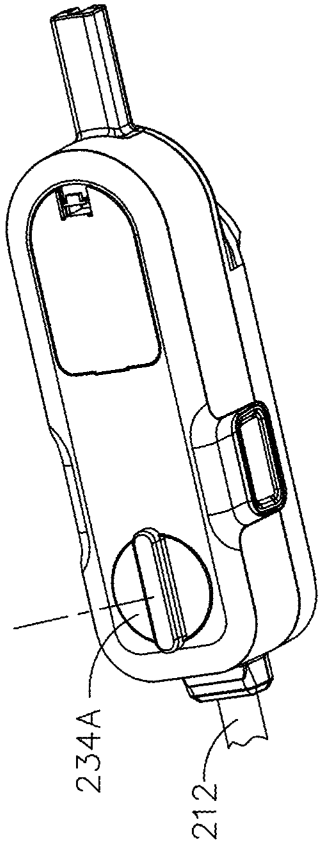
FIG. 7B is a perspective view of the housing, according to aspects of the present disclosure.
Figure 7C:
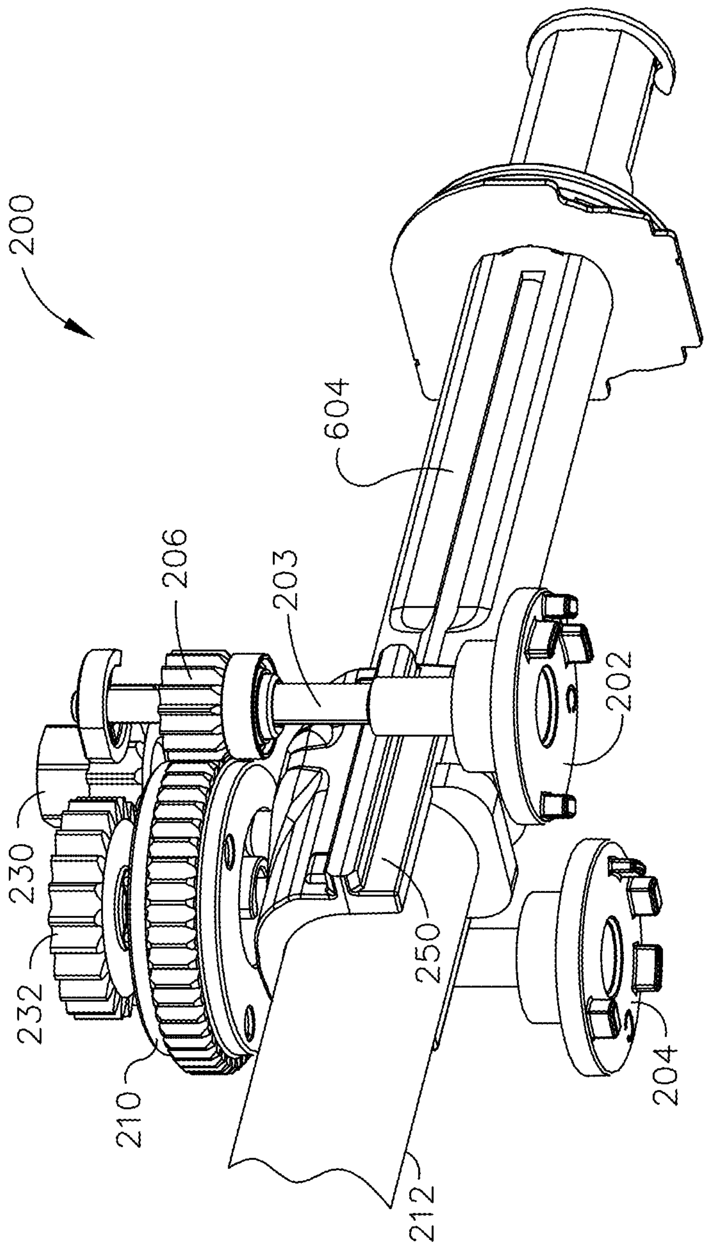
FIG. 7C is another detail view of a closure subsystem, according to aspects of the present disclosure.
Figure 7D:
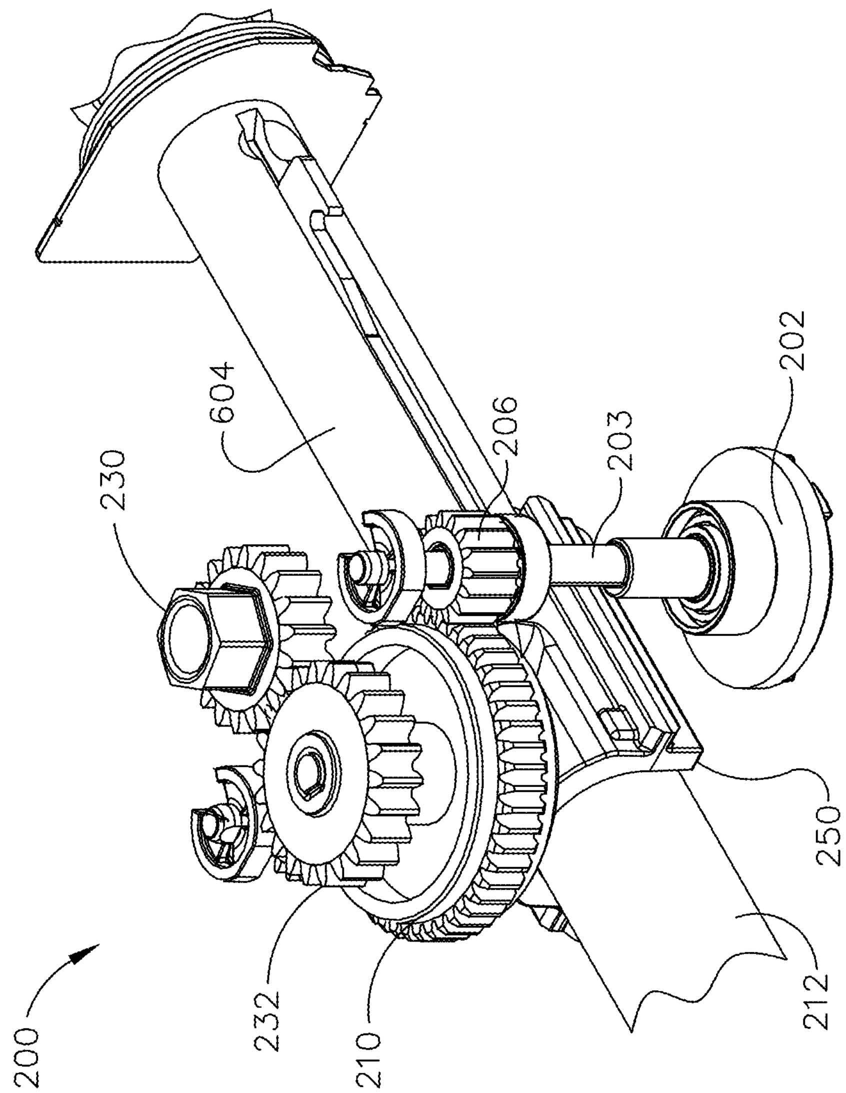
FIG. 7D is another detail view of a closure subsystem, according to aspects of the present disclosure.

FIGS. 7A, 7C, 7D, 7E, and 7I are detail views of a closure subsystem 200, according to aspects of the present disclosure. FIGS. 7A and 7D are top perspective views while FIG. 7C is a bottom perspective view of the closure subsystem 200. The closure subsystem 200 includes a first closure input puck 202 and a second closure input puck 204 (shown in FIG. 7C). The first closure input puck 202 can be configured to engage with a first rotating feature of the robotic arm and the second closure input puck 204 can be configured to engage with a second rotating feature of the robotic arm. In this way, the robotic arm can be configured to transmit a greater amount of force to the closure subsystem 200 to cause the anvil 152 to open and close than would be possible with only a single input puck.

The first closure input puck 202 can be coupled to a first closure input rod 203 that extends into the outer housing 102. The first closure input rod 203 can be further coupled to a first closure spur gear 206. Thus, when the first closure input puck 202 rotates, it will also cause the first closure input rod 203 and the first closure spur gear 206 to rotate. Similarly, the second closure input puck 204 can be coupled to a second closure input rod 205 that extends into the outer housing 102. The second closure input rod 205 can be further coupled to a second closure spur gear 208. Thus, when the second closure input puck 204 rotates, it will also cause the second closure input rod 205 and the second closure spur gear 208 to rotate. The first closure input rod 203 can be held in place by a first retention clip 218 and the second closure input rod 205 can be held in place by a second retention clip 220.

Figure 8A:
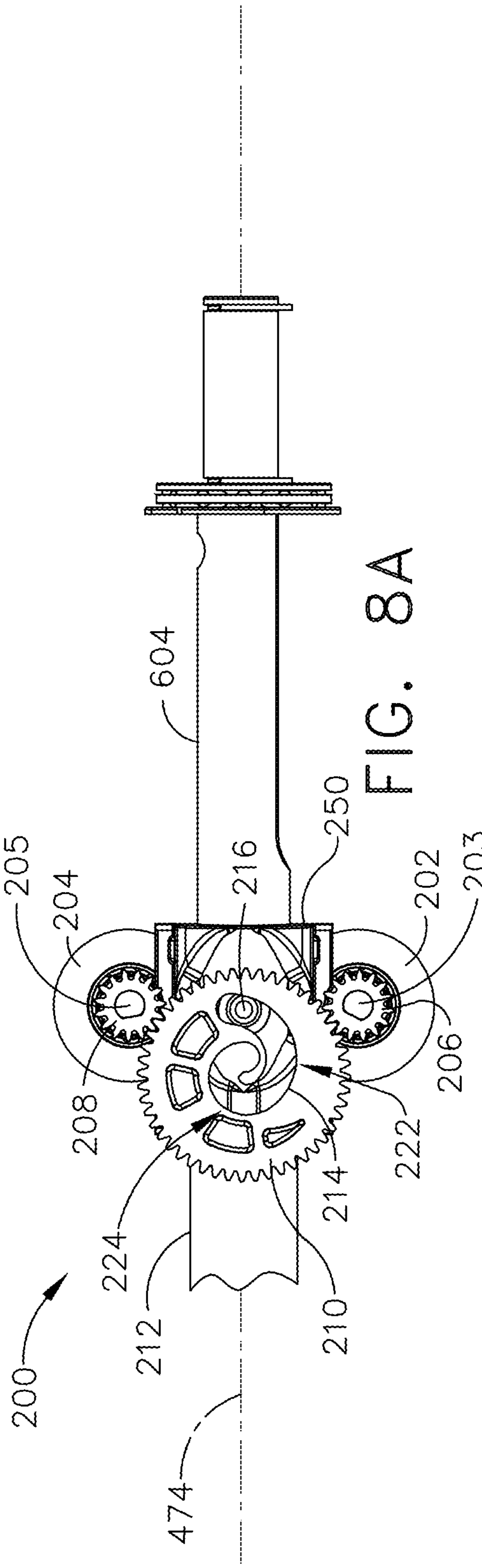
FIG. 8A is a top view of components of the closure subsystem in a first configuration while 8B is a top view of components of the closure subsystem in a second configuration, according to aspects of the present disclosure.
Figure 8B:
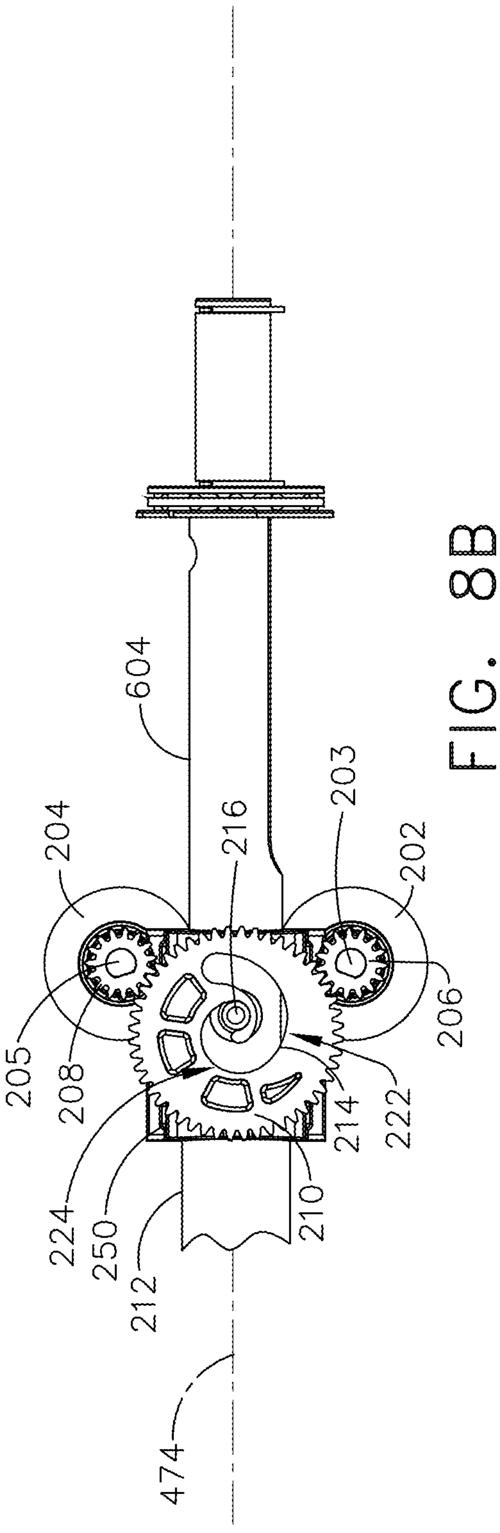
FIGS. 8C and 8D are detail views of a closure cam gear, according to aspects of the present disclosure.

The first closure spur gear 206 and the second closure spur gear 208 can each be rotationally engaged with a closure cam gear 210. As shown in FIGS. 8A and 8B, the closure cam gear 210 includes a closure cam track 214 that can be configured to receive a yoke pin 216 that can be coupled to the closure yoke 250. As the closure cam gear 210 rotates, the closure cam track 214 causes the yoke pin 216 to slide proximally and distally, thereby causing the closure yoke 250 to slide proximally and distally. In other words, as the closure cam gear 210 is rotated in a first direction, the closure cam track 214 will guide the yoke pin 216 along the closure cam track 214 in either the proximal or distal direction. Because the yoke pin 216 is coupled to the closure yoke 250, movement of the yoke pin 216 proximally or distally causes the closure yoke 250 to move proximally or distally. As explained previously, movement of the closure yoke 250 causes the anvil 152 to open or close.

The closure cam track 214 can comprise a non-linear track that can be configured to have a changing movement profile as the closure cam gear 210 rotates. As shown in FIGS. 8A and 8B, a cam track 214 can include a non-linear profile. In some implementations, the cam track 214 can be a logarithmic spiral. The cam track 214 is not necessarily fully logarithmic, and in some instances can be represented by higher order polynomials, as some implementations can include a portion that is non-linear, a portion that has a constant radius, and a portion that connects the non-linear and constant radius portions. These different portions can be created by splines. One novel aspect of this non-linear cam track 214 design is that it can be shaped such that once the yoke pin 216 reaches a portion of the cam track 214 with a constant radius, the closure cam gear 210 rotates but the yoke pin 216 does not move axially. This feature can provide benefits by accounting for, and providing tolerance for, robotic inaccuracies.

Figure 8C:
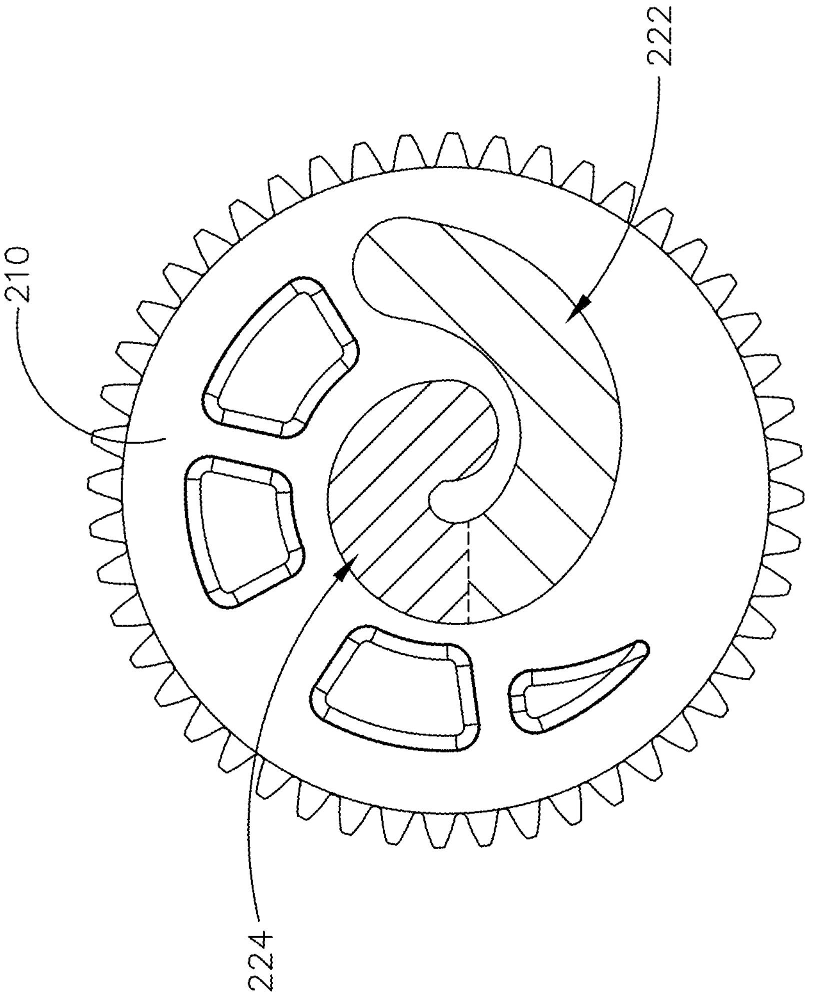
Figure 8D:
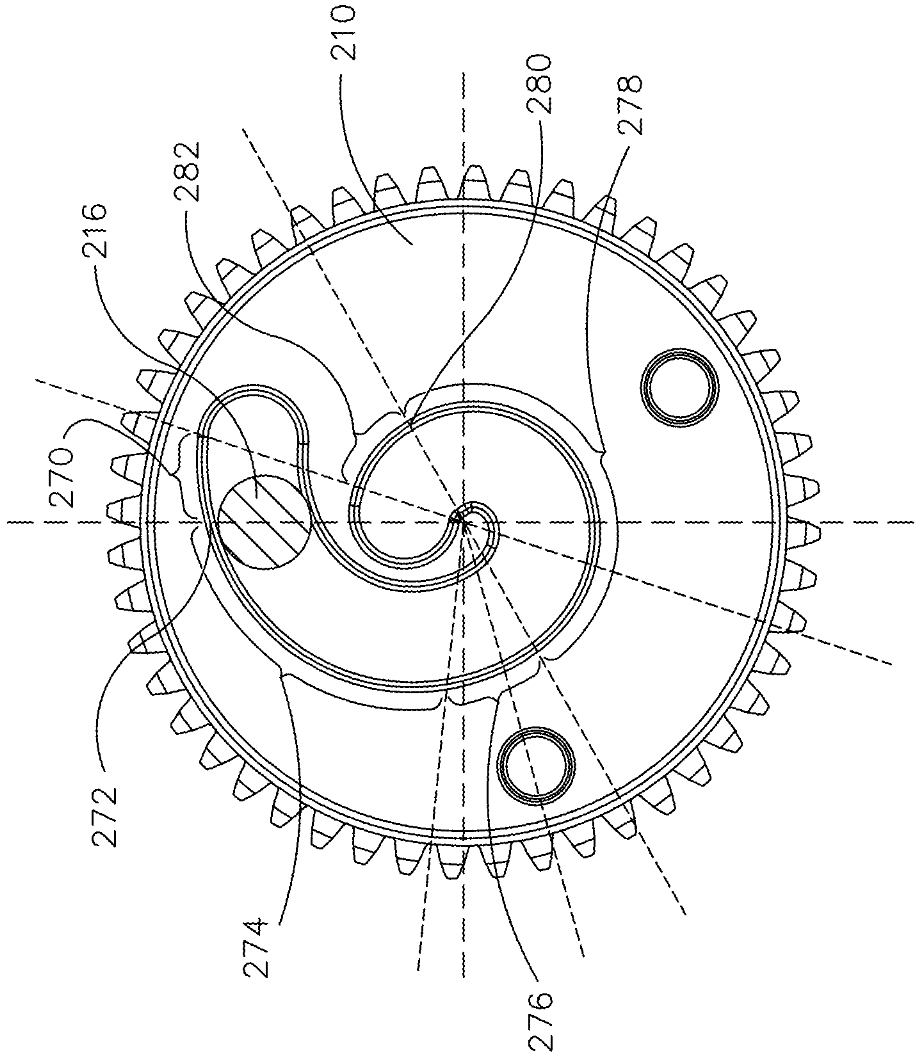

As shown in FIG. 8C, the closure cam track 214 can comprise a first zone 222 and a closure zone 224. The first zone 222 of the closure cam track 214 can be configured to cause the yoke pin 216 and, subsequently, the anvil 152 to compress tissue without causing a great amount of force. The closure zone 224 of the closure cam track 214, on the other hand, can be configured to cause the anvil 152 to compress down on tissue with a force sufficient to keep the end effector 150 in place for cutting and/or stapling of the tissue. The final rotational position of the closure cam track 214, and the overall configuration of the other components of the closure subsystem 200, creates a closure load that meets the requirements of the particular application. In other words, once the yoke pin 216 reaches a final rotational position, the combination of the closure subsystem 200 components can cause the anvil 152 to move to a closed position to close down on tissue. It will be appreciated, however, that the first zone 222 and the closure zone 224 can be configured to comprise alternative percentages of the closure cam track 214 depending on the particular application. Furthermore, the slope of the closure cam track 214 at the first zone 222 and the closure zone 224 can be varied to affect the speed and force with which the anvil 152 opens and closes. It will be understood that the cam track 214 is contiguous, non-linear, and smooth, so FIGS. 8C and 8D depicting the different "zones" is not to indicate that there is a break or discontinuity in certain sections of the cam track 214. FIG. 8A shows a fully open configuration, where the yoke pin 216 is at a position within the cam track 214 such that the anvil 152 is fully open, thereby maximizing the amount of tissue that can be placed in the jaws (e.g., anvil and channel) of the end effector 150. FIG. 8B shows a fully closed configuration, where the yoke pin 216 is within a constant radius portion of the cam track 214 (in this view the yoke pin 216 is also at the very end of the cam track 214). A fully closed configuration can indicate that the surgical instrument 100 is ready to proceed with firing (e.g., transection and/or stapling). Partially open configurations can exist between the examples shown in FIGS. 8A and 8B wherein the system can grasp tissue.

Referring now to FIG. 8D, which is a bottom view of the closure cam gear 210, the view shows different regions of the cam track 214 that can provide different movement profiles for the yoke pin 216. Referencing this view in FIG. 8D, as the closure cam gear 210 rotates clockwise, the yoke pin 216 translates downward in the view (downward being distally in relation to the shaft 604, see FIGS. 8A and 8B). The regions of the cam track 214 can provide different movement profiles depending on where in the cam track 214 the yoke pin 216 is located. For example, the closure cam gear 210 in FIG. 8D has indications of degrees for reference, up being labeled 0°, left being labeled 90°, down being labeled 180°, and right being labeled 270°. The cam track 214 can include an open dead zone 270 that exists between around −20° and around 0°. The open dead zone 270 is a region beyond an open position 272 that provides a level of tolerance should the closure cam gear 210 be rotated beyond the open position 272. The open position 272, or home position, can be a hard stop position where the closure ring 226 is positioned proximally, allowing the anvil 152 to be fully open (see FIG. 5B). The cam track 214 of FIG. 8D includes a high speed compression region 274 positioned in the next portion of the cam track 214 beyond the open position 272. This high speed compression region 274 can extend from around 0° to around 90°. The high speed compression region 274 has a curvature that enables the yoke pin 216 to transition distally quickly while providing a low amount force (for example clamping force on the anvil 152). This high speed compression region 274 can enable the surgical instrument 100 to grab and position the target tissue. At around 90° on the closure cam gear 210 of FIG. 8D is a force transition region 276. Extending beyond the force transition region 276 is a high force region 278. The high force region 278 can extend from around 90° to around 300° on the closure cam gear 210 of FIG. 8D. This region provides a low speed, high force movement profile for the distal movement of the yoke pin 216. The high force region 278, for example, can be a portion of the movement profile that begins to put pressure on the tissue that is being cut and/or stapled. At around 300° on the closure cam gear 210 of FIG. 8D is a closing target 280. Any point beyond the closing target 280 can be considered as closed, as in the force and distal movement yoke pin 216 are considered met. Extending beyond the closing target 280, and from about 300° to the end of the cam track 214, is a constant force region 282. Like the constant radius portion described above, the constant force region 282 can be a section of the cam track 214 where the closure cam gear 210 rotates but the yoke pin 216 does not move axially. This can help to provide tolerance for any positional error by the surgical robot 1100.

The closure subsystem 200 can further include a manual closure spur gear 230 that is coupled to a manual closure handle 234 (as shown in FIGS. 7B and 7E-7I) that extends through the outer housing 102. The manual closure handle 234 can be used, for example, by a surgical staff if the surgical robot is unable to open or close the anvil 152. The manual closure spur gear 230 can be rotationally coupled to a manual closure cam gear 232 that can be keyed to the closure cam gear 210. In this way, rotation of the manual closure handle 234 will cause the manual closure spur gear 230 and the manual closure cam gear 232 to rotate, thereby causing the closure cam gear 210 to rotate and open or close the anvil 152. As will be appreciated, the manual closure handle 234 provides a surgical staff with the ability to open and close the anvil 152 when the surgical instrument 100 is disconnected from a surgical robot or to override the opening or closing of the anvil 152 when connected to the surgical robot.

As shown in FIGS. 7E-7I, the manual closure handle 234, in some examples, includes a manual closure handle grip 236 and a manual closure handle clip 238. The manual closure handle grip 236 can extend beyond an outer portion of the housing 102 such that the physician or surgical staff can grip the manual closure grip 236 and rotate it to cause the anvil 152 to open or close. The manual closure handle clip 238 can be configured to extend through the manual closure handle grip 236 and into the housing 102 to attached the manual closure handle 234 to the housing 102. The manual closure handle clip 238 can include one or more protruding features that can snap into place when pushed into the housing 102 to attached the manual closure handle 234 to the housing 102. In other examples, the manual closure handle grip 236 and the manual closure handle clip 238 can be integrated into a single component.

Figure 7F:
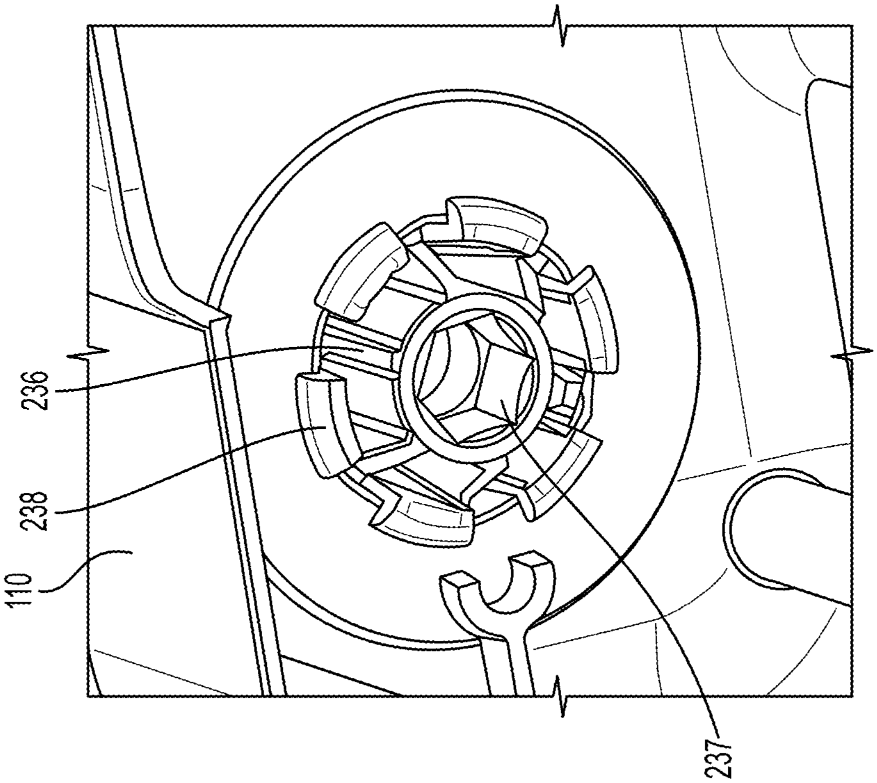
FIG. 7F is an underside perspective view of the manual closure handle, according to aspects of the present disclosure.
Figure 7E:
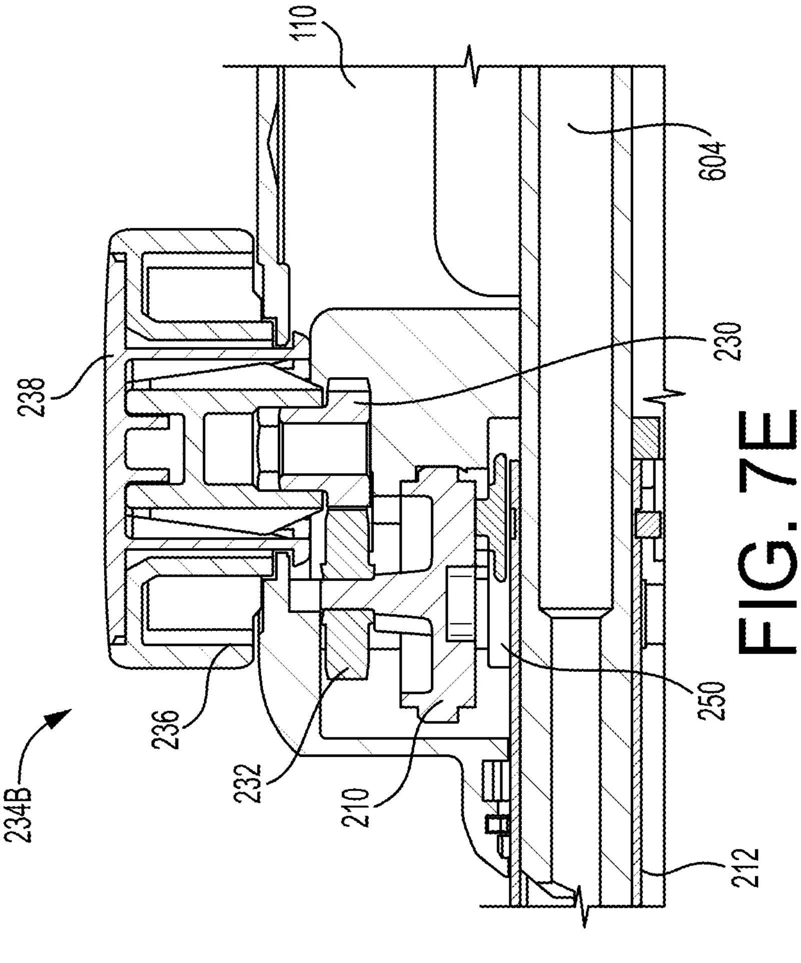
FIG. 7E is a cross-sectional view taken vertically along the longitudinal axis of the surgical instrument and showing details of a manual closure handle, according to aspects of the present disclosure.
Figure 7H:
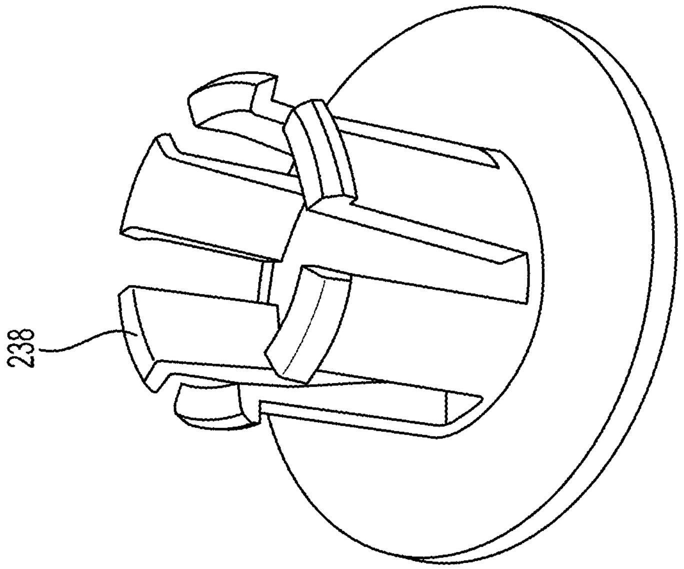
FIG. 7H is a detail view of a manual closure handle clip, according to aspects of the present disclosure.
Figure 7G:
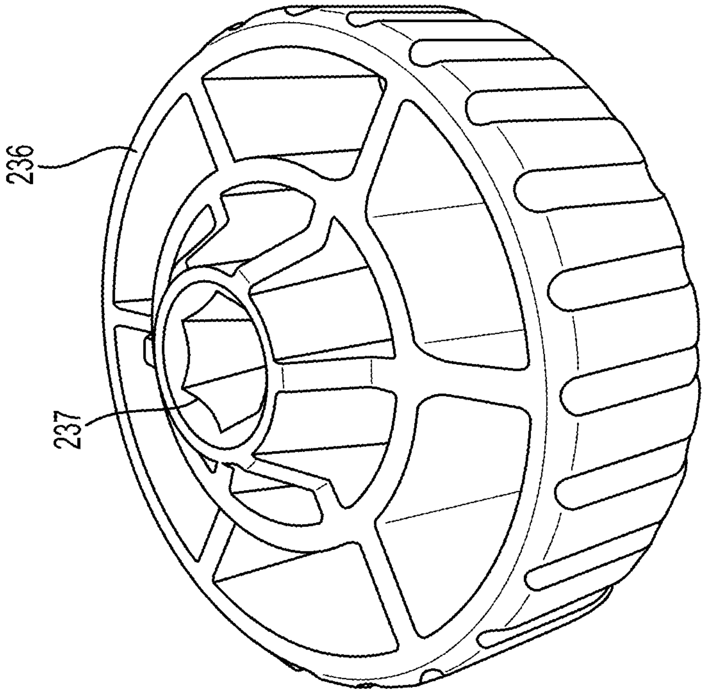
FIG. 7G is a detail view of a manual closure handle grip, according to aspects of the present disclosure.
Figure 7I:
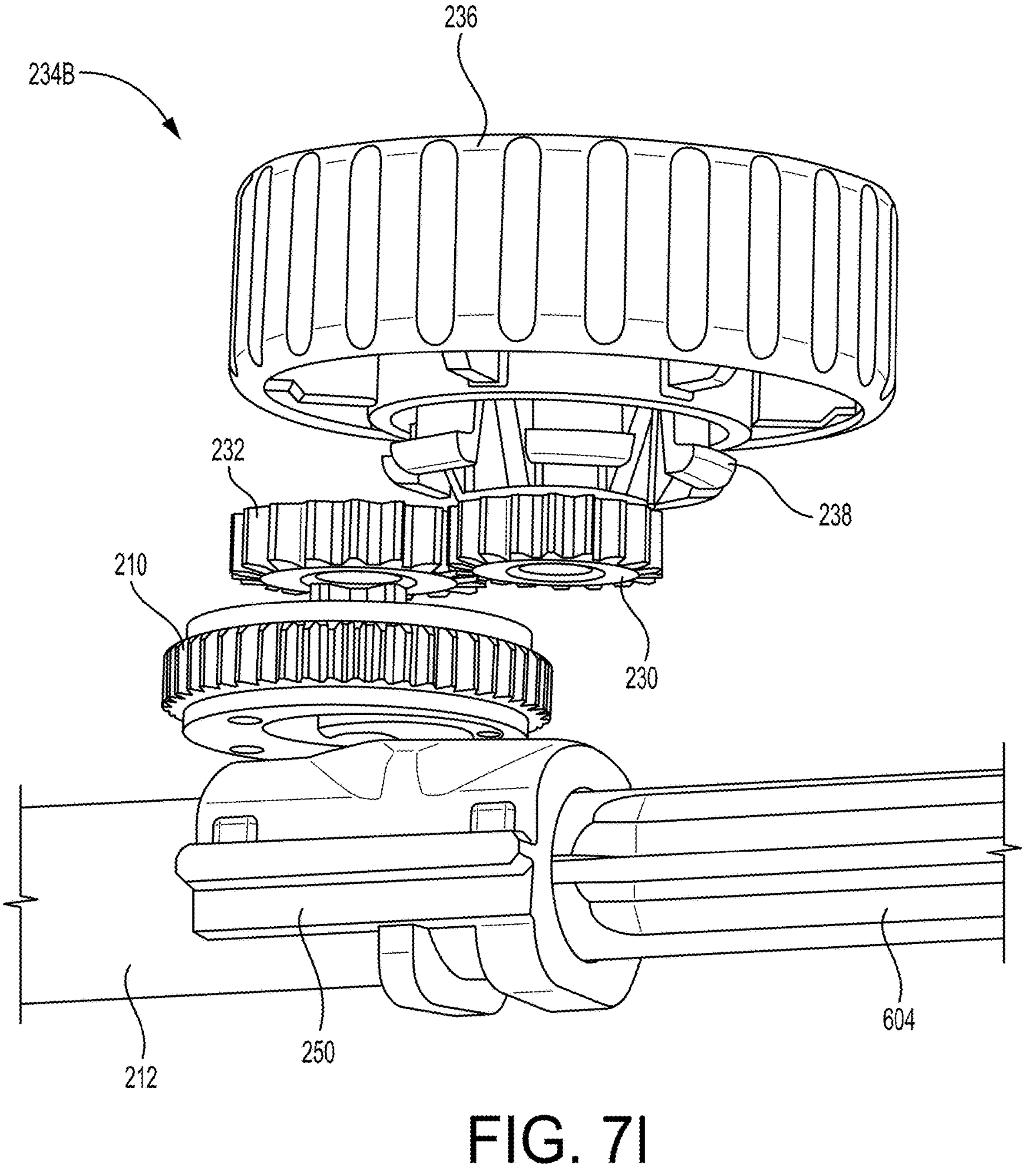
FIG. 7I is a detail view of the closure subsystem with manual closure handle, according to aspects of the present disclosure.

The manual closure handle grip 236 can attach to the manual closure spur gear 230 by, for example but not limitation, receiving a protrusion of the manual closure spur gear 230 into a recess formed into the manual closure handle grip 236 (as shown in FIGS. 7E and 7F). The manual closure handle grip 236 can include engagement surfaces 237 that can align with corresponding engagement surfaces of the manual closure spur gear 230 to transfer forces from the manual closure handle grip 236 to the manual closure spur gear 230 when rotated. For example, the protrusions of the manual closure spur gear 230 and the recess of the manual closure handle grip 236 can be a hex head or other similar features.

Although not shown, in some examples, the manual closure handle grip 236 could include geometry that limits the travel, or provides some resistance to the travel, of the manual closure handle grip 236 at predetermined locations such that the manual closure handle grip 236 is stopped or at least slowed at positions corresponding to desired positions of the opening and closing of the anvil 152. Alternatively, or in addition, the manual closure handle grip 236 or the manual closure handle clip 238 can include markings, colors, protrusions, recesses, etc. that indicate the position of the anvil 152. In some examples. The manual closure handle grip 236 or the manual closure handle clip 238 can include transparent features that reveal indicators at certain positions of rotation to indicate the status. Furthermore, the manual closure handle 230 and/or the closure subassembly 200 can include torque limiting features to prevent over torquing of the closure subassembly 200.

Articulation Subsystem

Figure 9:
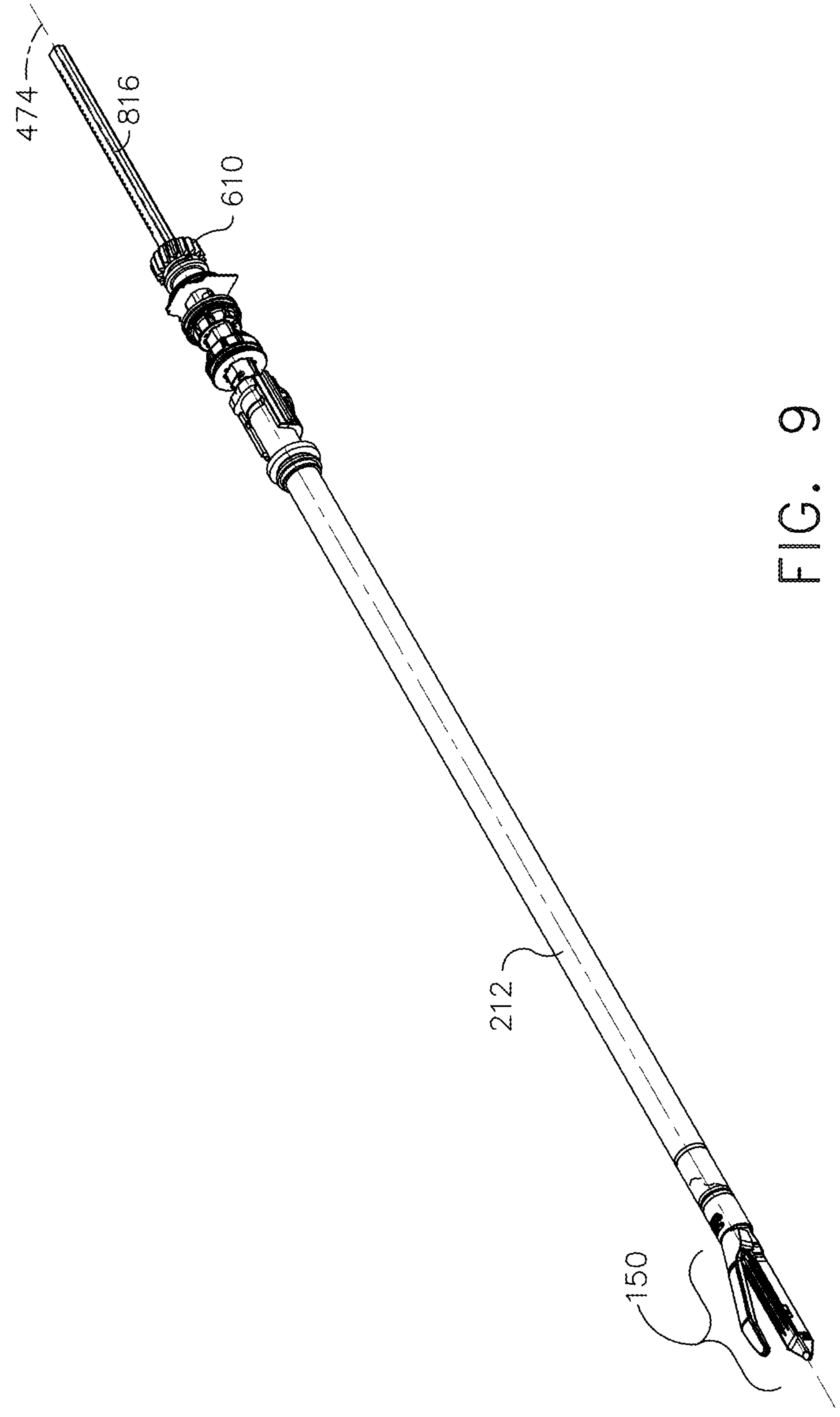
Figure 10:
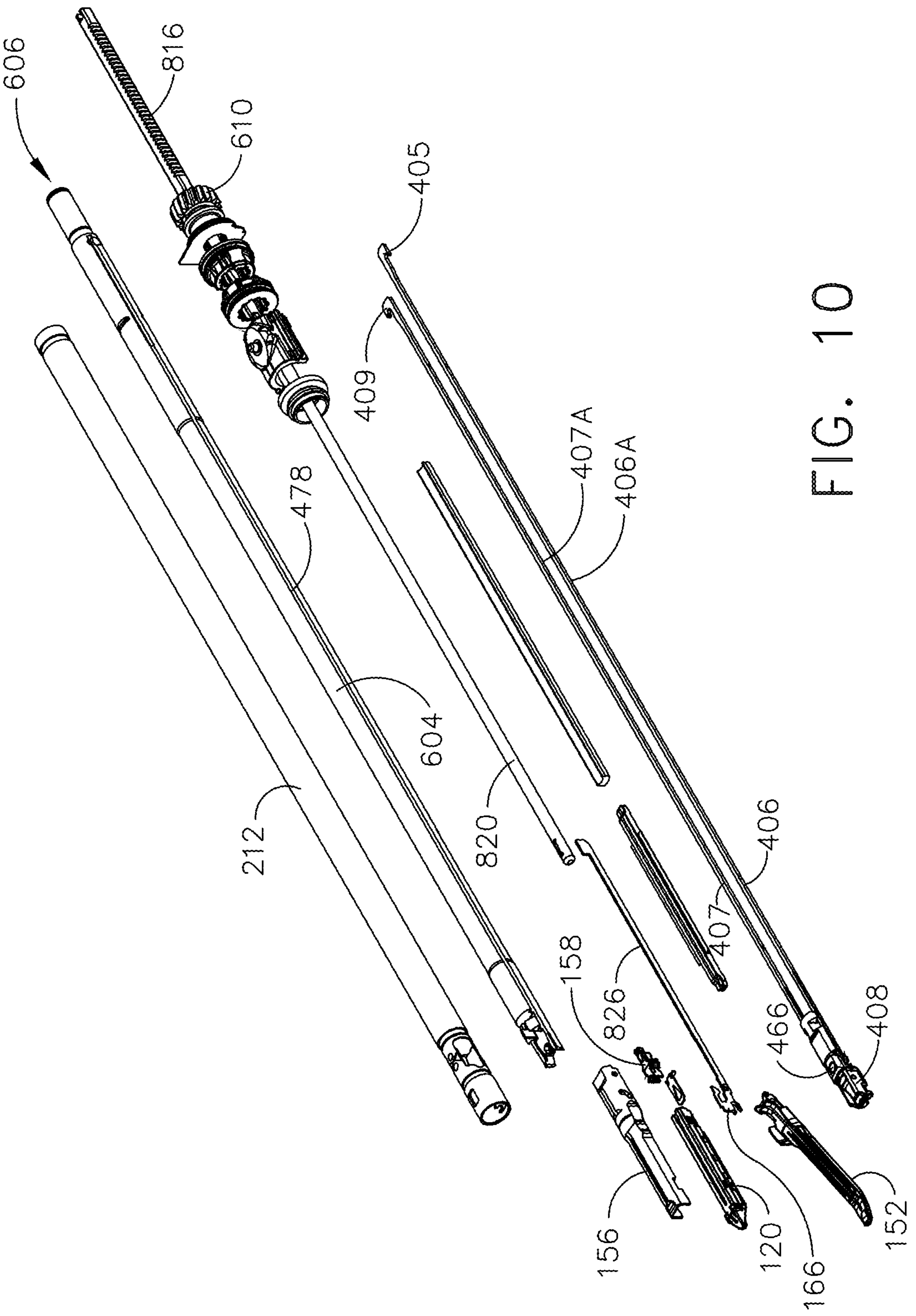
FIG. 10 is an exploded view of the surgical instrument, according to aspects of the present disclosure.

FIG. 9 is a perspective view of the surgical instrument 100 while FIG. 10 is an exploded perspective view of the surgical instrument 100. As shown, the surgical instrument 100 includes a cartridge 120 that includes staples configured to staple tissue. The surgical instrument 100 can further include a knife guide 158, a firing rod 820, and a firing rack 816 that can cause a knife to cut tissue, as will be described in greater detail herein. Furthermore, the surgical instrument 100 includes a shaft 604 having a shaft lumen 606. The shaft 604, as will be described in greater detail herein, can be disposed within the closure tube 212 and be coupled to a worm follower 610 that can cause the shaft 604 and end effector to rotate about the longitudinal axis 474 of the surgical instrument 100.

The surgical instrument 100 includes an articulation subsystem 400. As shown in FIG. 10, the surgical instrument 100 includes a first articulation rod 406A and a second articulation rod 407A that can be configured to cause a distal channel retainer 408 and, subsequently, the end effector 150 to articulate in a first and second direction transverse to a longitudinal axis 474 of the surgical instrument 100. The first articulation rod 406A and the second articulation rod 407A can be configured to be at least partially disposed in a rod groove 478 disposed on either side of the shaft 604.

Views of the articulation of the distal end of the surgical instrument 100 are shown in FIGS. 11A, 11B, 12A, 12B, and 12C while detailed views of the proximal portions of an example articulation subsystem 400 are provided in FIGS. 13A-15C. The articulation subsystem 400 includes a first articulation rod 406A and a second articulation rod 407A that each extend distally to a distal channel retainer 408. The proximal end of the first articulation rod 406A and the second articulation rod 407A can each include a hook (first articulation rod hook 405 and second articulation rod hook 409, shown in FIGS. 10, 15A, 15B, and 15C) or other attachment that constrains the articulation rod proximally (e.g., to a first articulation bushing 426 and a second articulation bushing 428). In some examples, the first articulation rod 406A and the second articulation rod 407A can each be pinned, bolted, welded, adhered, or otherwise attached to a first rack 414A and a second rack 418A, respectively. The distal end of the first articulation rod 406A and the second articulation rod 407A can each be connected to a distal channel retainer 408 that can pivot back and forth (e.g., left and right) to move, or articulate, an end effector 150 of the surgical instrument 100. The first articulation rod 406A can be attached to the distal channel retainer 408 via a first channel retainer pin 410 and the second articulation rod 407A can be attached to the distal channel retainer 408 via a second channel retainer pin 411. An attachment end 468 of the distal channel retainer 408 can, for example, be attached to a channel 156 of the end effector 150 to articulate the end effector 150. The attachment end 468 can also include a band slot 484 for a series of bands 826 to pass through, which are described in greater detail herein with respect to the transection subsystem 800.

Figure 11A:
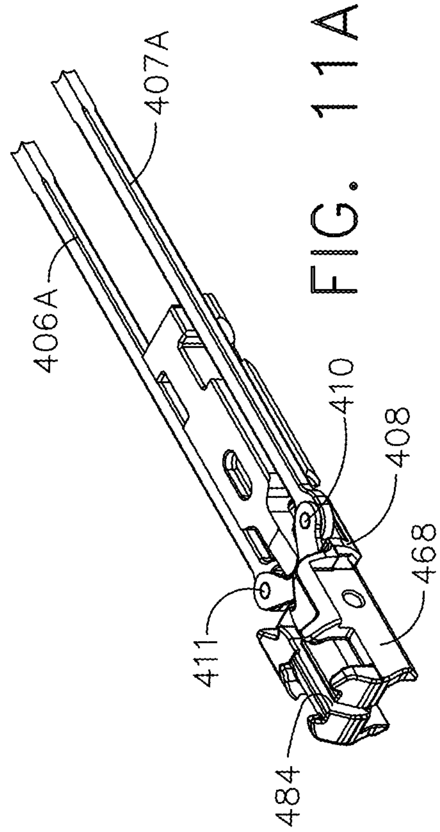
FIGS. 11A and 11B show detail views of components of the articulation subsystem, according to aspects of the present disclosure.
Figure 11B:
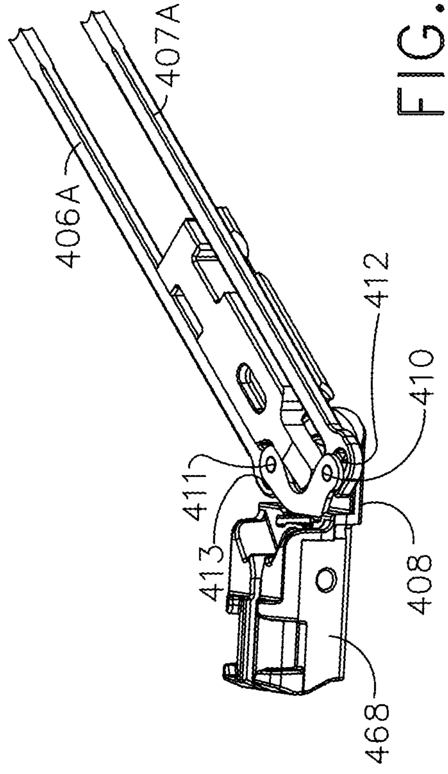
Figure 12A:
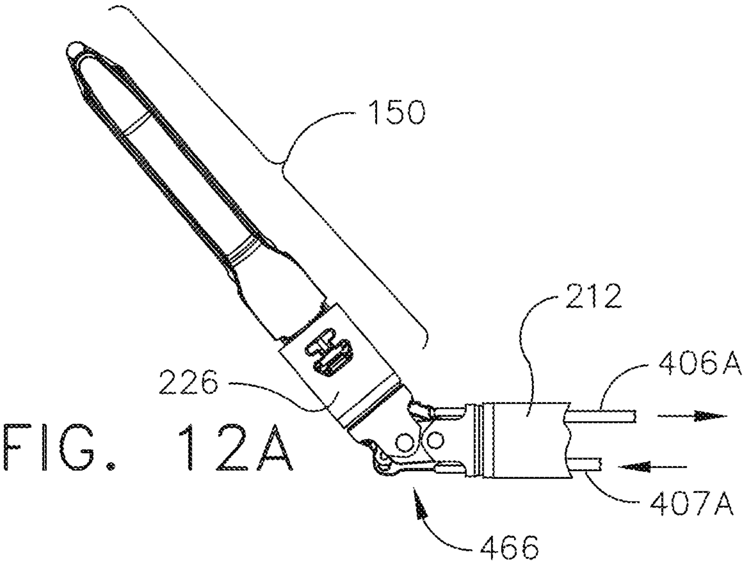
FIG. 12A shows the articulation system fully articulated in one direction.
Figure 12B:
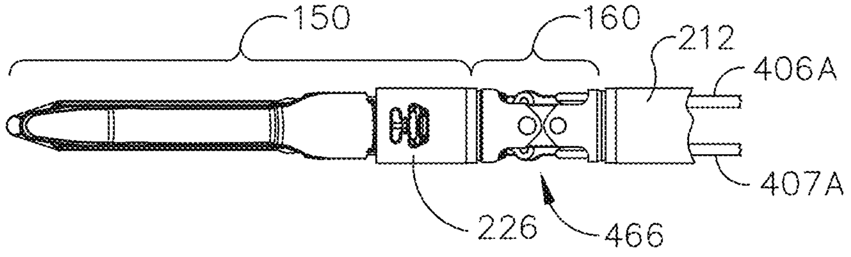
FIG. 12B shows the articulation system at 0° degrees of articulation.
Figure 12C:
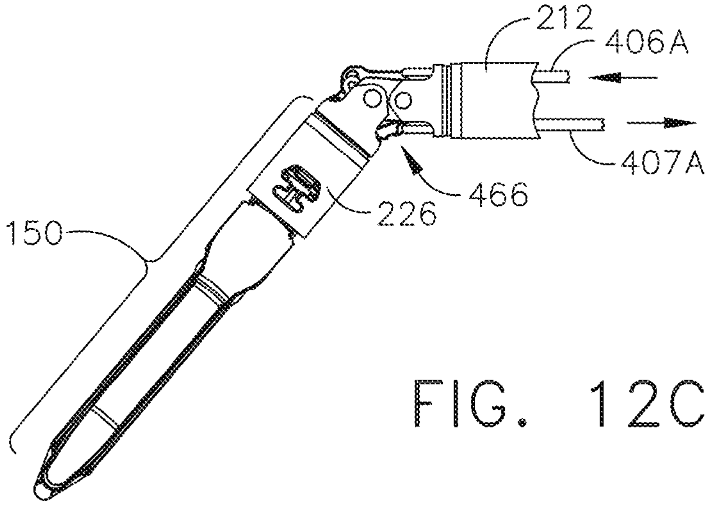
FIG. 12C shows the articulation system fully articulated in another direction.

Referring now to FIGS. 12A, 12B, and 12C, the first articulation rod 406A and the second articulation rod 407A can articulate the distal channel retainer 408 back and forth about an articulation pivot point 466 by pushing or pulling a respective side of the distal channel retainer 408. FIG. 12A illustrates the end effector 150 articulated to a first position, FIG. 12B illustrates the end effector 150 in a central position, and FIG. 12C illustrates the end effector 150 is a second position. To articulate the end effector 150 back and forth, the distal channel retainer 408 includes the first retainer pin 410 (as shown in FIG. 11B), and the first articulation rod 406A includes a first rod aperture 412 distally that engages the first retainer pin 410. Similarly, the distal channel retainer 408 includes the second retainer pin 411, and the second articulation rod 407A includes a second rod aperture 413 distally that engages the second retainer pin 411. As the first articulation rod 406A translates proximally (as shown by the arrow in FIG. 12C), the first articulation rod 406A pulls the first retainer pin 410 proximally and thus articulates the distal channel retainer 408 about the articulation pivot point 466 in one direction. The second articulation rod 407A can translate distally to permit the channel retainer 408 to articulate about the articulation pivot point 466. Similarly, as the second articulation rod 407A translates proximally (as shown by the arrow in FIG. 12A), the second articulation rod 407A pulls the second retainer pin 411 proximally and thus articulates the distal channel retainer 408 about the articulation pivot point 466 in the opposite direction. The first articulation rod 406A can translate distally to permit the channel retainer 408 to articulate about the articulation pivot point 466. The first articulation rod aperture 412 and the second articulation rod aperture 413 can each be oblong, as shown in FIG. 11B, to account for the translation of the first and second retainer pins 410, 411 laterally as the distal channel retainer 408 rotates, since the first articulation rod 406A and second articulation rod 407A moves only axially and is constrained to the shaft 604 within a rod groove 478. FIG. 10 shows a view of the rod groove 478 along the length of the shaft 604. Note that in other examples, the proximal and distal motions can be reversed. For example, the rotation illustrated in FIG. 12A can be accomplished by any one of distal movement of the first articulation rod 406A, proximal movement of the second articulation rod 407A or the coordinated movements of both articulation rods 406A, 407A. The same holds true for the entire articulation range of motion.

Figure 13A:
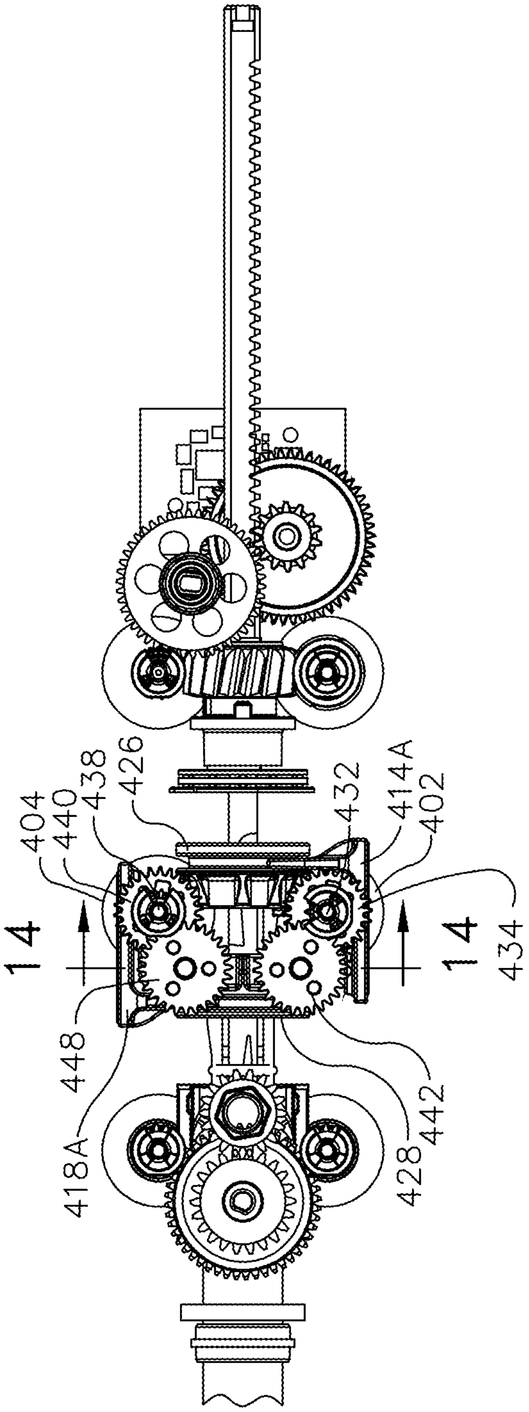
FIG. 13A is a detailed view of components of the articulation subsystem, according to aspects of the present disclosure.
Figure 13B:
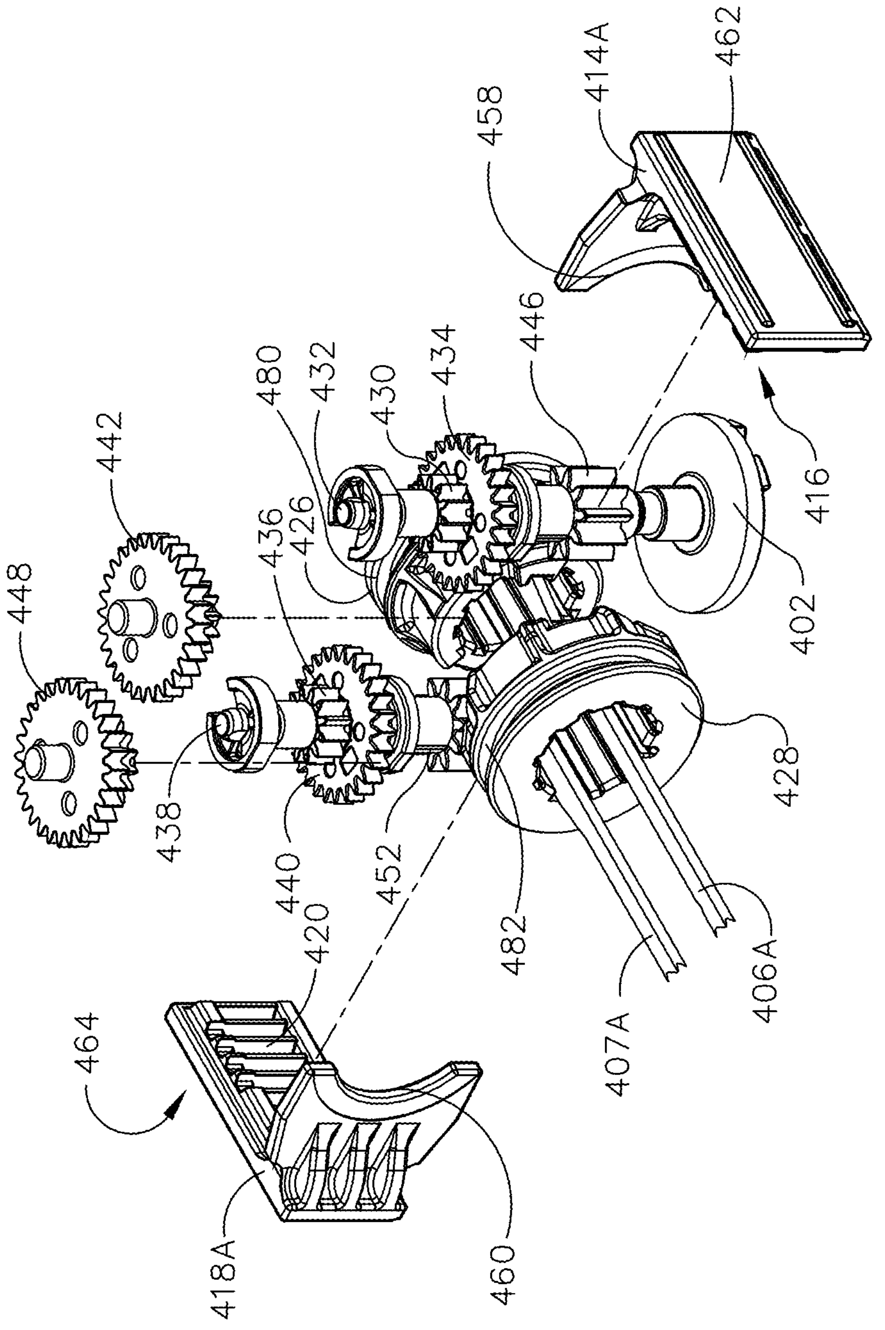
FIG. 13B is an exploded view of components of the articulation subsystem, according to aspects of the present disclosure.
Figure 14:
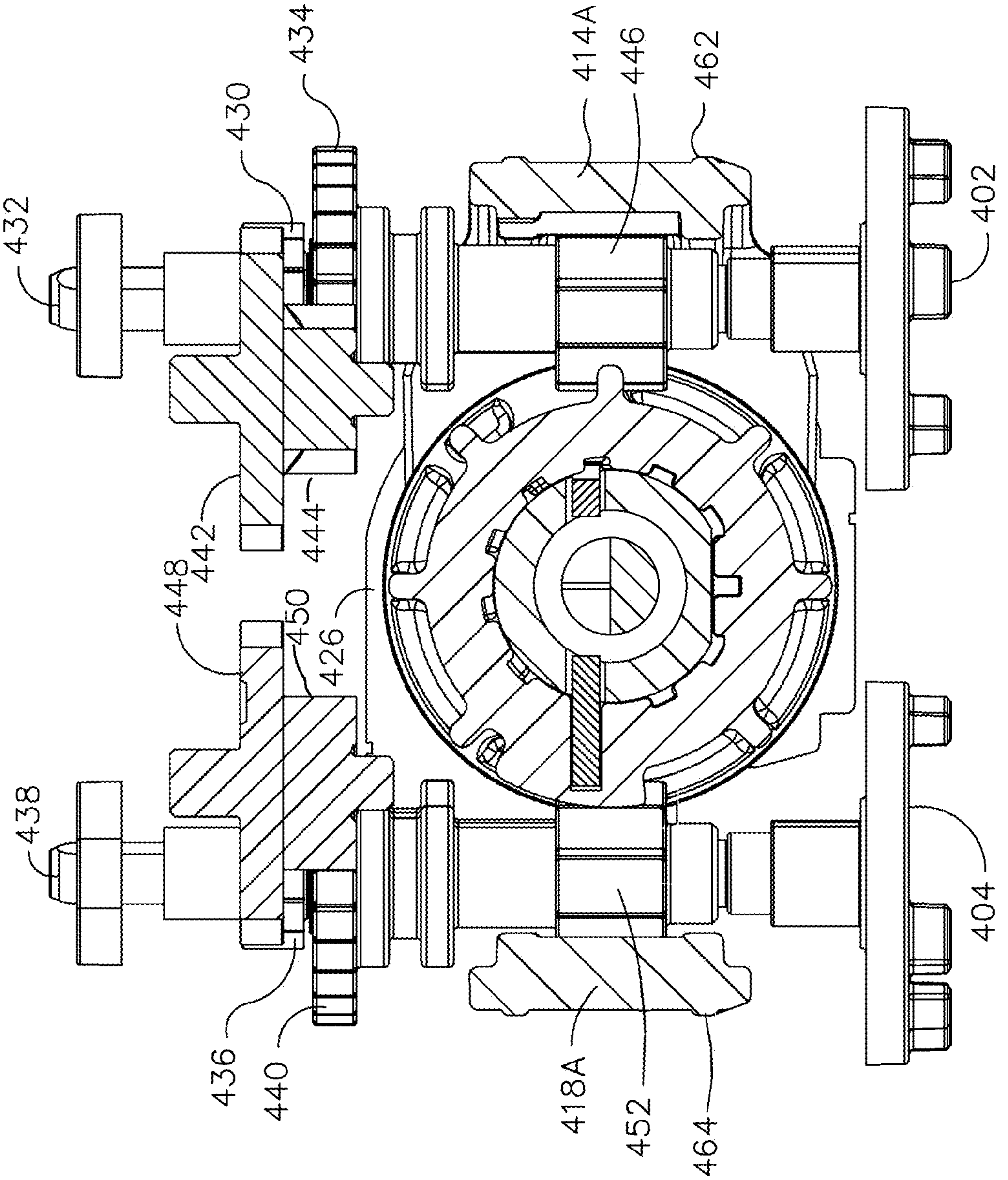
FIG. 14 is a cross-sectional view of the components of the articulation subsystem, according to aspects of the present disclosure.

Referring now to FIGS. 13A and 13B, which are a detailed view and an exploded of the proximal portions of the articulation subsystem 400, respectively. Additionally, FIG. 14 shows a cross-sectional view of the articulation subsystem 400 taken along line A-A of FIG. 13A. The articulation subsystem 400 includes features that accommodate the roll functions of the surgical instrument 100. As will be described in greater detail below with respect to the roll subsystem 600, the surgical instrument 100 includes a shaft 604 that can roll, i.e., rotate with respect to a longitudinal axis 474 of the surgical instrument 100, to allow a full range of articulation for the end effector 150. To elaborate, the shaft 604 can be directly connected to the end effector 150, and therefore the combination of rolling of the shaft 604 (via the roll subsystem 600) and articulating the end effector 150 (via the articulation subsystem 400) enables the end effector 150 to articulate with more degrees of freedom than simply left to right by pivoting the distal channel retainer 408. Access to the surgical site is thereby improved due to the combination of the articulation, roll, and insertion of the surgical instrument 100.

Figure 15A:
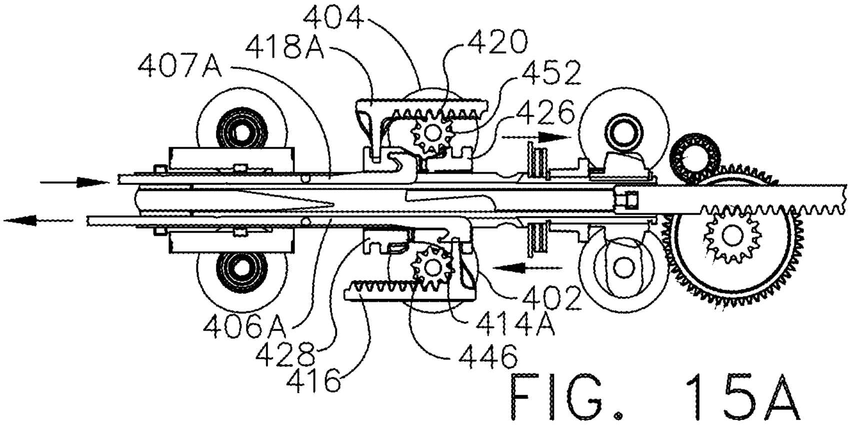
FIGS. 15A-15C show detail views of the articulation subsystem, according to aspects of the present disclosure.
Figure 15B:
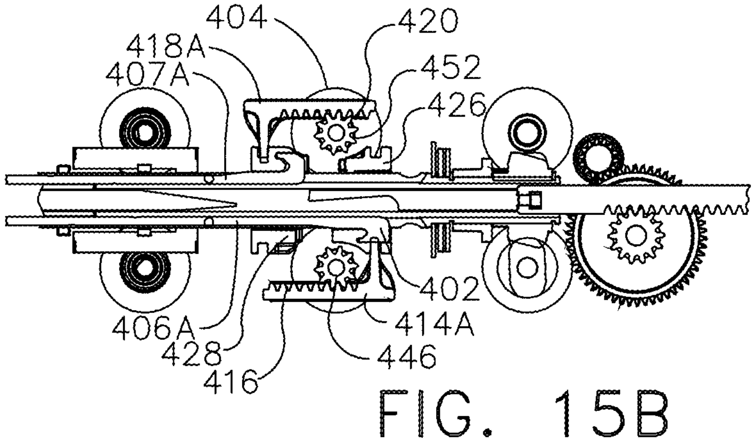
Figure 15C:
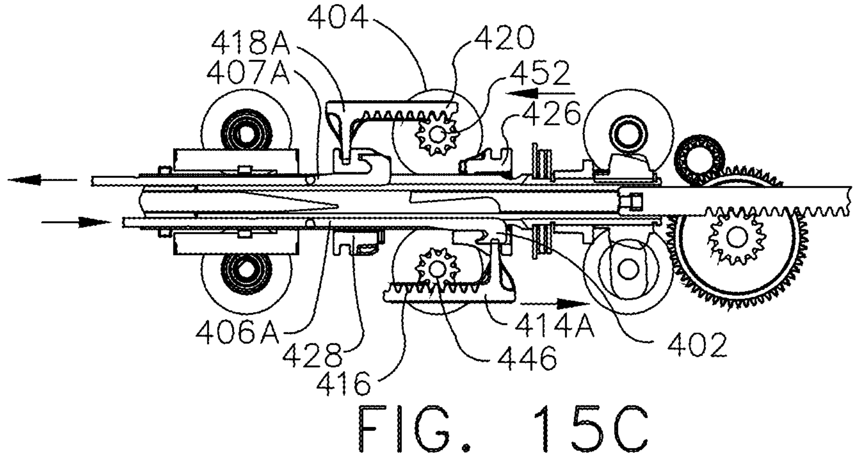

The first articulation rod 406A and the second articulation rod 407A each extend along the rotatable shaft 604, for example within the rod groove 478. To account for the ability of the first articulation rod 406A and the second articulation rod 407A to rotate with the shaft 604, the articulation subsystem 400 includes bushings (i.e., first articulation bushing 426 and second articulation bushing 428) that allow the rotatable robotic outputs to move the articulation subsystem 400 proximally and distally (for example to move the first articulation rod 406A and the second articulation rod 407A) along the shaft 604, while also allowing the shaft 604 to rotate within the articulation subsystem 400. The articulation subsystem 400 includes a first rack 414A that can be moved via a series of gearing by rotation of the first articulation input puck 402, the first articulation input puck 402 being engageable with a corresponding rotatable robotic output. The inside of the first rack 414A includes rack gearing 416 (as shown in FIGS. 15A, 15B, and 15C) that facilitates axial translation of the first rack 414A (e.g., distal and proximal within the outer housing 102 as indicated by the arrows in FIGS. 15A and 15C). The articulation subsystem 400 includes a second rack 418A that can be moved via a series of gearing by rotation of the second articulation input puck 404, the puck 404 being engageable with a corresponding rotatable robotic output. The inside of the second rack 418A includes rack gearing 420 (as shown in FIGS. 15A, 15B, and 15C) that enables axial translation of the second rack 418A (e.g., distal and proximal within the outer housing 102 as indicated by the arrows in FIGS. 15A and 15C).

To account for the rotation of the shaft 604, the articulation subsystem 400 includes a first articulation bushing 426 that is rotatable with the shaft 604 and is rotatably independent of the first rack 414A. In other words, the rolling of the shaft 604 will also roll the first articulation bushing 426, all while the first rack 414A remains rotationally stable within the outer housing 102. The first articulation bushing 426 can slide from a first position to a second position along a longitudinal axis 474 of the rotatable shaft 604, thereby moving the first articulation rod 406A proximally and distally. The first rack 414A includes a first housing track surface 462 (as shown in FIG. 14) that moves axially within a corresponding track in the outer housing 102, thereby enabling the first rack 414A to slide axially but not rotationally. The first housing track surface 462 and the first bushing bearing surface 458 can be at 90° with respect to each other. The articulation subsystem 400 includes a second articulation bushing 428 that is rotatable with the shaft 604 and is rotatably independent of the second rack 418A. In other words, the rolling of the shaft 604 will also roll the second articulation bushing 428, all while the second rack 418A remains rotationally stable within the outer housing 102. The second articulation bushing 428 can slide from a first position to a second position along the longitudinal axis 474 of the rotatable shaft 604, thereby moving the second articulation rod 407A proximally and distally. The second rack 418A includes a second housing track surface 464 (as shown in FIG. 14) that moves axially within a corresponding track in the outer housing 102, thereby enabling the second rack 418A to slide axially but not rotationally. The second housing track surface 464 and the second bushing bearing surface 460 can be at 90° with respect to each other.

The articulation subsystem 400 includes a first articulation drive shaft 432 extending from the first articulation input puck 402 and including a first drive gear 430 that can be keyed to the first articulation drive shaft 432. Rotation of the first articulation input puck 402 by the corresponding robotic output can therefore rotate the first drive gear 430. The articulation subsystem 400 includes a first rack gear 434, which can in some instances be a hollow tube gear that slides over the first articulation drive shaft 432, thereby providing a mechanical advantage to the system while also conserving space within the outer housing 102. The first rack gear 434 can be rotatably coupled to the first articulation drive shaft 432 by means of a first compound gear 442 that has stepped teeth 444, one portion of the stepped teeth 444 being engaged with the first drive gear 430, and the other portion of the stepped teeth 444 being engaged with the first rack gear 434. As such, rotation of the first articulation drive shaft 432 rotates the first drive gear 430, rotation of the first drive gear 430 rotates the first compound gear 442, and rotation of the first compound gear 442 rotates the first rack gear 434 that is surrounding the first articulation drive shaft 432. Further, the first rack gear 434 includes first rack gear teeth 446 that engage with the rack gearing 416 of the first rack 414A. Rotation of the first rack gear 434 therefore causes the first rack 414A to translate proximally and distally to move the first articulation bushing 426. With this configuration, rotation of the first input puck 402 in a clockwise direction (when viewed from a perspective showing the surface of the first input puck 402 that is configured to engage with the robotic arm 1100 (e.g., when viewing the outer-facing surface of first input puck 402)) can cause the first rack 414A to move proximally and rotation of the first puck 402 in a counter-clockwise direction can cause the first rack 414A to move distally.

Similarly, the articulation subsystem includes a second articulation drive shaft 438 extending from the second articulation input puck 404 and including a second drive gear 436. Rotation of the second articulation input puck 404 by the corresponding robotic output can therefore rotate the second drive gear 436. The articulation subsystem 400 includes a second rack gear 440, which can in some instances be a hollow tube gear that slides over the second articulation drive shaft 438. The second rack gear 440 can be rotatably coupled to the second articulation drive shaft 438 by means of a second compound gear 448 that has stepped teeth 450, one portion of the stepped teeth 450 being engaged with the second drive gear 436, and the other portion of the stepped teeth 450 being engaged with the second rack gear 440. As such, rotation of the second articulation drive shaft 438 rotates the second drive gear 436, rotation of the second drive gear 436 rotates the second compound gear 448, and rotation of the second compound gear 448 rotates the second rack gear 440 that is surrounding the second articulation drive shaft 438. Further, the second rack gear 440 includes second rack gear teeth 452 that engage with the rack gearing 420 of the second rack 418A. Rotation of the second rack gear 440 therefore causes the second rack 418A to translate proximally and distally to move the second articulation bushing 428. With this configuration, rotation of the second input puck 404 in a clockwise direction (when viewed from a perspective showing the surface of the second input puck 404 that is configured to engage with the robotic arm 1100 (e.g., when viewing the outer-facing surface of second input puck 404)) can cause the second rack 418A to move distally and rotation of the second input puck 404 in a counter-clockwise direction can cause the second rack 418A to move proximally.

Referring again to the articulation bushings and racks, the first rack 414A can engage with the first articulation bushing 426 in a manner that enables proximal or distal movement of the first articulation bushing 426, while the first articulation bushing 426 remains able to rotate with the shaft 604. The first rack 414A includes a first bushing bearing surface 458 that abuts the first articulation bushing 426. The first articulation bushing 426 includes a first rack groove 480 around the perimeter of the bushing in which the first bushing bearing surface 458 extends. As the first articulation bushing 426 rotates, the first bushing bearing surface 458 can track through the first rack groove 480. As such, the first bushing bearing surface 458 can be semicircular. Similarly, the second rack 418A can engage with the second articulation bushing 428 in a manner that enables proximal or distal movement of the second articulation bushing 428, while the second articulation bushing 428 remains able to rotate with the shaft 604. The second rack 418A includes a second bushing bearing surface 460 that abuts the second articulation bushing 428. The second articulation bushing 428 includes a second rack groove 482 around the perimeter of the bushing in which the second bushing bearing surface 460 extends. As the second articulation bushing 428 rotates, the second bushing bearing surface 460 can track through the second rack groove 482. As such, the second bushing bearing surface 460 can be semicircular.

Referring now to FIGS. 15A, 15B, and 15C which show the actuation of the articulation subsystem 400 by movement of the first rack 414A and the second rack 418A. FIG. 15B shows an articulation subsystem 400 at a neutral, e.g., 0° state, of articulation. To move the first articulation bushing 426, the first rack gear 434 can rotate in a first angular direction, and the first rack gear teeth 446 move through the first rack gearing 416 of the first rack 414A. As shown in FIG. 15A, when the first rack gear 434 rotates and causes the first rack 414A to move proximally, the first articulation rod hook 405 is pulled proximally and causes the first articulation rod 406A to be pulled proximally. The second articulation rod 407A can be let out by the robotic arm to allow the end effector 150 to move in a first direction, in this example to the right (as shown in FIG. 12A).

FIG. 15C shows where the first rack 414A has moved distally and the second rack 418A has been moved proximally. Movement of the second rack 418A proximally causes the second articulation bushing 428 to translate proximally along the longitudinal axis 474 of the shaft 604. In turn, the second articulation rod 407A will translate proximally, thereby pivoting the distal channel retainer 408 such that the end effector 150 pivots in a second direction, in this example to the left (as shown in FIG. 12C (the end effector in FIGS. 12A-12C being rotated 180 degrees compared to FIGS. 15A-15C)). The first articulation rod 406A can be let out by the robotic arm to allow the end effector 150 to move in the second direction. In this example, the first articulation rod 406A and the second articulation rod 407A only cause actuation of the end effector 150 when caused to move proximally, thereby pulling the distal channel retainer 408 to pivot from left to right. In other words, the first articulation rod 406A and the second articulation rod 407A only cause the end effector 150 actuate when pulled in this example. In other examples, the first articulation rod 406A and the second articulation rod 407A can be configured to work together in a push/pull relationship. For example, as one of the first articulation rod 406A and the second articulation rod 407A is pulled in a proximal direction, the other of the first articulation rod 406A and the second articulation rod 407A can be pushed in a distal direction, thereby increasing the force applied to cause the articulation. That is the first articulation input puck 402 and the second articulation input puck 404 can be used together to cause the articulation system to actuate, thereby increasing the force applied to the articulation subsystem 400 for articulating the end effector 150.

In some examples, the articulation subsystem 400 described herein can achieve at least 60° of articulation in either direction, for example±5°, ±10°, ±15°, ±20°, ±25°, ±30°, ±35°, ±40°, ±45°, ±50°, ±55°, and ±60°, or any intervening degree of articulation back and forth. It will be noted that the joint 160 shown in FIG. 12B that holds the end effector 150 to the shaft 604 is exposed for visualization. The joint 160 can be concealed by a flexible sheath 174 to alleviate pinch points. The joint 160 described herein can include multiple articulation links that connect the closure tube 212 to the closure ring 226. This linking system can be a boss/hole configuration that provides a pinned joint. The exterior closure system can consist of the closure tube 212 pushing distally forward on the two articulation links of the joint 160, which in turn push on the closure ring 226.

Turning now to FIGS. 16A, 16B, 16C, 16D, 16E and 16F, an alternative example articulation subsystem 400 is herein described. As shown, the articulation subsystem 400 can include a first inboard rack 414B and a second inboard rack 418B. For example, the first inboard rack 414B can be positioned at least partially between the first rack gear 434 and the rotatable shaft 604 and the second inboard rack 418B can be positioned at least partially between the second rack gear 440 and the rotatable shaft 604. In this way, the articulation subsystem 400 will have a more compact layout and the forces applied by the first inboard rack 414B and the second inboard rack 418B can be distributed closer to the longitudinal axis, thereby reducing torque forces on the first inboard rack 414B and the second inboard rack 418B.

The first inboard rack 414B and the second inboard rack 418B can each be pushed or pulled together in a push/pull relationship. For example, if the first inboard rack 414B and the second inboard rack 418B are moved axially toward each other, the end effector 150 will articulate in a first direction (e.g., to the right). If the first inboard rack 414B and the second inboard rack 418B are moved axially away from each other, the end effector will articulate in a second direction (e.g., to the left). In this way, forces from the first articulation input puck 402 and the second articulation input puck 404 can work together to cause the end effector 150 to articulate in a first or a second direction.

Figure 16A:
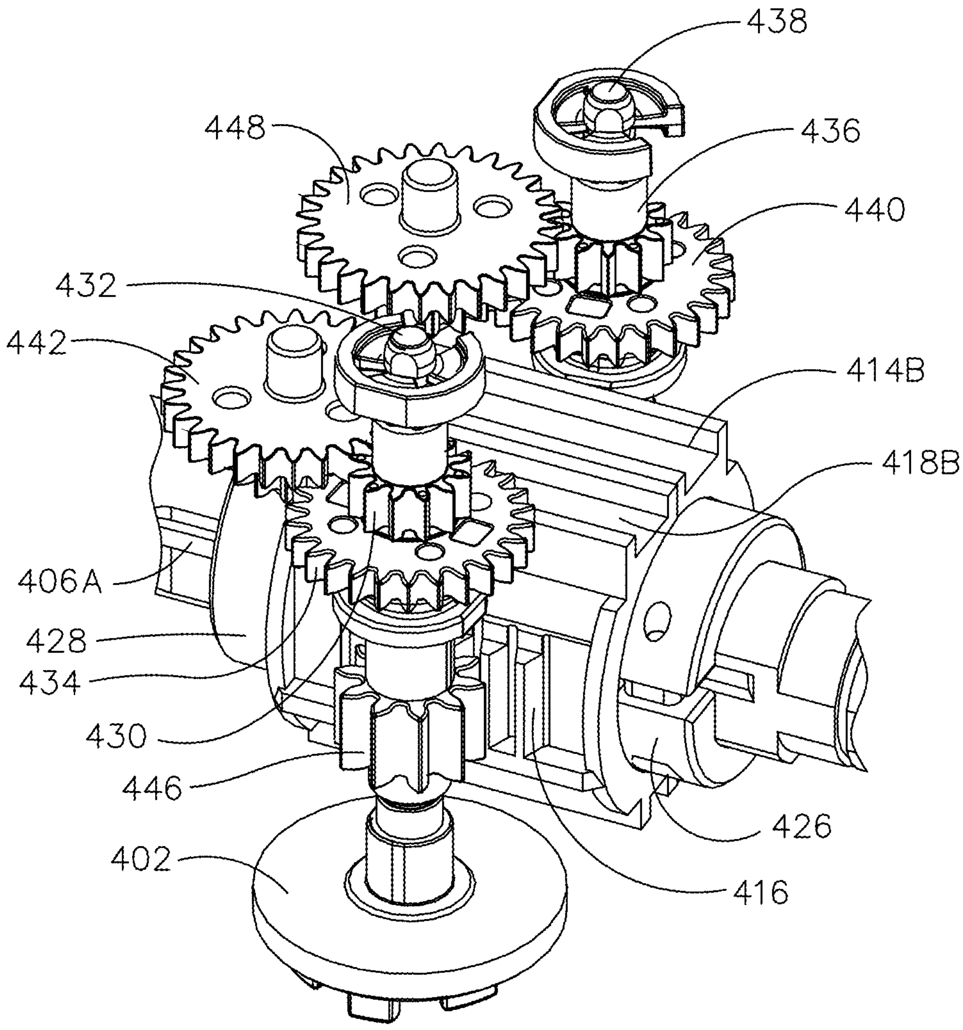
FIG. 16A is a detail view of an alternate articulation subsystem, according to aspects of the present disclosure.
Figure 16B:
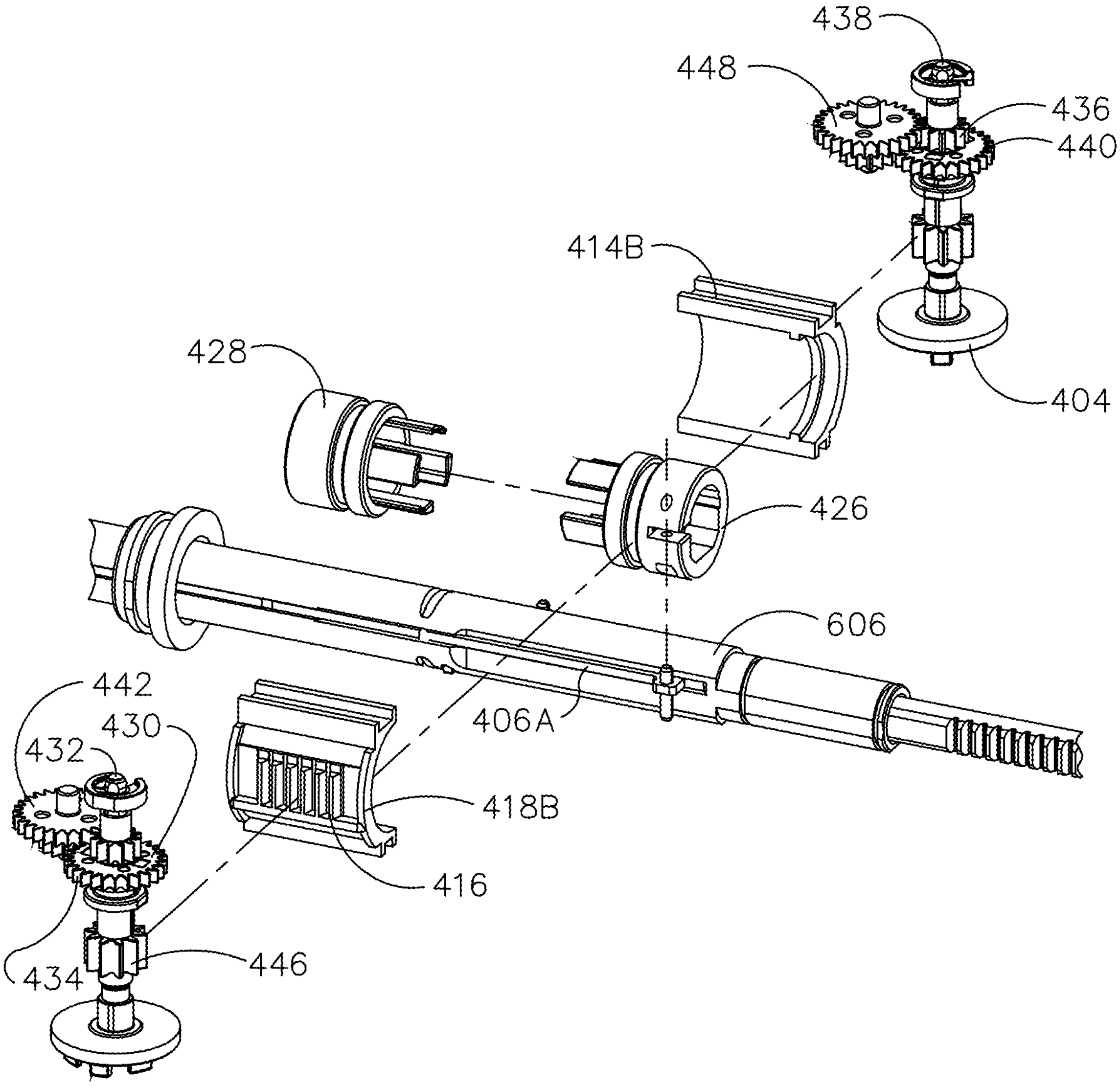
FIG. 16B is an exploded view of the alternate articulation subsystem of FIG. 16A, according to aspects of the present disclosure.
Figure 16C:
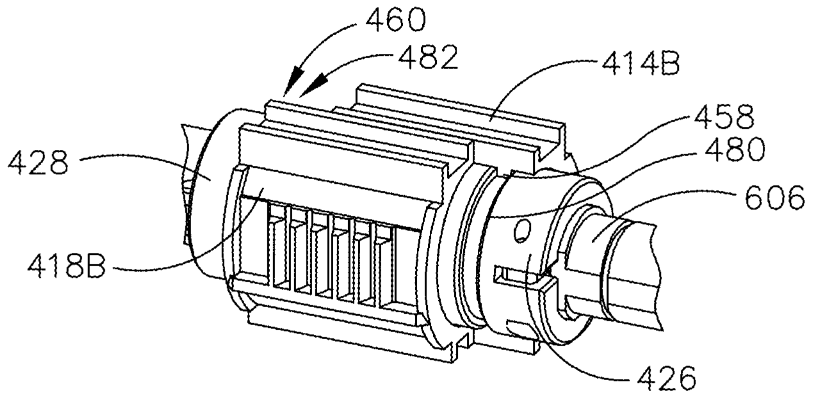
FIG. 16C is a detail view of articulation racks of the alternate articulation subsystem of FIG. 16A, according to aspects of the present disclosure.
Figure 16D:
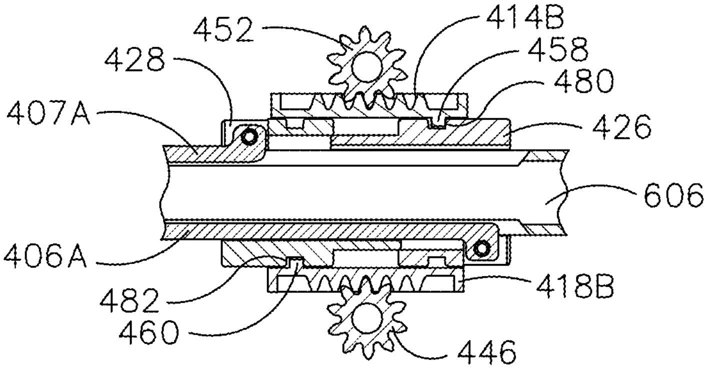
FIG. 16D is a section view of the alternate articulation subsystem taken horizontally along the longitudinal axis, according to aspects of the present disclosure.

Similar to the first rack 414A and the second rack 418, the first inboard rack 414B and the second inboard rack 418B can be configured to cause the first articulation rod 406A and the second articulation rod 407A to move proximally and distally via a first articulation bushing 426 and a second articulation bushing 428. Because the first inboard rack 414B and the second inboard rack 418B are positioned at least partially around the rotatable shaft 604 adjacent the first articulation bushing 426 and the second articulation bushing 428, the first inboard rack 414B and the second inboard rack 418B can push on the first articulation bushing 426 and the second articulation bushing 428, respectively, without the need for a portion of the racks to extend outwardly and engage with the bushings. As shown in FIGS. 16C and 16D, similar to the first rack 414 and the first articulation bushing 426, the first inboard rack 414B includes a first bushing bearing surface 458 that engages with a first rack groove 480. Similarly, the second inboard rack 418B includes a second bushing bearing surface 460 that engages with the second rack groove 482. In this way, the first inboard rack 414B and the second inboard rack 418B can be configured to move the first articulation bushing 426 and the second articulation bushing 428 proximally and distally but remain rotationally independent of the first articulation bushing 426 and a second articulation bushing 428.

Figure 16E:
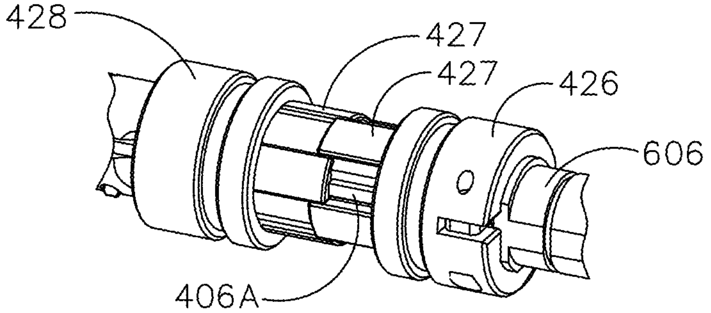
FIG. 16E is a detail view of articulation bushings of the alternate articulation subsystem, according to aspects of the present disclosure.

As shown in FIG. 16E, the first articulation bushing 426 and the second articulation bushing 428 can each include one or more bushing extensions 427 that protrude from the first articulation bushing 426 and the second articulation bushing 428 in a direction along the longitudinal axis. In this way, the bushing extensions 427 can help to prevent the first articulation bushing 426 and the second articulation bushing 428 from binding when being pushed or pulled proximally or distally.

Figure 16F:
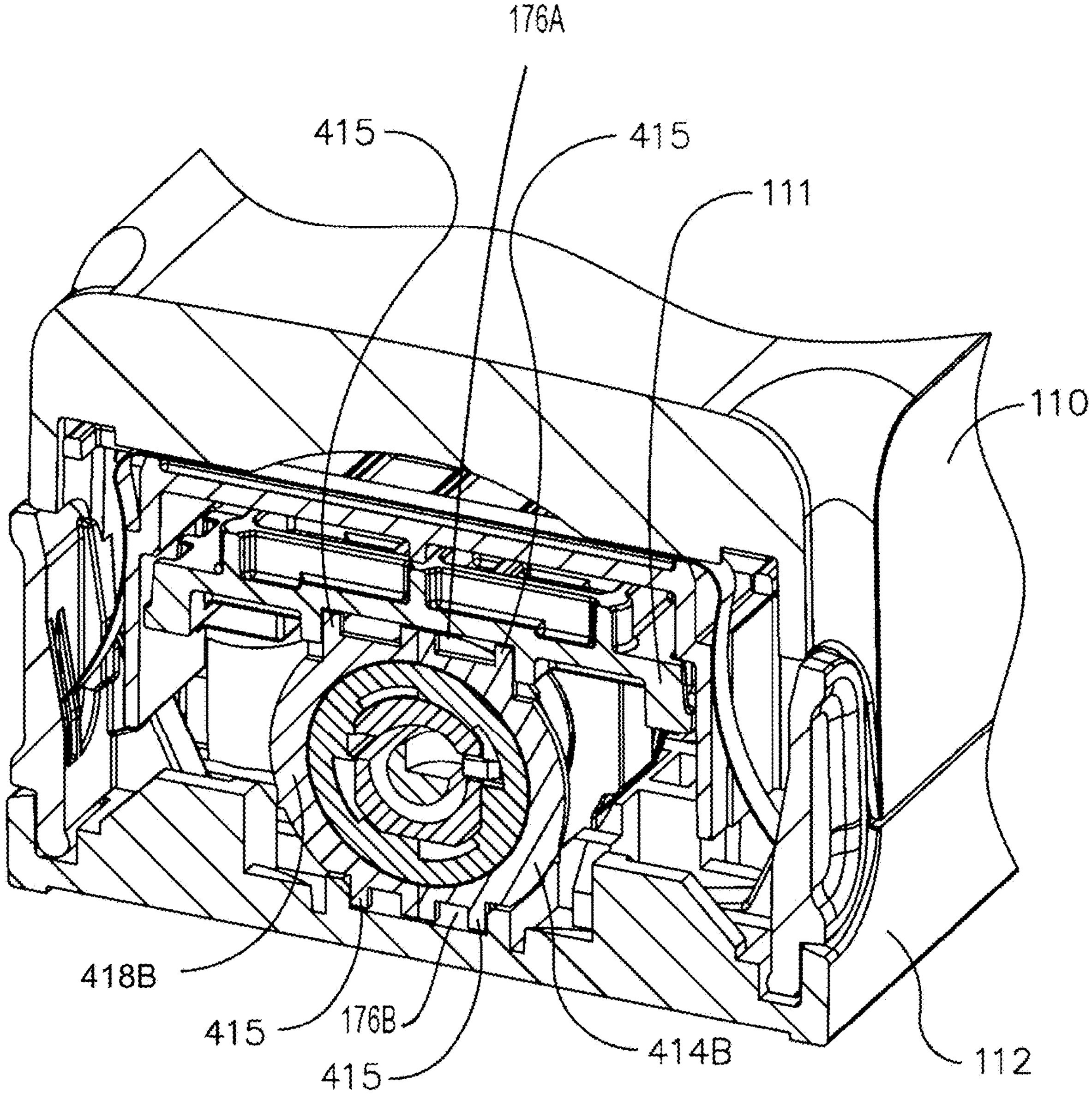
FIG. 16F is a detail view of the alternate articulation subsystem contacting a housing of the surgical instrument, according to aspects of the present disclosure.

As shown in FIG. 16F, the first inboard rack 414B and the second inboard rack 418B can each have a housing track surface 415 that moves axially within a corresponding track 176B in the first portion 112 of the housing 102 and a track 176A of the intermediate housing 111, thereby enabling the first inboard rack 414B to slide axially but not rotationally. In other words, the housing track surfaces 415 of the first inboard rack 414B and the second inboard rack 418B are configured to slide along the tracks 176A, 17B of the first portion 112 of the housing 102 and the intermediate housing 111 disposed in the housing 102. In this way, any rotational force applied to the first inboard rack 414B and the second inboard rack 418B by the roll subsystem 600 will not cause the first inboard rack 414B and the second inboard rack 418B to rotate within the housing 102.

Turning now to FIGS. 17A, 17B, 17C, 17D, 17E, 17F, and 17G, yet another alternate example of the articulation subsystem 400 will be shown and described. As shown, the articulation subsystem 400 can include a single inboard rack 414C that extends around the rotatable shaft 604. The first tube drive teeth 446 can engage with the single inboard rack 414C on a first side and the second tube drive teeth 452 can engage with the single inboard rack 414C on a second side. That is, the first tube drive teeth 446 and the second tube drive teeth 452 can engage the singe inboard rack 414C together. The single inboard rack 414C can be engaged with a single articulation bushing 429 that is coupled to a single articulation rod 403. That is, compared to the previous examples shown and described herein, the example articulation subsystem 400 shown in FIGS. 17A-17G can include a single articulation rod 403 that can be both pulled and pushed by a single articulation bushing 429 and a single inboard rack 414C.

Figure 17A:
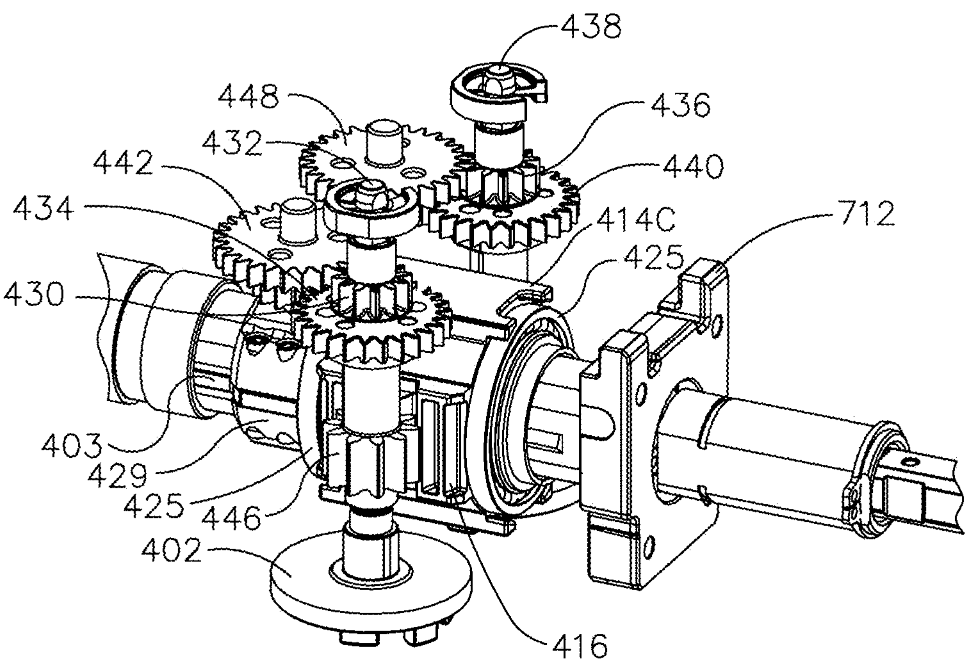
FIG. 17A is a detail view of another alternative articulation subsystem, according to aspects of the present disclosure.
Figure 17B:
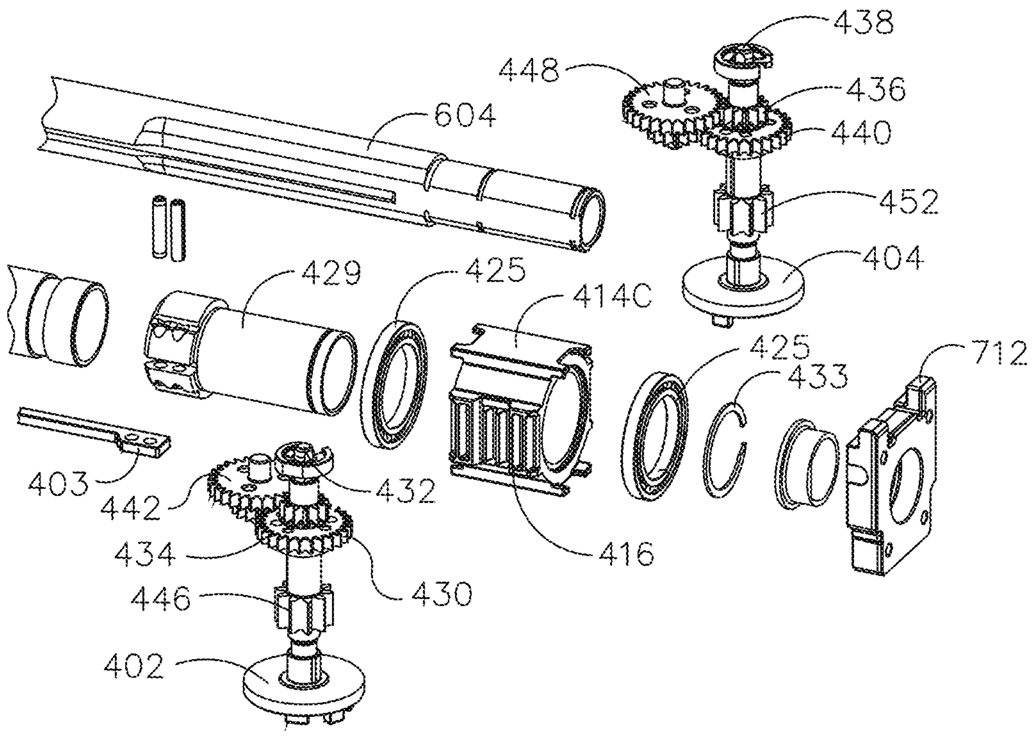
FIG. 17B is an exploded view of the other alternative articulation subsystem of FIG. 17A, according to aspects of the present disclosure.
Figure 17C:
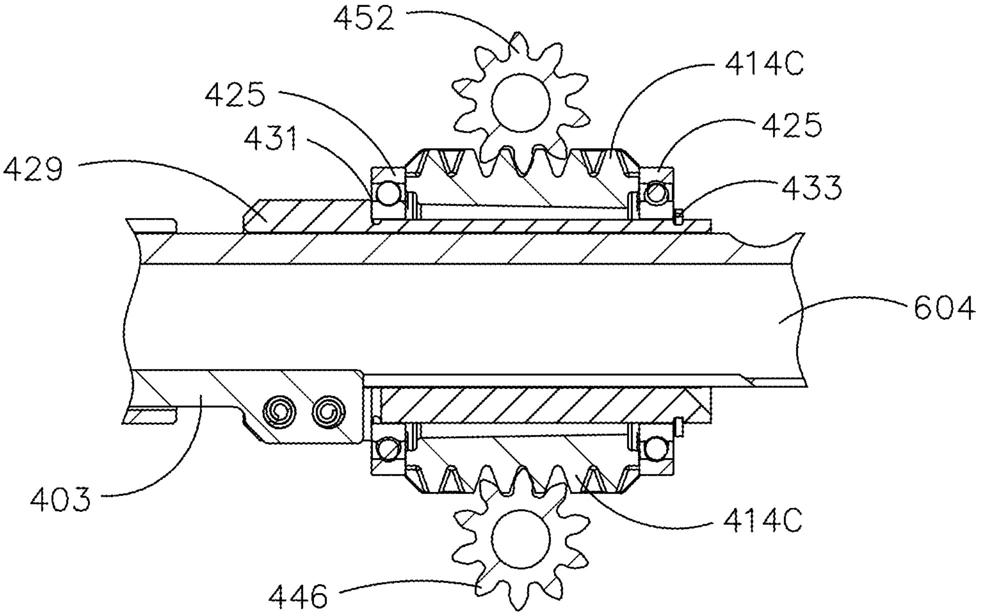
FIG. 17C is a section view of the other alternative articulation subsystem of FIG. 17A taken horizontally along the longitudinal axis, according to aspects of the present disclosure.
Figure 17D:
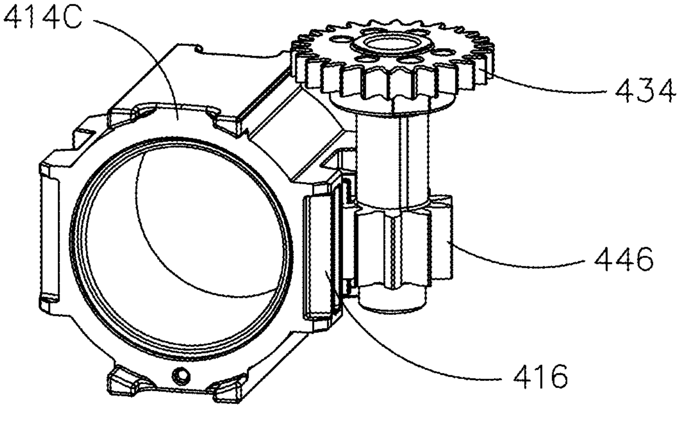
FIG. 17D is a detail view of an articulation rack and drive teeth of the other alternative articulation subsystem, according to aspects of the present disclosure.
Figure 17E:
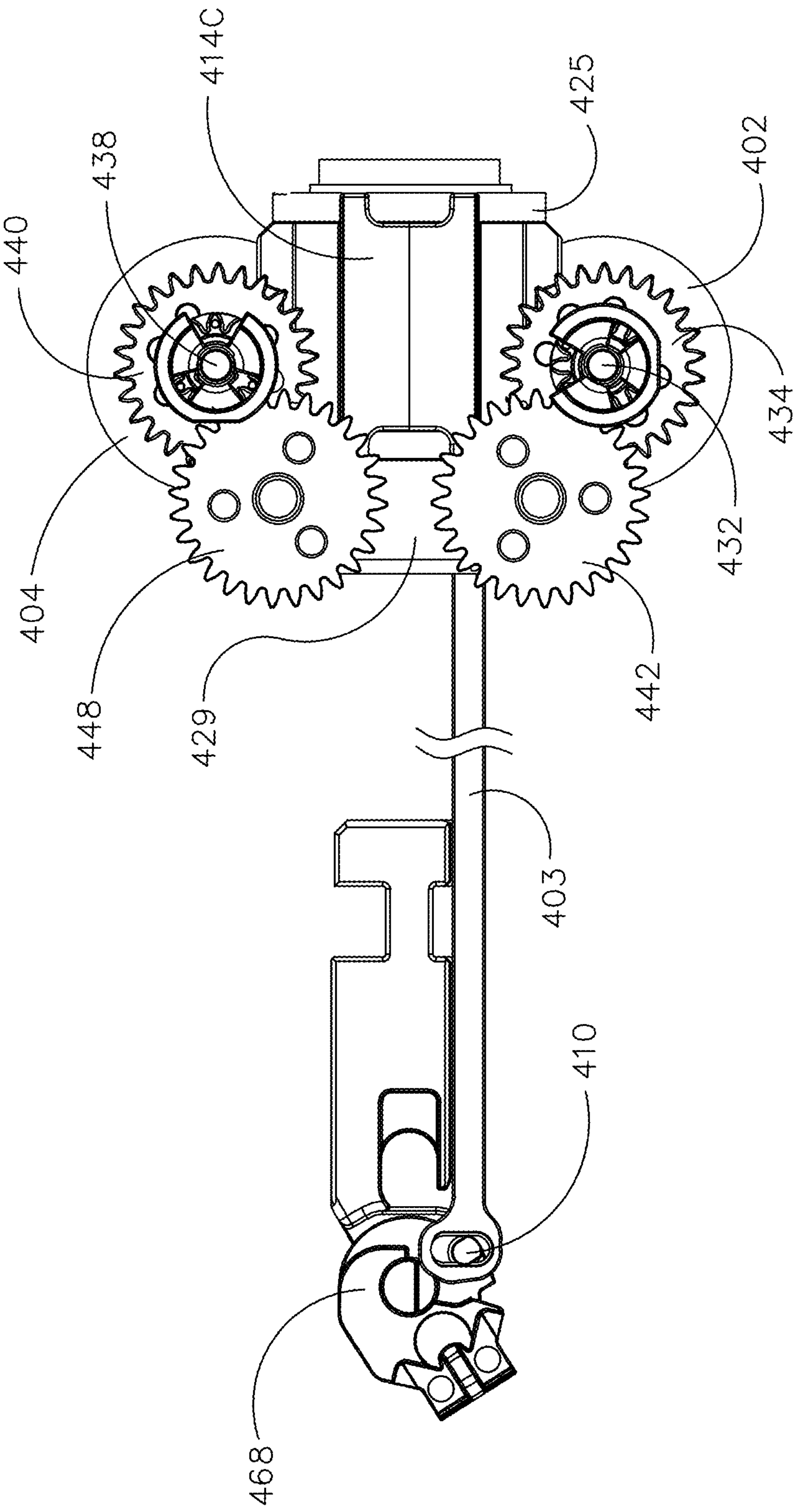
FIG. 17E is a top perspective view of the other alternative articulation subsystem of FIG. 17A, according to aspects of the present disclosure.

As shown in FIG. 17C, the single inboard rack 414C is separated from the single articulation bushing 429 by one or more bearings 425. The a first bearing 425 is constrained distally by a flange 431 and a second bearing 425 is constrained proximally by a locking ring 433. Constrained as such, movement of the single inboard rack 414C causes the single articulation bushing 420 to move axially. By including the bearings 425, the single inboard rack 414C can be rotationally independent of the single articulation bushing 429 but still be configured to cause the single articulation bushing 429 (and, consequently, the single articulation rod 403) to translate proximally and distally. Furthermore, because the first tube drive teeth 446 and the second tube drive teeth 452 engage the single inboard rack 414C together, it will be appreciated that forces from the first articulation input puck 402 and the second articulation input puck 404 can work together to cause the end effector 150 to translate in a first and in a second direction.

Figure 17F:
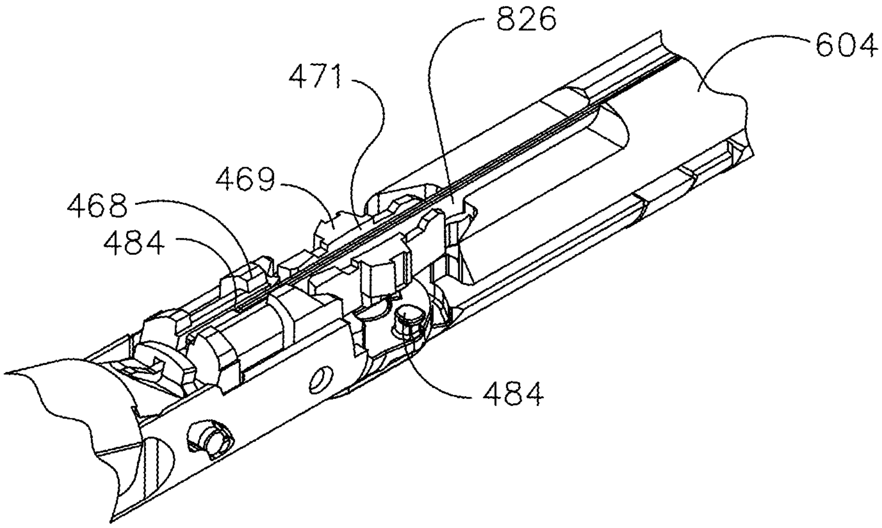
FIGS. 17F and 17G are detail views of an articulation joint of the articulation subsystem, according to aspects of the present disclosure.
Figure 17G:
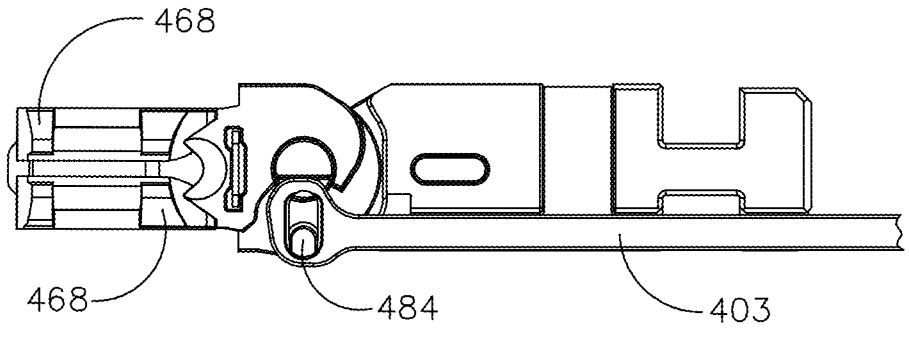

Turning now to FIGS. 17F and 17G, the articulation subsystem 400 can include a knife guide 469 that can be positioned between the attachment end 468 and the proximal end of the shaft 604. The knife guide 469 can include a band slot 471 similar to the band slot 484 of the attachment end 468 that can help to guide the bands 826 that translate proximally and distally. The knife guide 469 can help to prevent the bands 826 from buckling, twisting, or otherwise becoming bound when translating proximally or distally, thereby helping to ensure the knife 166 can also more proximally and distally.

As shown in FIGS. 17F and 17G, the articulation subsystem 400 can include an articulation rod post 484 that can receive the single articulation rod 403, The articulation rod post 484 can couple the single articulation rod 403 to the attachment end 468 to cause the end effector 150 to articulate left and right when the single articulation rod 403 is moved proximally and distally.

Roll Subsystem

Figure 18A:
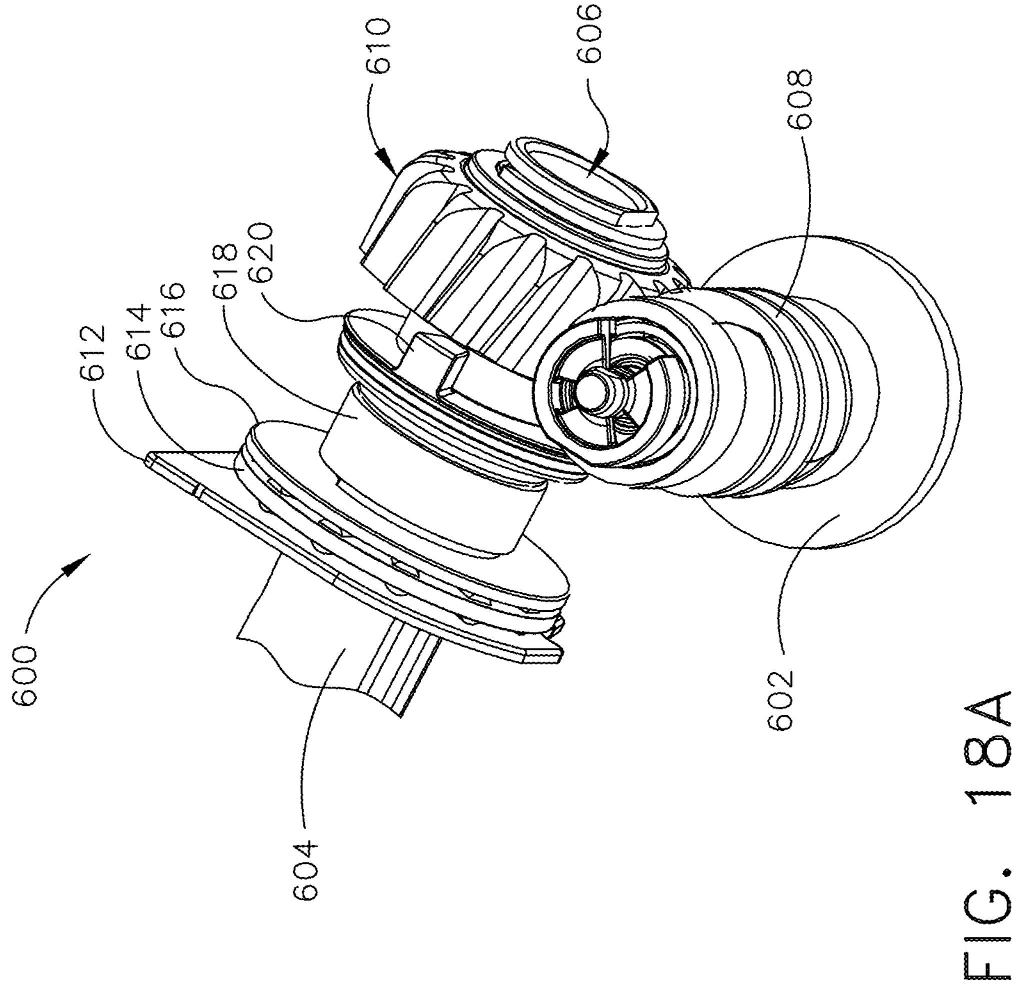
FIG. 18A is a detail view of components of a roll subsystem, according to aspects of the present disclosure.
Figure 18B:
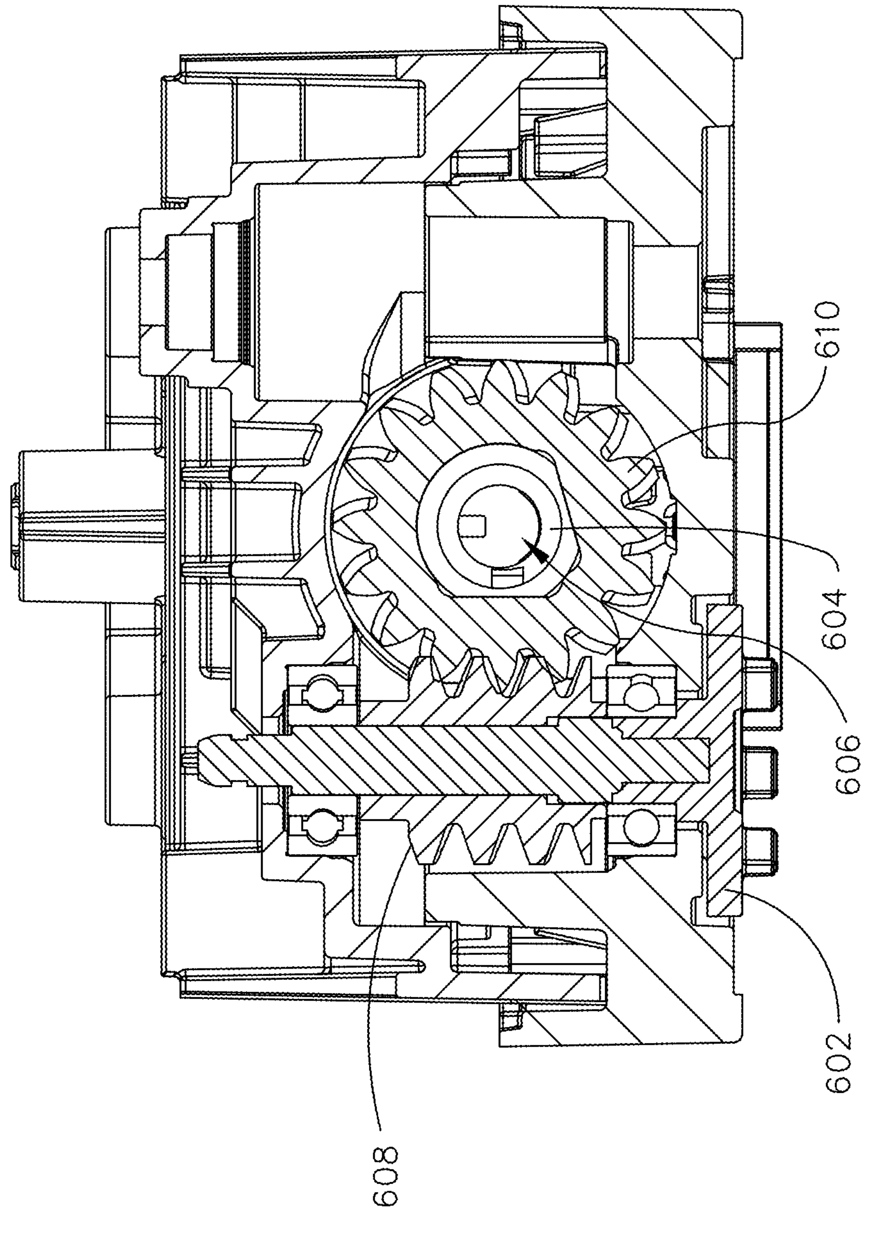
FIG. 18B is a cross-sectional view of components of the roll subsystem, according to aspects of the present disclosure.

The surgical instrument 100 includes a roll subsystem 600. Detailed views of the proximal portions of an example roll subsystem 600 are provided in FIGS. 18A, 18B, 18C, 18D, and 18E. Referring specifically to FIGS. 18A and 18B, the roll subsystem 600 includes a series of gears that allow the shaft 604 to rotate distally along a longitudinal axis 474 of the surgical instrument 100. The shaft 604 can be directly connected to the end effector 150, and therefore rolling of the shaft 604 enables the end effector 150 to roll a single articulation plane to any orthogonal position. The shaft 604 includes a shaft lumen 606 extending therethrough, and distal portions of a transection subsystem 800 extend through the shaft lumen 606. The transection subsystem 800 is described in greater detail below.

The roll subsystem 600 includes a roll input puck 602 that is engageable with a corresponding rotatable robotic output. The roll input puck 602 can be rotationally engaged with a worm gear 608 extending therefrom, such that rotation of the roll input puck 602 turns the worm gear 608 either clockwise or counter-clockwise. Since the roll input puck 602 is positioned perpendicular to the length of the surgical instrument 100, and therefore perpendicular to the shaft 604, the roll subsystem 600 includes a worm follower 610 that is engaged with the worm gear 608. The worm follower 610 can be coupled to the shaft 604, allowing rotation of the shaft 604. To keep the worm follower 610 positioned at the correct location relative to the worm gear 608, the roll subsystem 600 includes a stabilization plate 612 that surrounds the shaft 604 distal to the worm follower 610. The stabilization plate 612 can be positioned within a corresponding slot within the outer housing 102 to prevent the stabilization plate 612 from sliding axially along the shaft 604, while also providing the shaft 604 lateral alignment within the housing 102. The roll subsystem 600 can also include a roll bearing 614 and a roll bearing plate 616, the roll bearing 614 being positioned between the stabilization plate 612 and the roll bearing plate 616.

In some examples, the roll subsystem 600 includes a roll stop bushing 618 engaged with the rotatable shaft 604. The roll stop bushing 618 can be coupled to the worm follower 610 and/or shaft 604 and provide feedback on positioning of the rotatable shaft 604. For example, the roll stop bushing 618 includes a stop 620 positioned thereon that can contact a housing tab 626 positioned on the outer housing 102. The roll subsystem 600 can roll the shaft 604 to a first position where the roll stop bushing 618 contacts the housing tab 626 at a first side, and then roll the shaft 604 to a second position where the roll stop bushing 618 contacts the housing tab 626 at a second, opposite side. The robotic output that actuates the roll subsystem 600 can use the hard stops at the housing tab 626 to determine a baseline, or 0°, rotation for the shaft 604. This example can provide the shaft 604 greater than 300° of rotation, for example greater than 305°, greater than 310°, greater than 315°, greater than 320°, greater than 325°, greater than 330°, greater than 335°, greater than 340°, greater than 345°, greater than 350°, greater than 355° of rotation, or more.

In some examples, the roll subsystem 600 does not include a housing tab 626 and allows the roll subsystem 600 to continue to roll indefinitely. In this configuration, the control device 1110, described in greater detail herein, can be programmed to determine a home position and can be configured to track and accurately determine the position of the roll subsystem 600 and/or the end effector 150 at any given point of rotation.

Figure 18C:
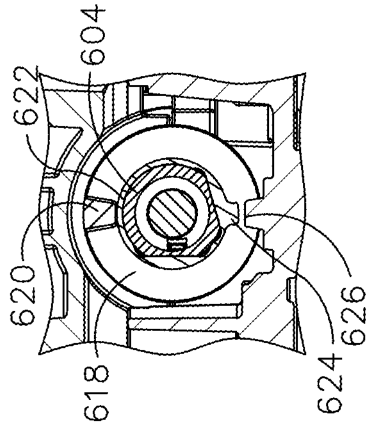
FIGS. 18C, 18D, and 18E are end views of bushings for a roll system, according to aspects of the present disclosure.
Figure 18D:
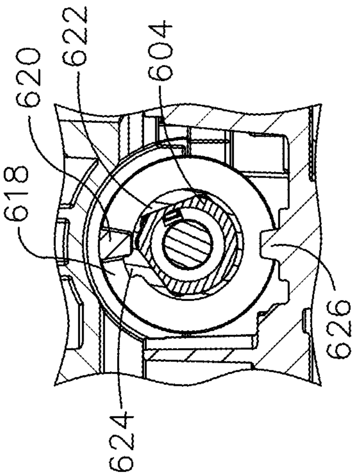
Figure 18E:
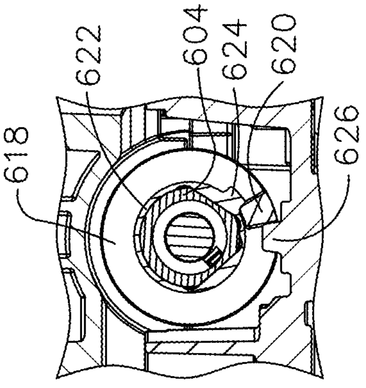

In some examples, the roll subsystem 600 can also include a follower bushing 622 (as shown in FIGS. 18C, 18D, and 18E) having a follower bushing stop 624 extending therefrom. In this example, the follower bushing 622 can be positioned between the shaft 604 and the roll stop bushing 618. The shaft 604 and follower bushing 622 can be directly coupled to each other, and the roll stop bushing 618 and the follower bushing 622 can rotate relative to each other. The roll subsystem 600 can roll the shaft 604 to a first position where the roll stop bushing 618 contacts the housing tab 626, and the follower bushing 622 contacts the roll stop bushing 618 at a first side (see FIG. 18C). The roll subsystem 600 can then rotate the shaft 604 until the follower bushing 622 contacts the roll stop bushing 618 at the other side (see FIG. 18D), and then continue rotating by pushing the roll stop bushing 618 circumferentially until the roll stop bushing 618 contacts the housing tab 626 and the follower bushing 622 contacts the roll stop bushing 618 at a second, opposite side (see FIG. 18E). This example using the follower bushing 622 can provide a greater degree of rotation, for example greater than 360° of rotation, or in some instances about 320° of rotation in either direction (e.g., 640° in total). Referring briefly to FIG. 10, which shows distal portions of the roll subsystem 600, the view shows how the rod groove 478 of the shaft 604 can extend along the length of the shaft 604. The first articulation rod 406A can extend through the rod groove 478 of the shaft 604, and rotation of the shaft 604 by the roll subsystem 600 can therefore rotate the articulation rod 406A.

Figure 19B:
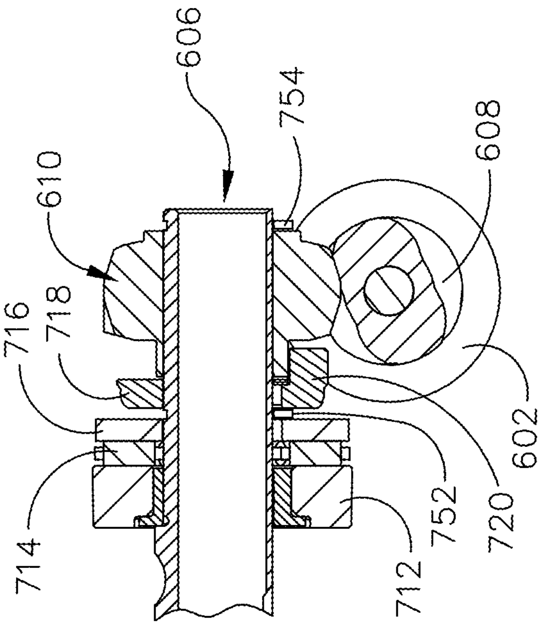
FIGS. 19A and 19B show alternative components of a roll subsystem, according to aspects of the present disclosure.
Figure 19A:
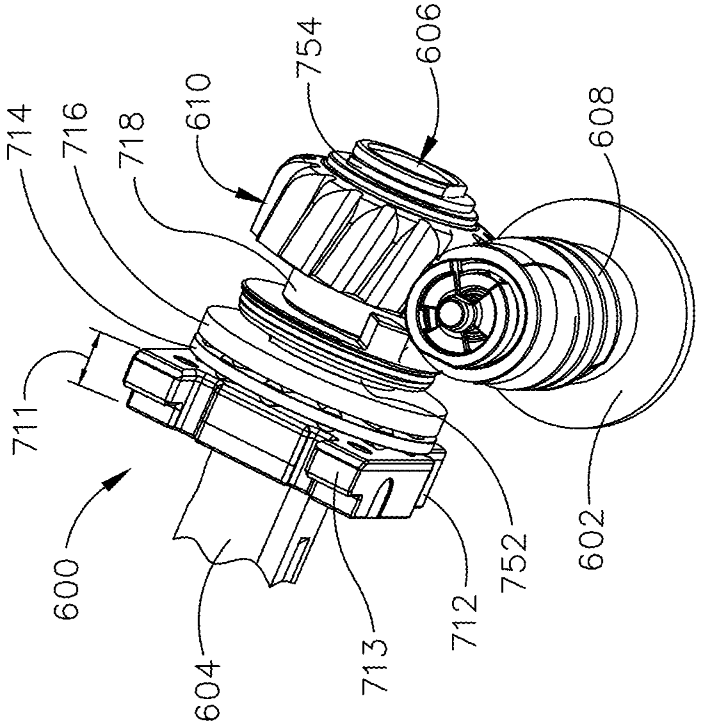

FIGS. 19A and 19B show alternative components of a roll subsystem 600 to the one shown in FIGS. 18A-18E, according to aspects of the present disclosure. FIG. 19A is a perspective view of the components of the roll subsystem 600. In the embodiment shown, the stabilization plate 612 shown in FIG. 26 has been replaced with a thicker thrust block 712. The thrust block 712 is positioned near the proximal end of the shaft 604 so as to counteract axial forces on the shaft 604 caused by distal movement of the closure tube 212 (see FIG. 1). Providing a more robust thrust block 712, including a thickness 711 greater than 1.0 cm, or greater than 1.5 cm, can provide better loading scenarios (to stop deflection) and can better share the load with the housing 102. The thrust block 712 includes supports 713 that engage with a buttress 178, such as the buttress 178 shown in FIG. 19I. As shown in FIG. 19I, the buttress 178 sits within the housing 102 and distributes loads applied to the buttress 178 from the thrust block 712 (as well as other components) to the housing 102. FIG. 19A shows additional components that can be included in the alternative design, including a roll bearing 714, which can be substantially similar to the roll bearing 614 in 18A, and a roll bearing plate 716, which can be substantially similar to the roll bearing plate 616 in FIG. 18A (in FIG. 19A, the bearing plate 716 is thicker than the roll bearing plate 616 to further add to the robustness and load sharing at this component). FIG. 19A also shows a roll stop bushing 718, which can be substantially similar to roll stop bushing 618. FIG. 19B is a top, cross-sectional view of the components of the roll subsystem 600. The roll subsystem 600 includes a first locking ring 752 and a second locking ring 754. The locking rings 752, 754 can be positioned such that they secure the worm follower 610 and the roll stop bushing 718 together. The stop 730 of the roll stop bushing 718 is also shown; the stop 720 can be substantially similar to the stop 620 described above.

Figure 19C:
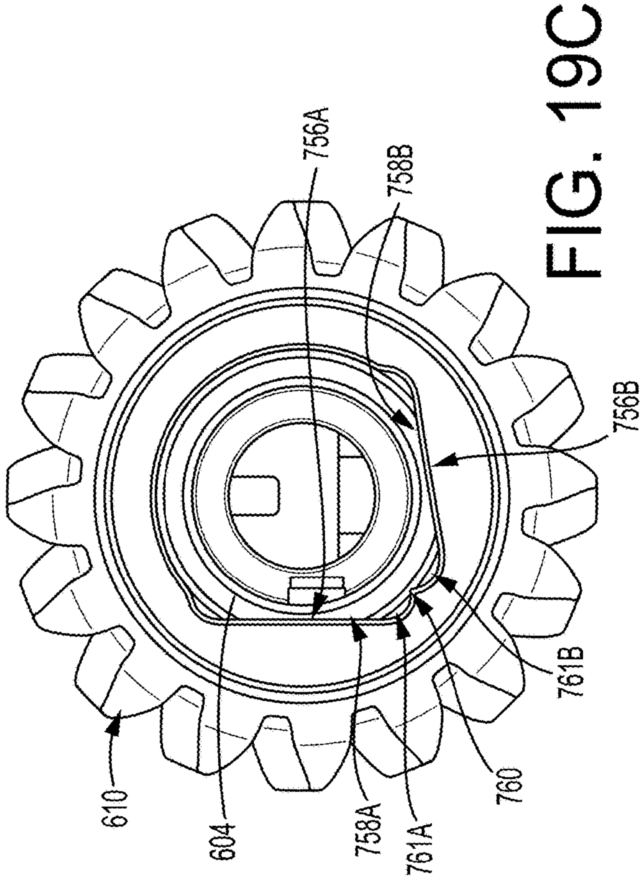
FIGS. 19C-19F provide examples of anti-backlash features for a worm follower engaged with a rotatable shaft, according to aspects of the present disclosure.

Referring to FIG. 19C for reference, as shown, the inside of the worm follower 610 may not be entirely round and, similarly, the outside surface of the shaft 604 may not be entirely round. Instead, the worm follower 610 and the shaft 604 can have corresponding anti-backlash features. It is desirable to reduce backlash in the gearing of a surgical instrument 100 to improve accuracy and to ensure proper calibration. For instance, a robot can home and/or calibrate roll by rolling the shaft 604 from one mechanical calibration position to another mechanical calibration position (see FIGS. 18C-18E for a discussion of rotational constraints for the roll subsystem 600). Therefore, backlash reduction can help to ensure accurate calibration. The implementations shown in FIGS. 19C-19F provide examples of such anti-backlash features.

FIG. 19C is a detailed view of the worm follower 610. Here, the inside area of the worm follower 610 (i.e., the portion engaged with the shaft 604) includes one or more gear flats 756. A gear flat 756 can be used to ensure that the worm follower 610 constrains the shaft 604 so that they rotate together. The one or more gear flats 756 are positioned to abut and/or contact one or more corresponding shaft flats 758 on the exterior surface of shaft 604. In the example shown, the worm follower 610 comprises a first gear flat 756A and a second gear flat 756B, and the rotatable shaft 604 comprises (i) a first shaft flat 758A positioned to correspond to the first gear flat 756A and (ii) a second shaft flat 758A positioned to correspond to the second gear flat 756B. Having more than one flat can further limit backlash between the two components. In certain implementation, the first gear flat 756A can coincide with the portion of the shaft 604 that houses the rod groove 478 (see, e.g., FIG. 10).

The one or more gear flats 756 may be milled, broached, or formed into the worm follower 610 and, as such, tight corners between the flat and curved section may not be possible or may not be desired, for instance because abrupt corners could be a location for stress fractures. Accordingly, the transitions between the one or more gear flats 756 and the curved section to provide gaps between the worm follower 610 and the shaft 604 at certain positions. Two such gaps are shown in FIG. 19C and are labeled as first gap 761A and second gap 761B. A first end of the first gear flat 756A is rounded and inwardly turned so as to come to a singular point 760. A first end of the second gear flat 756B is rounded and inwardly turned so as to come to the singular point 760. A portion of the worm follower 610 between the first gear flat 756A and the singular point 760 is separated from the rotatable shaft 604 by the aforementioned first gap 761A. A portion of the worm follower 610 between the second gear flat 756B and the singular point 760 is separated from the rotatable shaft 604 by the second gap 761B. The singular point 760 contacts the rotatable shaft 604 to provide the circumferential control of the shaft 604 within the worm follower 610.

Figure 19F:
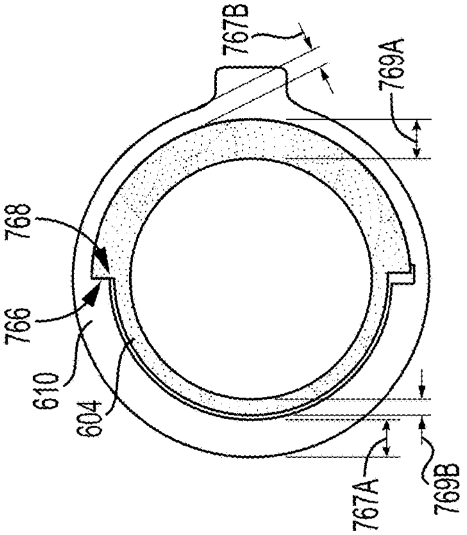
Figure 19E:
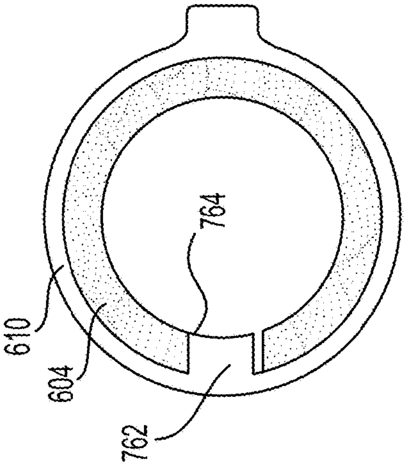
Figure 19D:
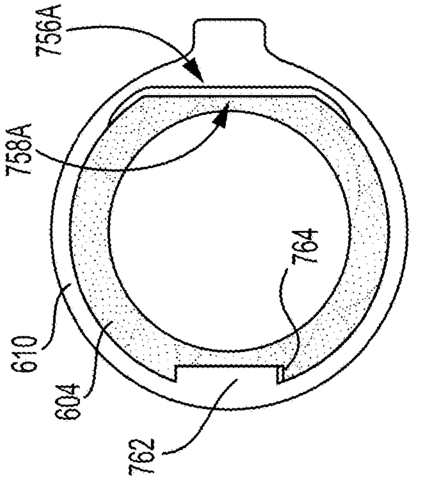

FIGS. 19D-19F show additional or alternative anti-backlash features for the worm follower 610 and shaft 604. In FIG. 19D, the worm follower 610 includes a key 762 that engages with a keyway 734 in the shaft 604. Alternatively, the shaft 604 could include the key and the worm follower 610 the keyway. In some examples, the key/keyway could be combined with one of the other anti-backlash features, such as first shaft flat 758A and first gear flat 756A, as shown. In FIG. 19E, the example shown also includes a key 762 and a keyway 734, but the keyway 734 extends entirely through the wall of the shaft 604. In FIG. 19F, the worm follower 610 has different wall thickness, as measured to the inside surface of the worm follower 610 that contacts the shaft 604. The worm follower 610 has a first portion with a first wall thickness 767A and a second portion with a second wall thickness 767B, the first wall thickness 767A being thicker than the second wall thickness 767B. This change in the interior wall geometry thereby forms a gear step 766. Similarly, the rotatable shaft 604 has a first portion with a first wall thickness 769A and a second portion with a second wall thickness 769B, the first wall thickness 769A being thicker than the second wall thickness 769B. This change in the interior wall geometry of the shaft 604 thereby forms a shaft step 768. The gear step 766 is sized and positioned to engage with the shaft step 768 to reduce backlash as the worm gear 608 actuates the worm follower 610. It is also contemplated that the worm follower 610 and shaft 604 are inseparably connected, such as with a weld or adhesive, though manufacturing a connected embodiment may take additional steps in manufacturing.

Figure 19H:
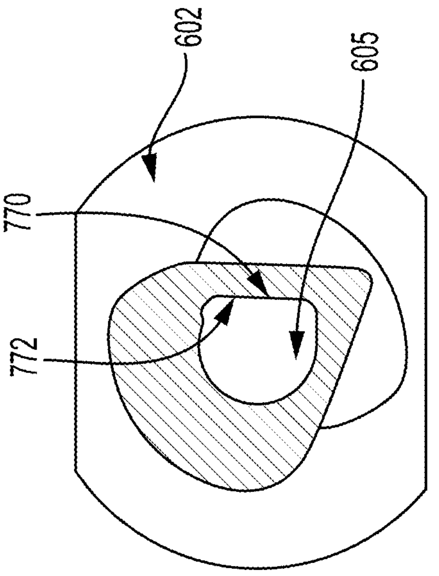
FIGS. 19G and 19H show example anti-backlash features for a worm gear, according to aspects of the present disclosure.
Figure 19G:
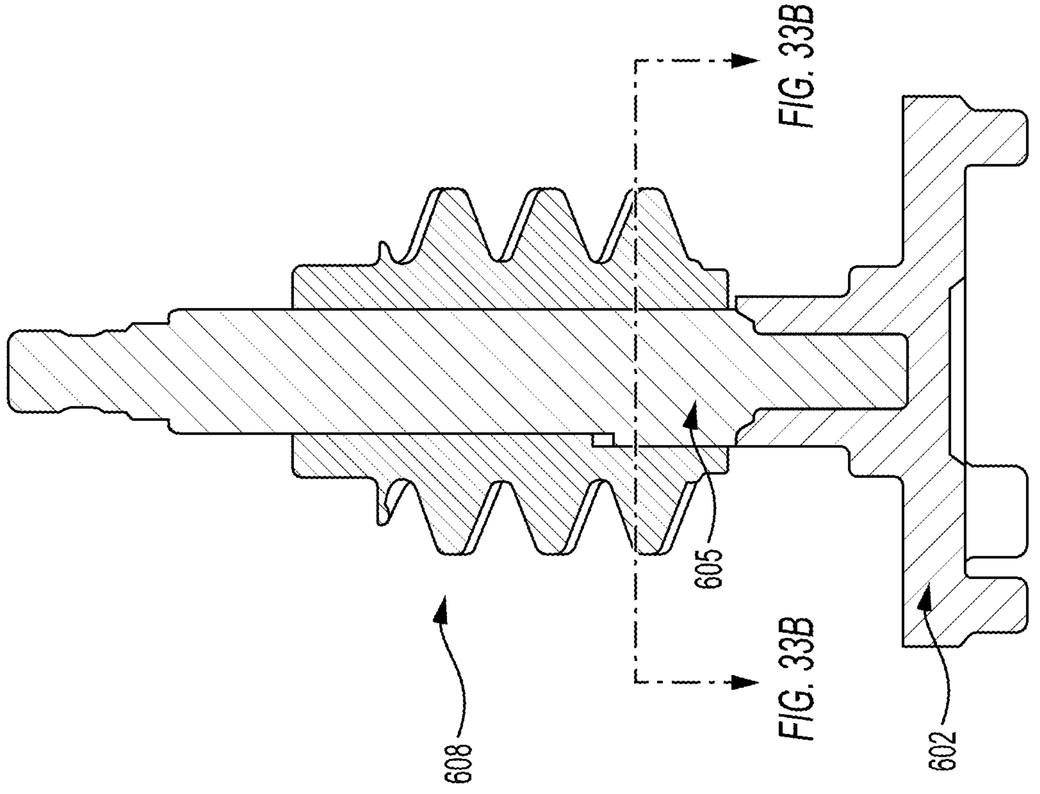
Figure 19I:
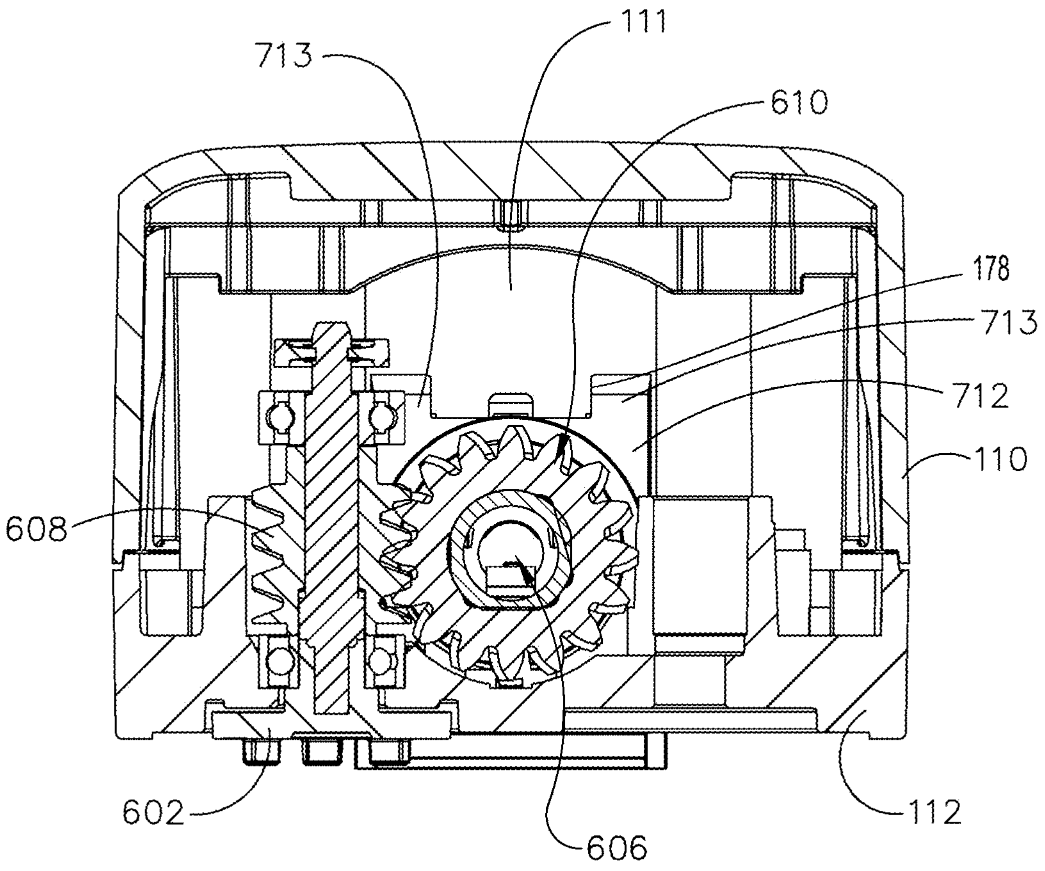
FIG. 19I is a cross sectional view of the roll subsystem, according to aspects of the present disclosure.

FIGS. 19G and 19H show example anti-backlash features for a worm gear 608, according to aspects of the present disclosure. The disclosure above discussed reducing backlash at the connection between the shaft 604 and worm follower 610, but another point of potential backlash in the roll subsystem 600 is where the roll input puck 602 and its respective input shaft 605 engages with the worm gear 608. FIG. 19G shows the placement of the input puck 602, input shaft 605, and worm gear 608, whereas the top FIG. 19H cross sectional view shows the example anti-backlash features. The input shaft 605 extends at least partially through the worm gear 608. The input shaft 605 includes a flat section 772 positioned to correspond to a worm drive flat 770 of the worm gear 608. This flat-on-flat feature is similar to the gear flats 756 and shaft flats 758 discussed with respect to FIG. 19C and helps to reduce backlash in the system.

Transection Subsystem

The surgical instrument 100 includes a transection subsystem 800. This subsystem can be referred to as a transection subsystem since actuation of the system results in a cutting of tissue via cutting mechanisms of the end effector 150, mechanisms of which are described in more detail below. The transection subsystem 800 includes a series of gears proximally that allow the system to fire a firing rack 816 distally. Because the surgical instrument 100 includes a roll feature, e.g., via the roll subsystem 600, the proximal portion of the transection subsystem 800 (e.g., with the gearing and firing rack 816, see FIG. 20) is not rotatable, but the distal end (e.g., firing rod 820, bands 826, etc., see FIG. 21) can rotate along with the roll of the shaft 604.

Figure 20:
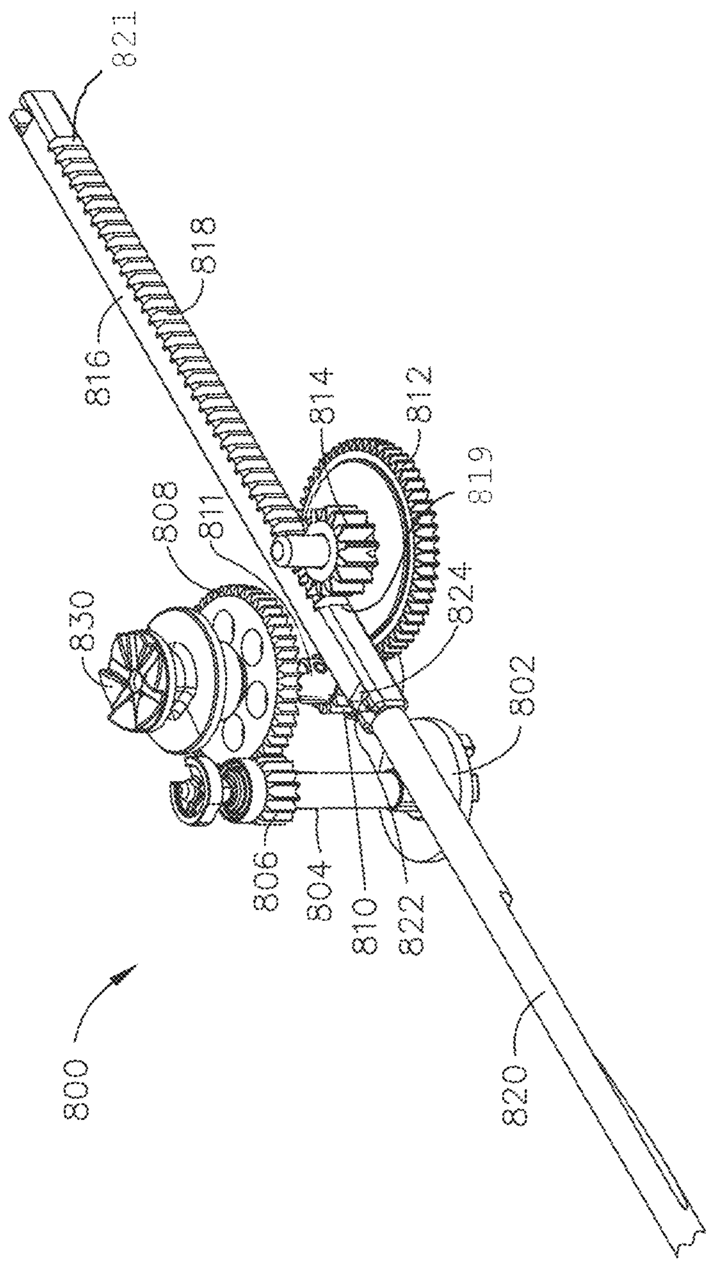
FIG. 20 shows further components of the transection subsystem, according to aspects of the present disclosure.

Referring specifically now to FIG. 20, the transection subsystem 800 includes a transection input puck 802 that is engageable with a corresponding rotatable robotic output. The transection input puck 802 can be rotationally engaged with a transection drive shaft 804 extending therefrom, such that rotation of the transection input puck 802 turns the transection drive shaft 804. Rotation of the transection drive shaft 804 causes, either directly or indirectly via gearing, distal or proximal translation of the firing rack 816, which results in firing of the staples 126 and/or knife 166 in the end effector.

Since the distal translation of the firing rack 816 is used to translate a distal knife 166 a higher degree of force is desired for the distal translation. The force needed to push the knife 166 forward can be great, as it can include the accumulation of forces required to cut tissue, drive staples, and interact with any friction. As such, the present disclosure provides a series of gearing to increase the transection, or cutting, force by providing a mechanical advantage past the transection input puck 802. The transection subsystem 800 includes a transection spur gear 806 that is coupled to the transection drive shaft 804 such that rotation of the transection drive shaft 804 also turns the transection spur gear 806. The transection subsystem 800 includes a transection ramp gear 808 that is rotatably engaged with the transection spur gear 806, meaning that rotation of the transection spur gear 806 in a first direction causes a corresponding rotation of the transection ramp gear 808 in the opposite direction. The transection ramp gear 808 can have a larger diameter than the transection spur gear 806. A ramp gear shaft 810 can be coupled to and extend from the transection ramp gear 808, such that the ramp gear shaft 810 rotates with the rotation of the transection ramp gear 808. A transection ramp spur gear 811 can be coupled to the ramp gear shaft 810 such that the transection ramp spur gear 811 can be caused to rotate when the ramp gear shaft 810 rotates.

The transection subsystem 800 includes a speed gear 812 that is rotatably engaged with the transection ramp spur gear 811, meaning that rotation of the ramp gear shaft 810 in a first direction causes a corresponding rotation of the speed gear 812 in the opposite direction. The speed gear 812 can have a larger diameter than the ramp gear shaft 810 and the transection ramp gear 808. The transection spur gear 806, the transection ramp gear 808, the transection ramp spur gear 811, and speed gear 812 can each be spur gears.

The transection subsystem 800 includes a firing gear 814 that is rotationally dependent on the gearing, for example rotation of the firing gear 814 is ultimately dependent on rotation of the transection input puck 802. In the examples with a speed gear 812, the firing gear 814 can be rotatable with rotation of the speed gear 812. The firing gear 814 is engaged with teeth 818 of the firing rack 816, such that rotation of the firing gear 814 causes a distal translation of the firing rack 816. As will be appreciated, the differences in gear sizes of the transection subsystem 800 can increase the linear velocity of the firing rack 816.

Figure 21:
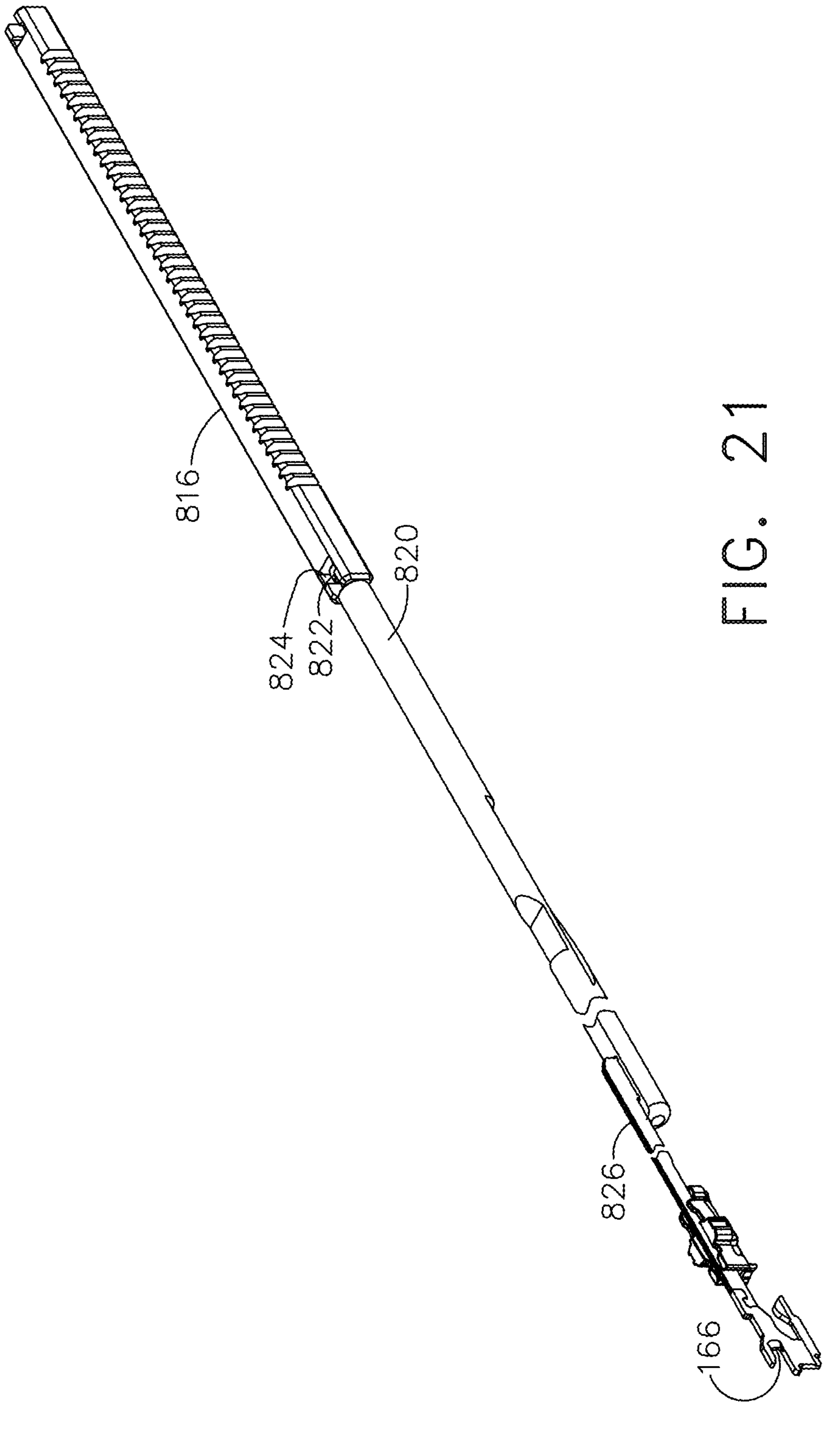
FIG. 21 shows components of a transection subsystem, according to aspects of the present disclosure.

As described above, the firing rack 816 can be rotationally stable within the outer housing 102, but because the more distal end of the transection subsystem 800 must rotate with the roll features of the roll subsystem 600, the distal portion of the transection subsystem 800 can rotate independent of the firing rack 816. The transection subsystem 800 includes a firing rod 820 rotatably coupled to the distal end of the firing rack 816, such that the firing rod 820 can rotate independent of the firing rack 816. The rotatable connector between the firing rod 820 and the firing rack 816 includes a T-shaped tab 822 on the proximal end of the firing rod 820 that engages with a slot 824 on the firing rack 816. The tab/slot connection allows free rotation of the firing rod 820 but also constrains the firing rod 820 to the firing rack 816 axially. An example of this connection between the firing rod 820 and the firing rack 816 is shown in FIGS. 20 and 21. It will be understood that the T-shaped tab could alternatively be on the firing rack 816 and the slot could be on the firing rod 820.

Figure 22A:
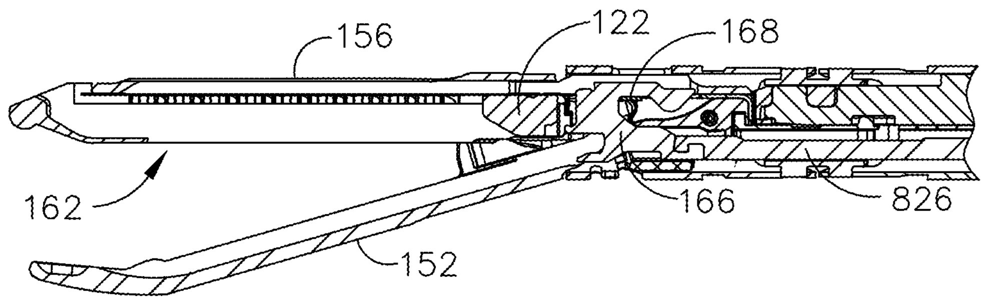
FIGS. 22A-22C show components of a transection subsystem during a progressive firing stroke, according to aspects of the present disclosure.
Figure 22B:
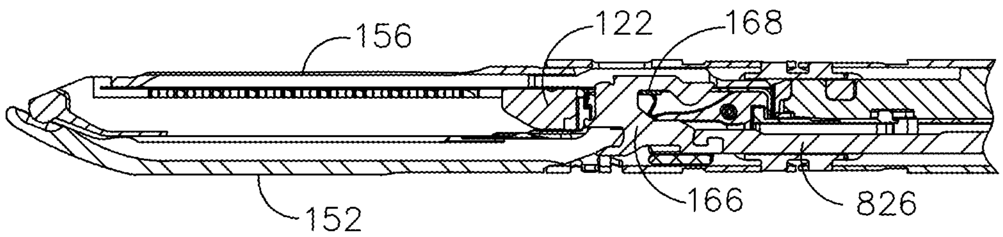
Figure 22C:
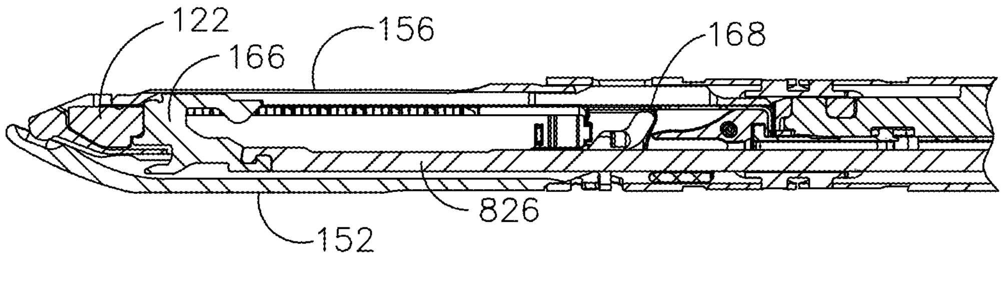

Referring to FIGS. 22A, 22B, 22C, and 23, which provide detailed views of certain distal components of the transection subsystem 800, the distal end of the firing rod 820 can be coupled to a series of bands 826 that extend distally toward the end effector 150. These bands provide a degree of flexibility to the firing mechanism, while also providing axial stiffness to push the knife 166 through tissue. The surgical instrument 100 includes a cover 832 that protects the bands 826. FIG. 22C further shows the bands 826 distally. The surgical instrument 100 includes knife guide 158 that allows the end effector 150 to articulate as described herein. The bands 826 can pass through the knife guide 158, and the knife guide 158 provides lateral support to guide the laminates through any articulation angle. The bands 826 can also pass through the band slot 484 of the attachment end 468 of the distal channel retainer 408.

Referring to FIGS. 22A, 22B, and 22C, the transection subsystem 800 can have a final firing length that can correspond to a length of a staple cartridge 120 within the end effector 150. For example, if a staple cartridge 120 provides 35 mm of cutting/stapling, then the transection subsystem 800 can be configured to translate the firing rack 816 a maximum of 35 mm, as shown in FIG. 22C. It will be understood that certain degrees of tolerance can be built in depending on how long the staple cartridge 120 is to deliver 35 mm of staples.

Figure 23:
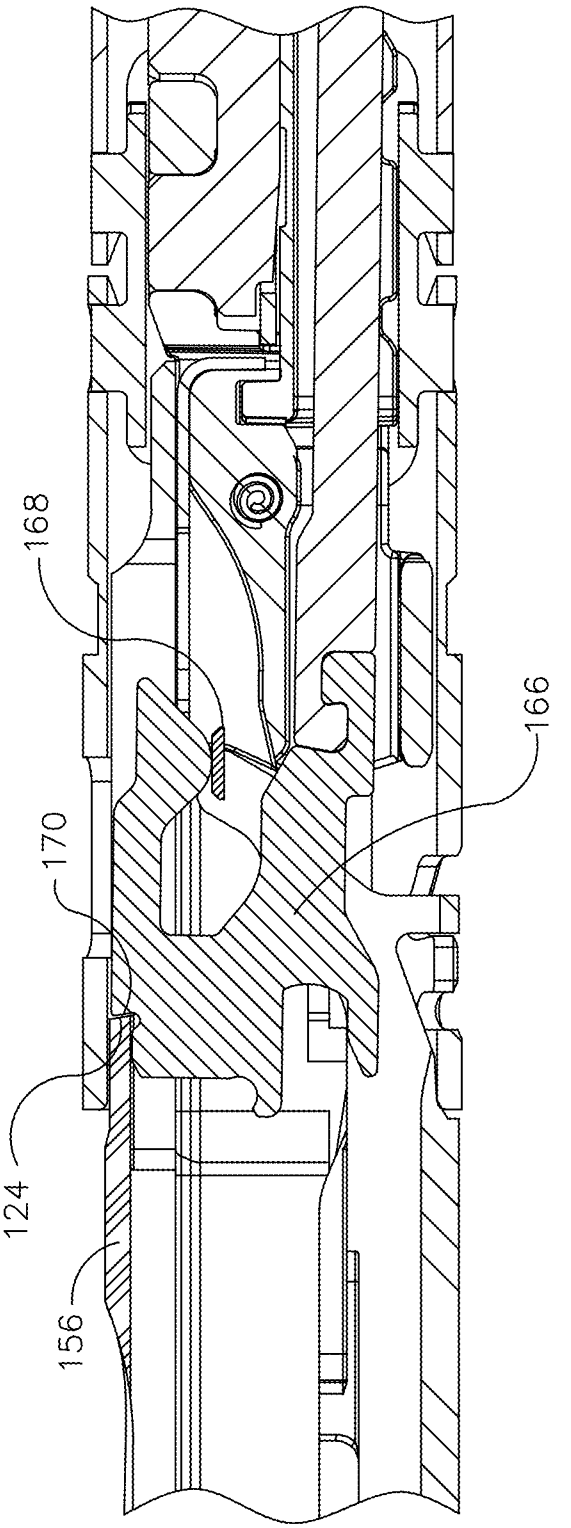
FIG. 23 shows shaft closure components of a surgical instrument, according to aspects of the present disclosure.

The end effector 150 can include an anvil 152. The channel 156 can accept a staple cartridge 120 within a cartridge slot 162 therein. The staple cartridge 120 can include a plurality of staples 126. A sled 122 can be driven distally (as shown in FIG. 22C) through the cartridge 120 to drive the staples 126 into the anvil 152. The sled 122 can be pushed distally via the knife 166 at the end of the bands 826. The knife 166 can, therefore, act both as a firing member to push the sled 122 distally and as a transection member to cut tissue. The knife 166 can be retained at a closed non-fired position by a leaf spring 168 (as shown in FIG. 23). The leaf spring 168 can bias knife 166 into a lockout position if no sled 122 is present and, as the knife 166 travels distally forward, the leaf spring 168 will stop the knife 166 from moving forward. The anvil 152 can include an anvil ramp 154 proximally. The closure subsystem 200 can close the anvil 152 by moving the closure ring 226 distally and over the anvil ramp 154, thereby hinging the anvil 152 closed.

FIG. 20 also shows two hard stop features of the firing rack 816. More distally is a distal hard stop 819, and more proximally is a proximal hard stop 821. These hard stops 819, 821 exist where the teeth 818 of the firing rack 816 end, thereby providing a mechanical backup to stop the firing rack 816 from either over firing (i.e., the proximal hard stop 821 prevents the firing rack 816 from over-extending) or from over retracting (i.e., the distal hard stop 819 prevents the firing rack 816 from over-retracting).

In some examples, the end effector 150 can have a safety mechanism in place to prevent attempts to fire a spent cartridge, or prevent firing the knife 166 when there is no sled 122 present. For example, the knife 166 can be biased toward the channel 156, and the knife 166 requires a sled 122 to be present for the knife 166 to travel distally. As shown in FIG. 23, if no sled 122 is present (indicating that the cartridge 120 is spent or there is no cartridge 120), the knife 166 will bend toward the channel 156, and then a lockout feature 170 on the knife 166 can contact a lockout wall 124 on the channel 156 to stop distal movement of the knife 166.

To help prevent the end effector 150 from moving while the transection subsystem 800 fires the knife 166, the surgical instrument 100 can be configured to cause the first articulation input puck and the second articulation input puck 404 to rotate and apply opposing forces on each other. In this way, the articulation system 400 can effectively be locked to prevent distal movement of the knife 166 and knife bands 826 from causing the articulation system 400 to move while the transection subsystem 800 is firing. This can be accomplished by a control device 1110 (described further herein) causing the first articulation input puck and the second articulation input puck 404 to rotate in directions to cause opposing forces on each other. For example, if the articulation subsystem 400 includes two racks 414, 418, the method 1200 can include turning the first articulation input puck 402 and the second articulation input puck 404 in opposite directions. On the other hand, if the articulation subsystem 400 includes a single rack 414C, the method 1200 can include turning the first articulation input puck 402 and the second articulation input puck 404 in the same direction. In this way, the articulation subsystem 400 can be preventing from causing the end effector 150 from moving side to side.

Figure 24A:
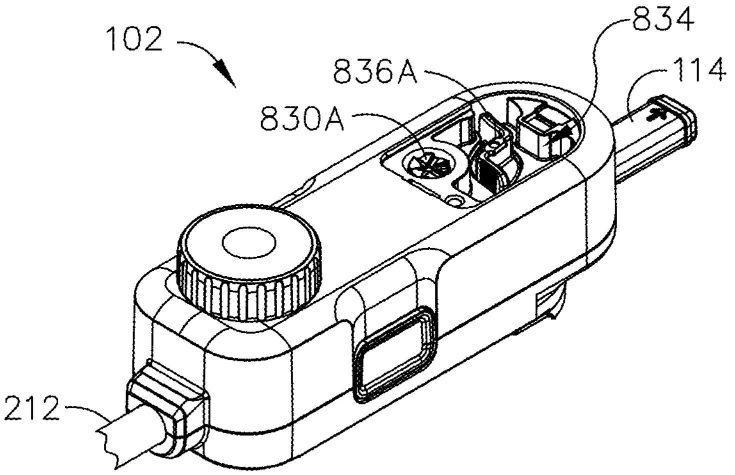
FIGS. 24A-24C show a compartment for a knife return mechanism, according to aspects of the present disclosure.
Figure 24B:
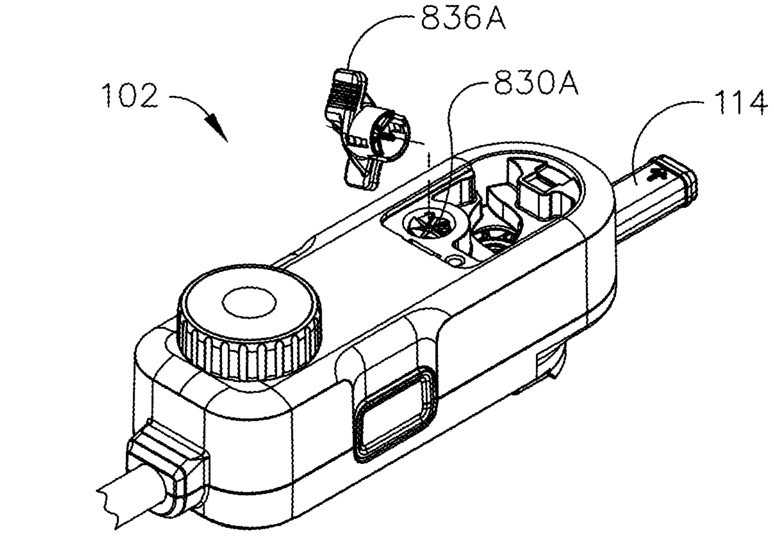
Figure 24C:
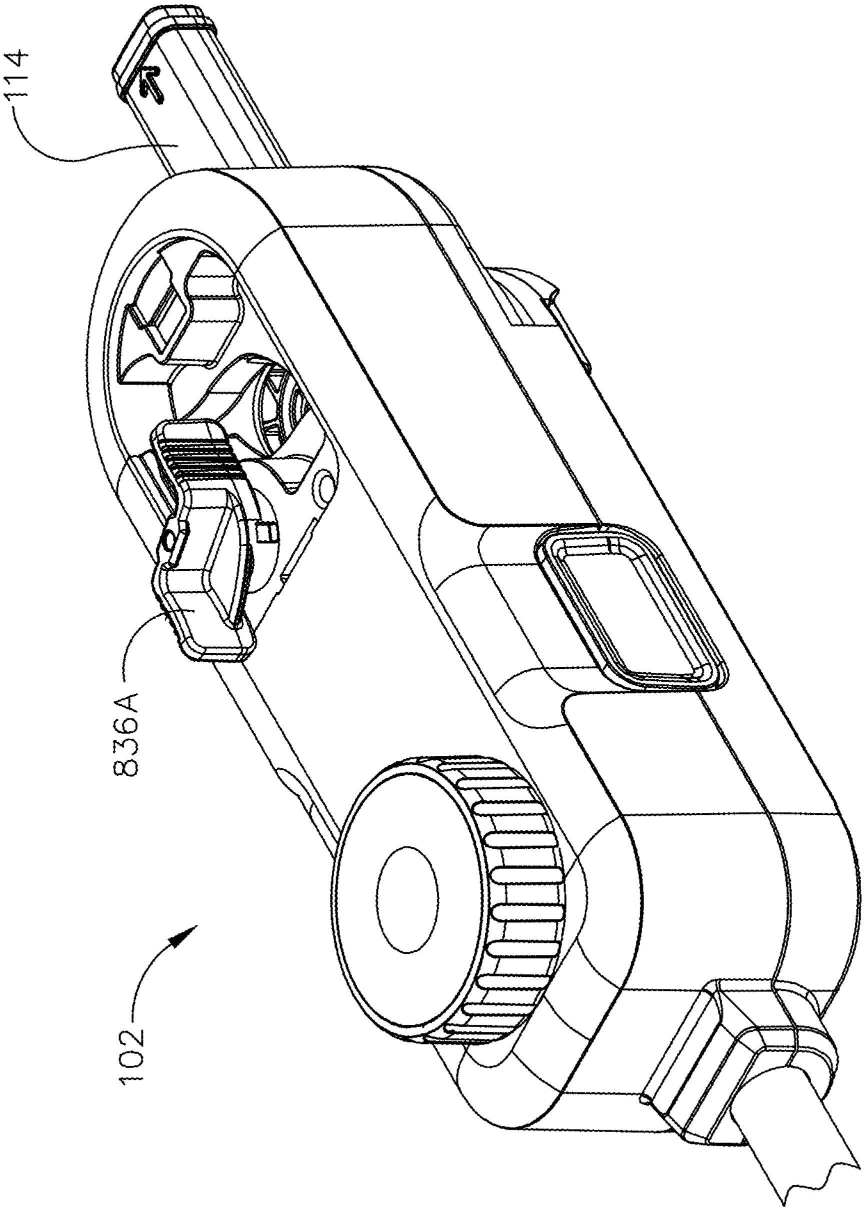

As shown in FIGS. 24A, 24B, and 24C, the transection subsystem 800 includes a key receiver 830A that can be rotationally coupled to the gearing of the transection subsystem 800 to manually retract the firing rack 816 and thus knife 166. The key receiver 830A can be rotationally coupled to the transection ramp gear 808 or the speed gear 812, whereas rotationally coupling the key receiver 830A to the transection ramp gear 808 provides a higher degree of gearing ratio such that rotation of the key receiver 830A moves the firing rack 816 proximally more quickly. This mechanical, manual retract can help in the scenario where the distal knife 166 has become stuck or otherwise unable to retract, and the robot is unable to turn the transection input puck 802 sufficiently to retract the knife 166.

In some examples, the outer housing 102 of the surgical instrument 100 can have a compartment 834 that is closed by a cover 832 (shown in FIG. 2B) that provides access to the manual knife return key 836A. The top of the key receiver 830 can have a pattern (unidirectional ramps shown in FIG. 24E) that matches a unidirectional pattern on the manual knife return key 836A so that the firing rack 816 can only be retracted using this manual override, and not advanced. In some examples, the firing rack 816 can extend proximally from the outer housing 102 and can be covered by a tail cover 114. For example, the key receiver 830A can include ramps that allow unidirectional application or torque from the manual knife return key 836A. The tail cover 114 can be made from a transparent material so that surgical staff can view the position of the firing rack 816.

Figure 24D:
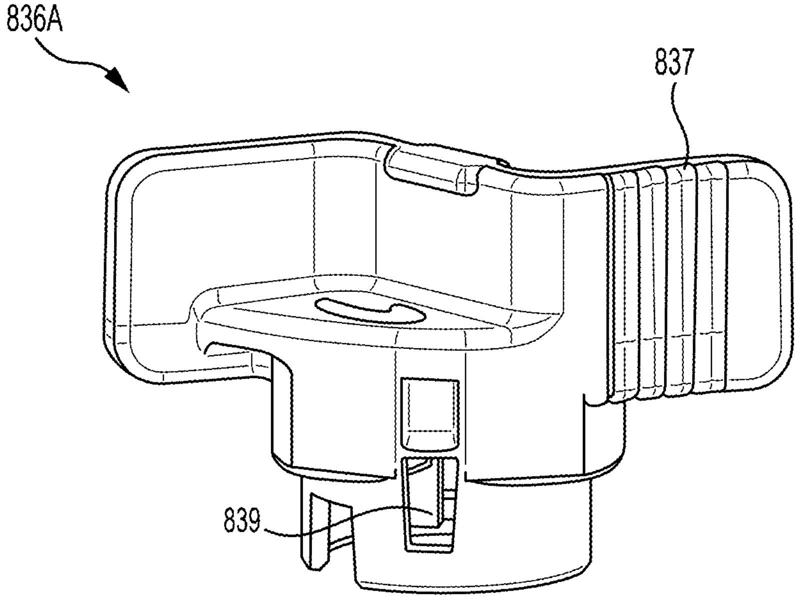
FIG. 24D is a perspective view of a manual knife return key, according to aspects of the present disclosure.
Figure 24E:
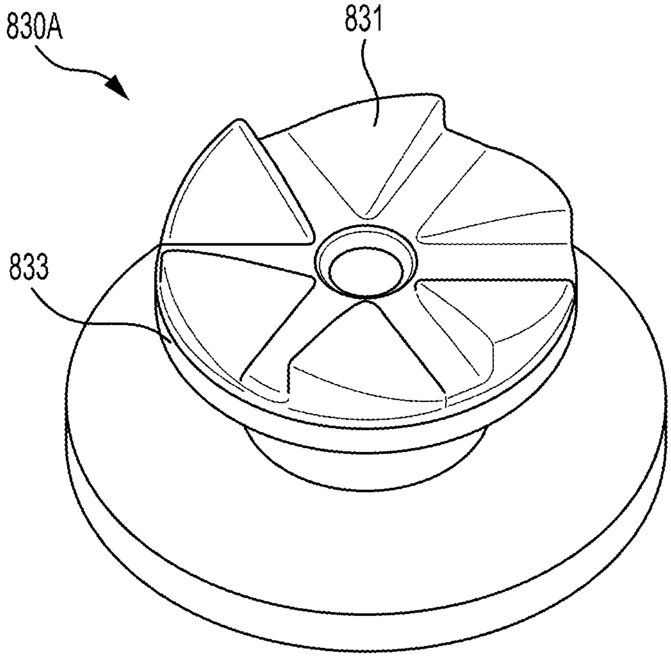
FIG. 24E is a perspective view of a key receiver, according to aspects of the present disclosure.

As shown in FIG. 24D, the manual knife return key 836A can include one or more locking tabs 839 configured to attach the manual knife return key 836A to the key receiver 830A. For example, as shown in FIG. 24E, the key receiver 830A can include a ledge 833 about which the locking tab 839 can extend to prevent the manual knife return key 836 from detaching from the key receiver 830A when attached. The locking tabs 839 can be positioned such that the manual knife return key 836A can move upwardly away from the key receiver 830A if the manual knife return key 836A is turned in the wrong direction but still be prevented from detaching from the key receiver 830A.

Figure 25A:
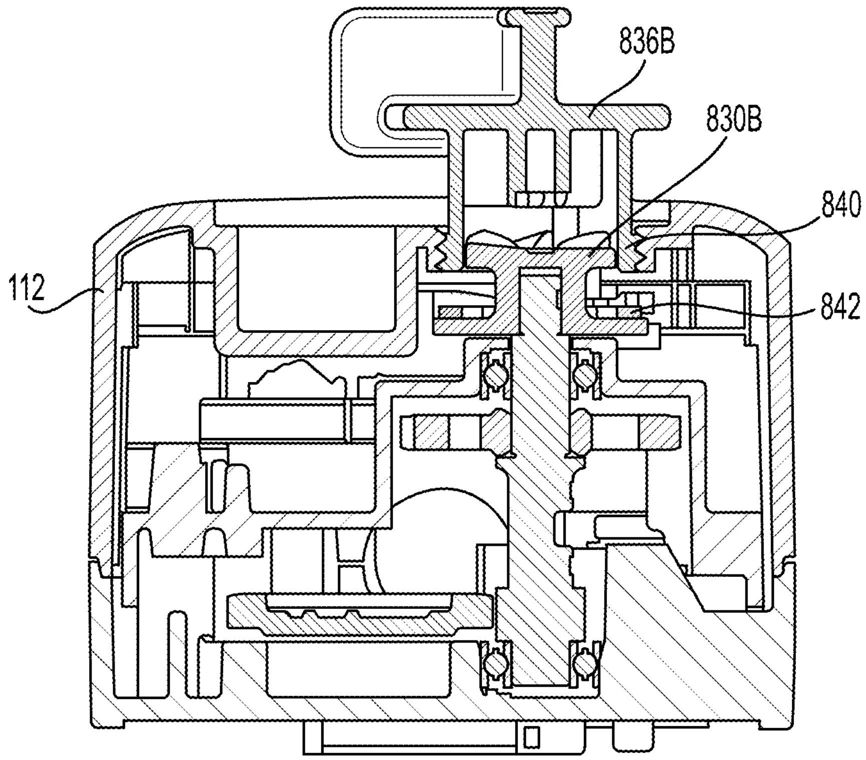
FIGS. 25A and 25B are section views of an alternative manual knife return system, according to aspects of the present disclosure.
Figure 25B:
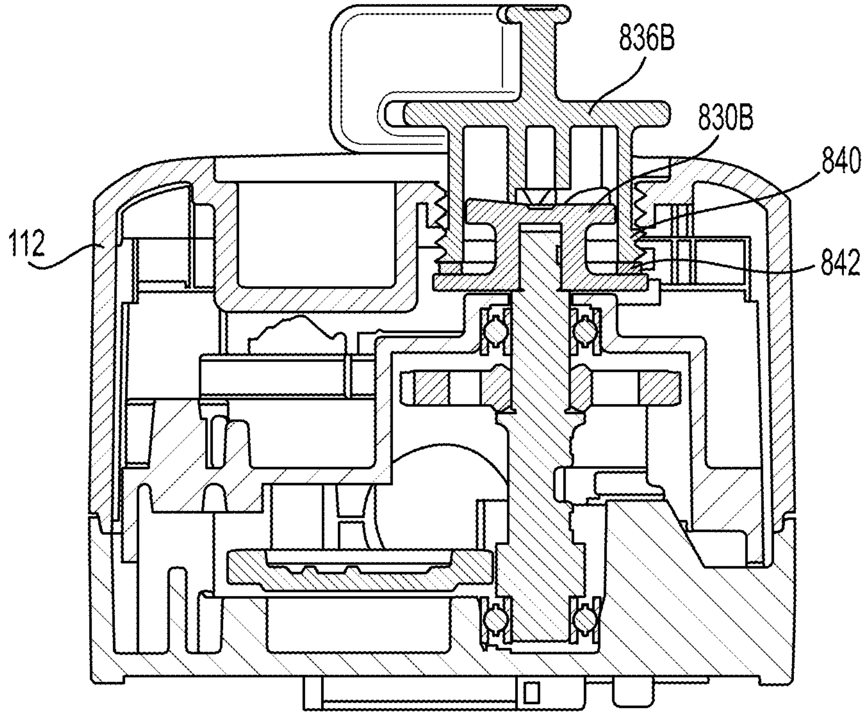

Several different examples of manual knife return configurations will now be described in relation FIGS. 25A-25Q. FIGS. 25A and 25B are cross-sectional views of alternate manual knife return key 836B and a key receiver 830B. The manual knife return key 836B in this example comprises exterior threads 840 that align with threads of the second portion 112 of the housing 102. The manual knife return key 836B can be threaded into the second portion 112 of the housing 102 and aligned with the key receiver 830B to manually retract the knife 166. The example shown in FIGS. 25A and 25B can include a gasket 842 that can bias the manual knife return key 836B outwardly such that the threads 840 of the manual knife return key 836B will engage the second portion 112 of the housing 102 to cause the manual knife return key 836B to remove from the housing 102 if the manual knife return key 836B is turned in the wrong direction. As will be appreciated, the threads 840 can help to retain the manual knife return key 836B in the housing 102 so that it won't be dropped or otherwise dislodged.

Figure 25C:
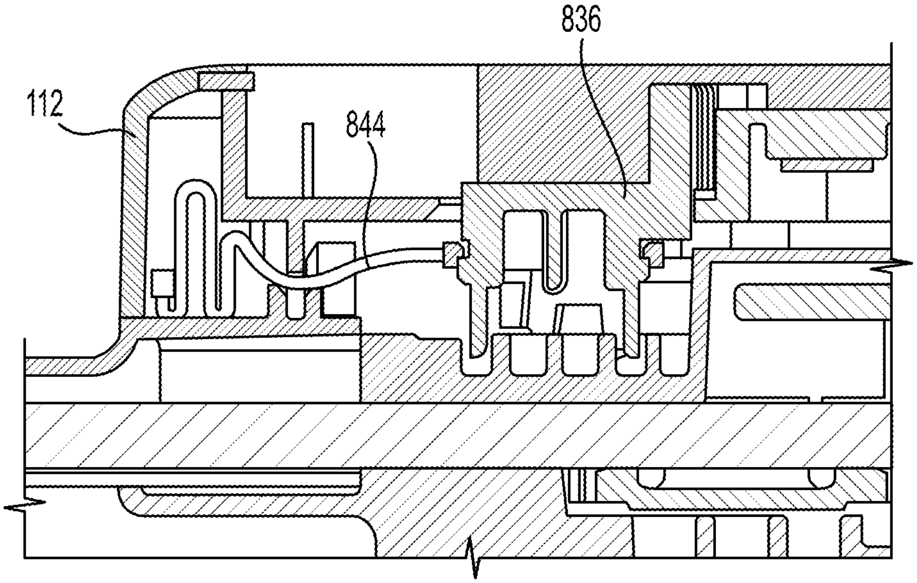
FIGS. 25C and 25 D are section and detail views showing a tether of the manual knife return system, according to aspects of the present disclosure.
Figure 25D:
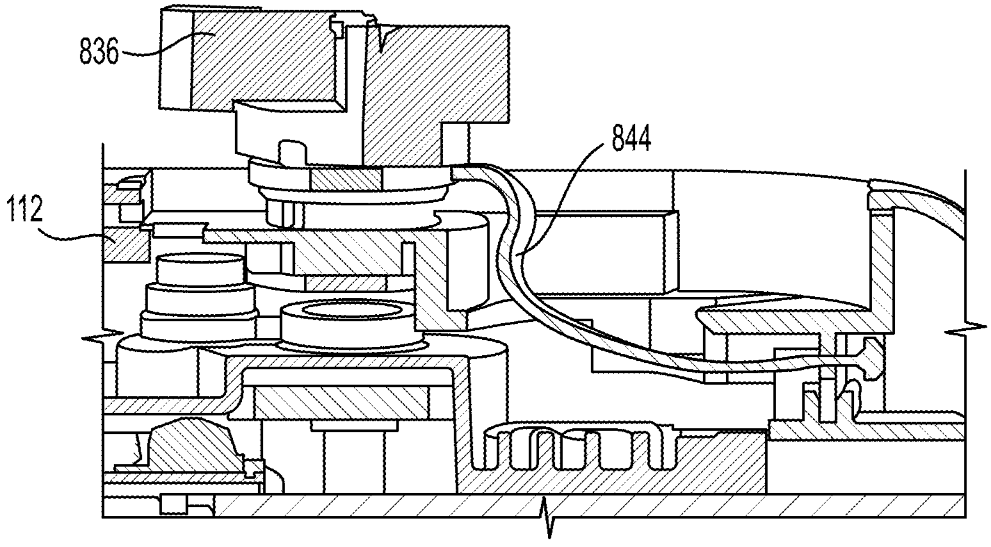
FIG. 25E is a top perspective view of the tether of the manual knife return system, according to aspects of the present disclosure.
FIG. 25F is a section view of an alternative manual knife return key, according to aspects of the present disclosure.
FIG. 25G is a detail view of an alternative manual knife return key and key receiver, according to aspects of the present disclosure.
FIG. 25H is a section view of another example manual knife return key, according to aspects of the present disclosure.
FIG. 25I is a perspective view of another example key receiver, according to aspects of the present disclosure.
FIG. 25J is a section view of the other manual knife return system corresponding to FIGS. 25H and 25I, according to aspects of the present disclosure.
FIG. 25K is a section view of yet another example manual knife return system, according to aspects of the present disclosure.
FIG. 25L is a section view of still another example manual knife return system, according to aspects of the present disclosure.
FIG. 25M is a side view of another example key receiver, according to aspects of the present disclosure.
FIG. 25N is a transparent perspective view of another alternative manual knife return key and a key receiver, according to aspects of the present disclosure.
FIG. 25O is a perspective view of still another example key receiver, according to aspects of the present disclosure.
FIGS. 25P and 25Q illustrate interaction between a manual knife return key and the other example key receiver shown in FIG. 25O, according to aspects of the present disclosure.
Figure 25E:
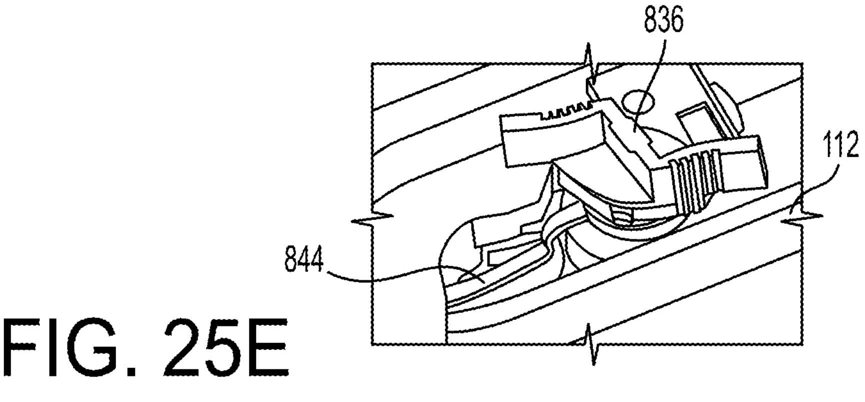

FIGS. 25C, 25D, and 25E illustrate a tether 844 that can be used with a manual knife return key 836 to help secure the manual knife return key 836 to the surgical device 100. The tether 844 can be attached around the manual knife return key 836 but allow for the manual knife return key 836 to turn freely. The tether 844 can be attached at the opposite end to the second portion 112 of the housing 102. In this way, the manual knife return key 836 can be prevented from being dropped or dislodged. As will be appreciated, dropping the manual knife return key 836 can lead to the manual knife return key 836 becoming unsterile and requiring either a replacement manual knife return key 836 or cleaning of the manual knife return key 836.

Figure 25F:
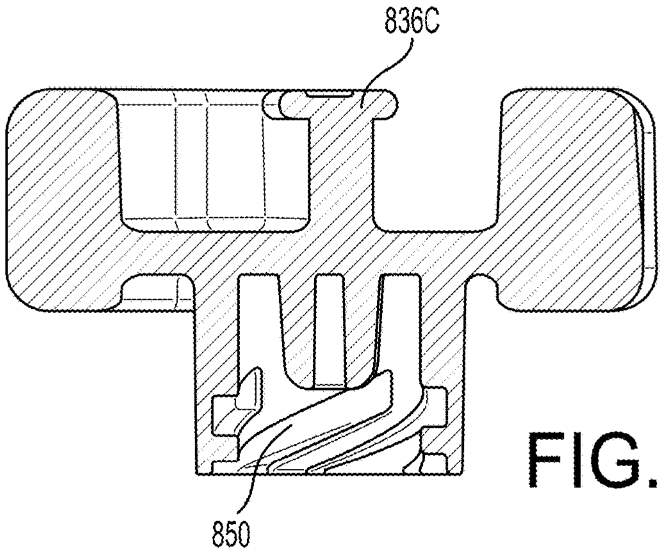
Figure 25G:
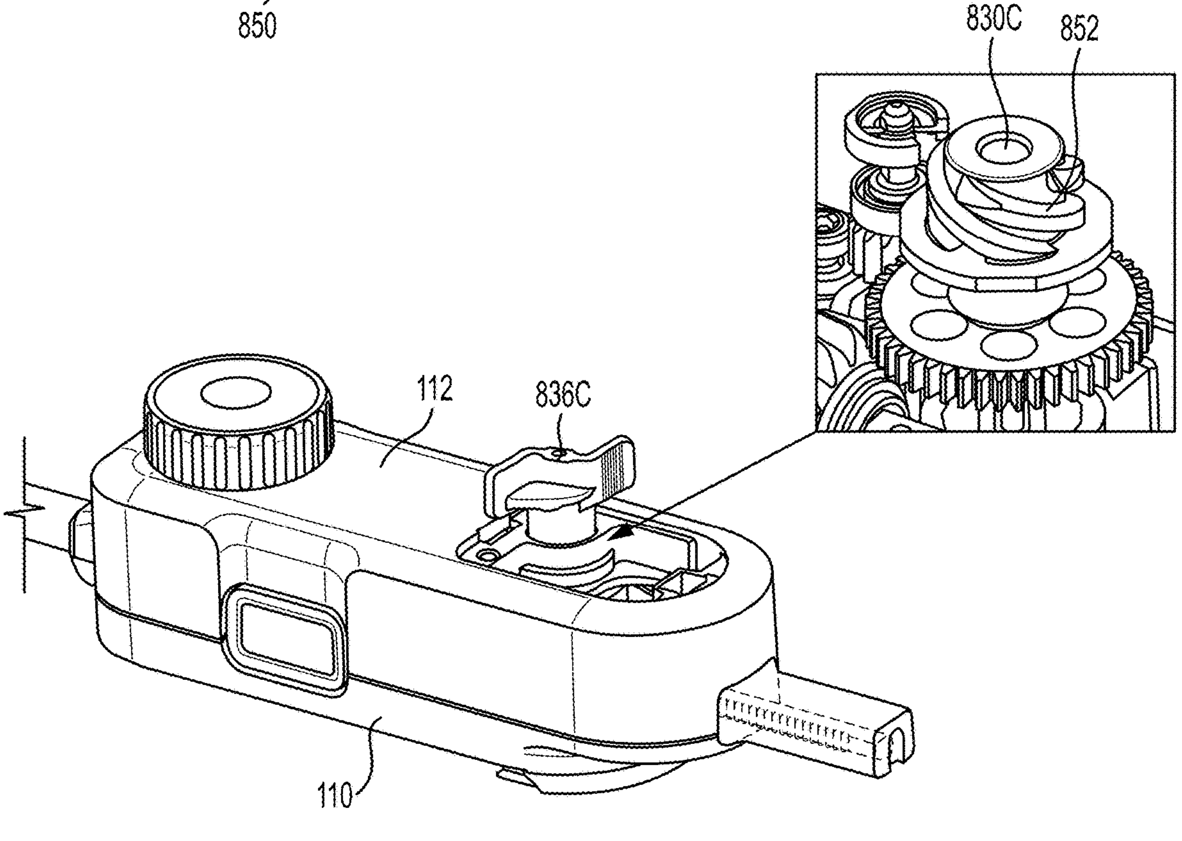

FIGS. 25F and 25G illustrate alternate examples of the manual knife return key 836C and the key receiver 830C. The manual knife return key 836C can include an internal cam 850 and the key receiver 830C can include a spline 852 that can correspond to the internal cam 850. In this example, the manual knife return key 836C can be threaded onto the key receiver 830C only in one direction to help prevent causing the knife 166 to extend distally (i.e., you only want the knife 166 to be retracted proximally when using the manual knife return key 836).

Figure 25J:
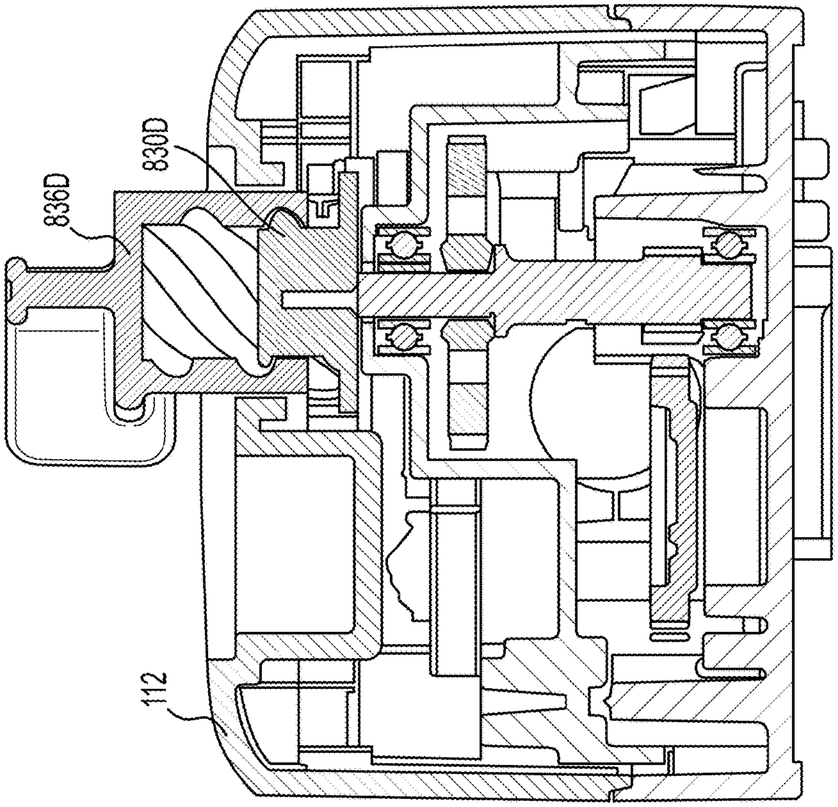
Figure 25H:
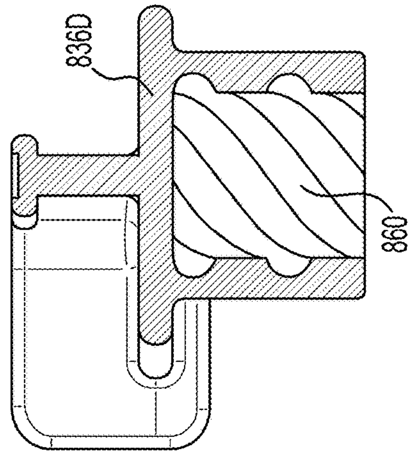
Figure 25I:
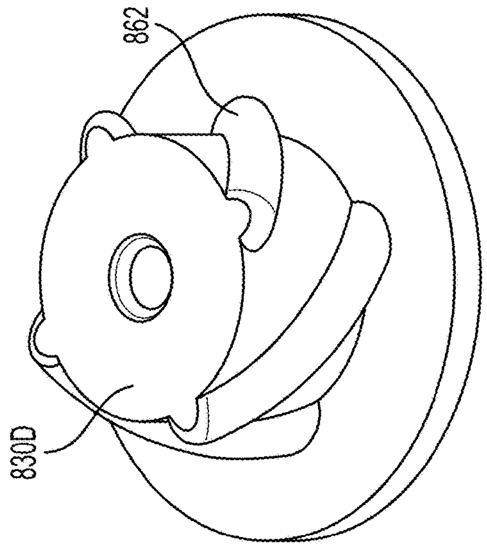

FIGS. 25H-25J illustrate a similar manual knife return key 836D to the manual knife return key 836C and a similar key receiver 830D to the key receiver 830C. The manual knife return key 836D, however, can include a rounded internal cam 860 and the key receiver 830D can include a rounded spline 862. The rounded internal cam 860 can similarly engage the rounded spline 862 only in one direction to help ensure the manual knife return key 836D is rotated only in the direction of retracting the knife 166.

Figure 25K:
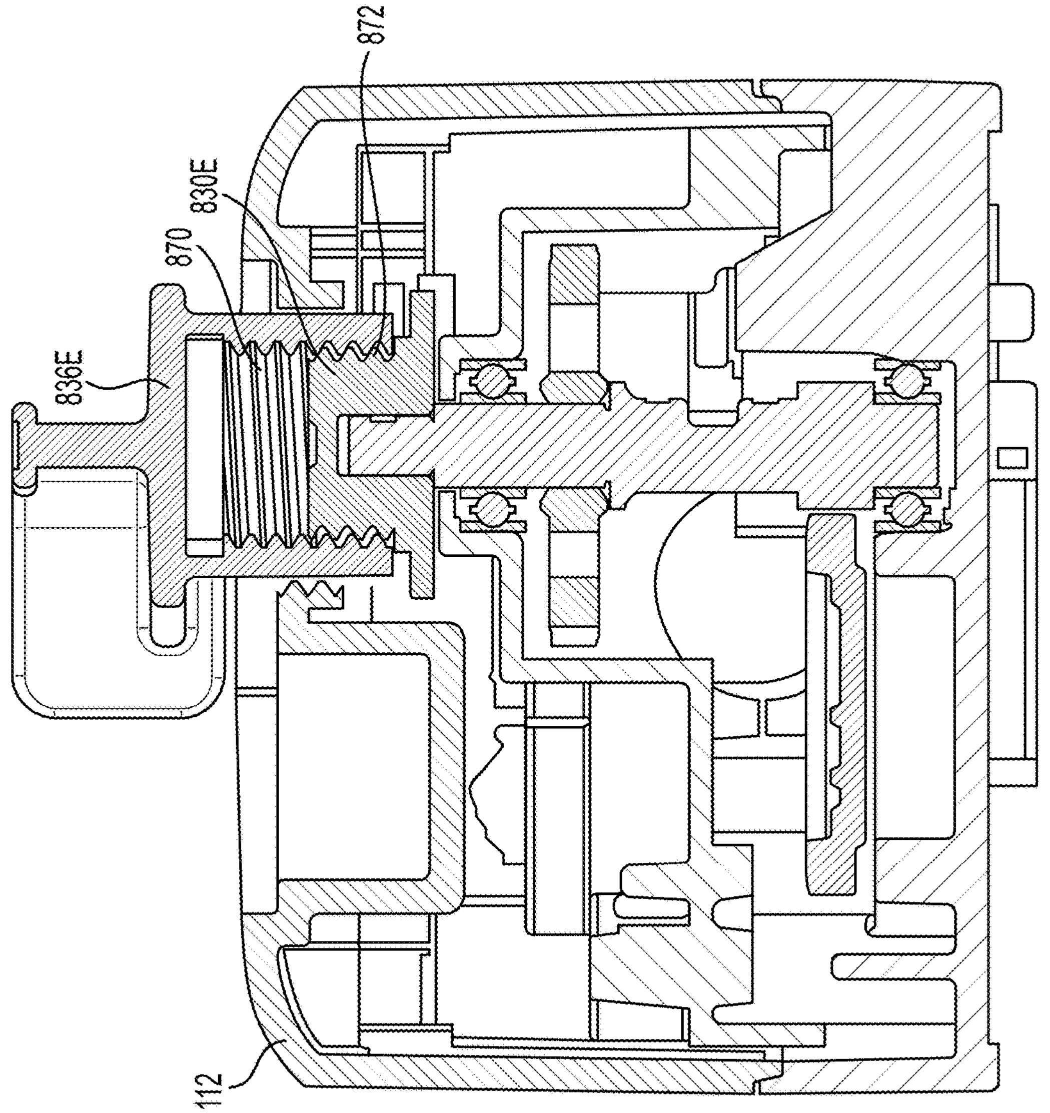

FIG. 25K illustrates yet another manual knife return key 836E and key receiver 830E. The manual knife return key 836E can include internal threads 870 and the key receiver 830E can include external threads 872 that correspond to the internal threads 870. As before, the internal threads 870 are threaded in the direction of causing the knife 166 to retract. Thus, if a user were to turn the manual knife return key 836E in the wrong direction (i.e., cause the knife 166 to move distally), the internal threads 870 and the external threads 872 will cause the manual knife return key 836E to disengage from the key receiver 830E.

Figure 25L:
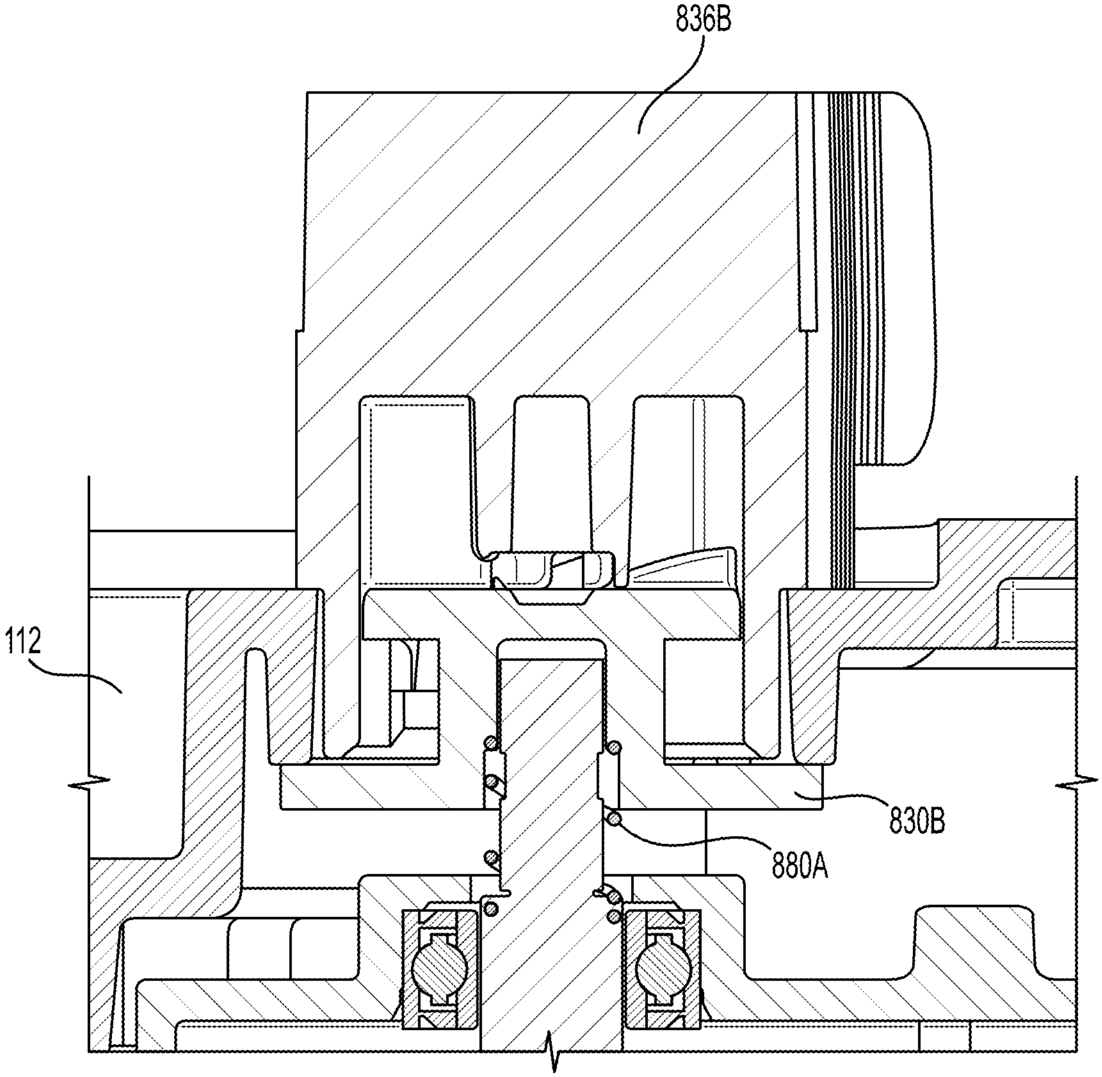

FIG. 25L illustrates the manual knife return key 836B with the key receiver 830, but also includes a spring 880A that can permit the key receiver 830B to disengage from the manual knife return key 836B when the manual knife return key 836 is turned in the wrong direction. In this way, the key receiver 830B must be turned by the manual knife return key 836B in the correct direction to cause the knife 166 to retract. As shown in FIG. 25L, the manual knife return key 836B can be configured to contact the second portion 112 of the housing 102 to prevent a user from inserting the manual knife return key 836B into the key receiver 830B with sufficient force to overcome the ramps to cause the knife 166 to move distally. In other words, by including a spring 880A, a user can only turn the key receiver 830B in the correct direction (to cause the knife 166 to retract).

Figure 25M:
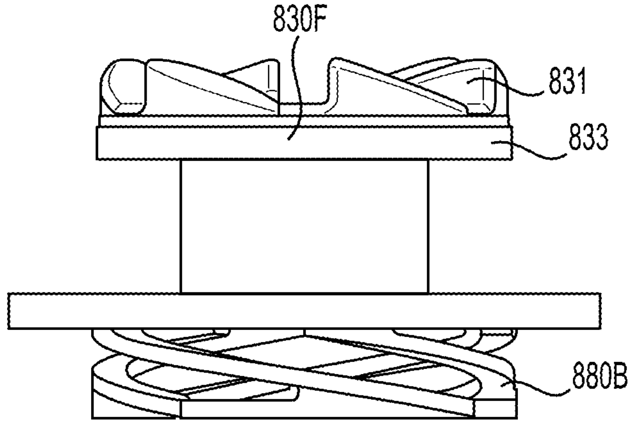

FIG. 25M illustrates another example of a key receiver 830F. The key receiver 830F can be similar to the key receiver 830B and spring 880A combination shown in FIG. 25L except the key receiver 830F includes an integrated spring 880B. The integrated spring 880B can perform the same function as the spring 880A described in relation to FIG. 25L. That is the integrated spring 880B permits the key receiver 830F to disengage from the manual knife return key 836B when turned in the wrong direction.

Figure 25N:
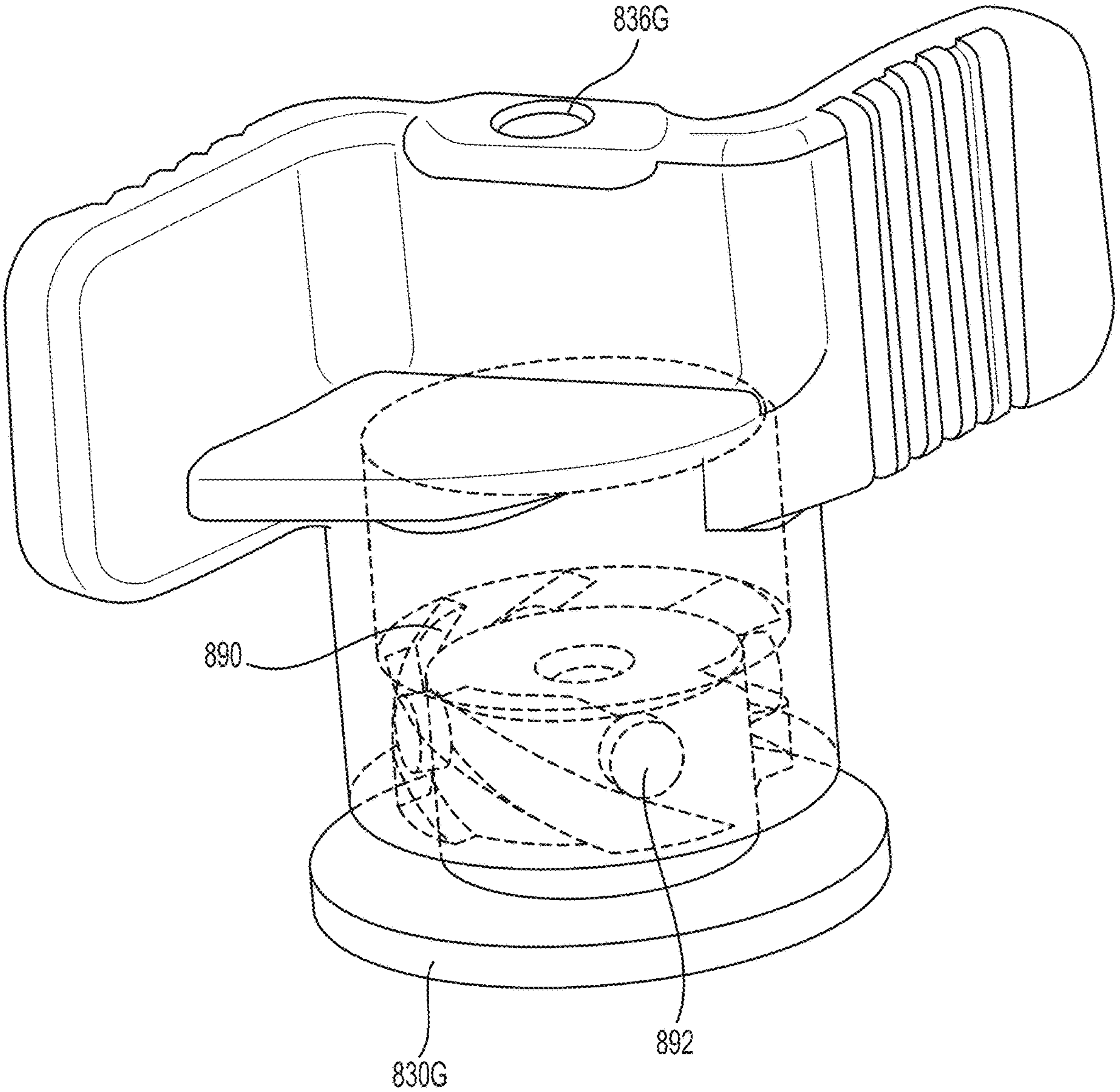

FIG. 25N illustrates another example manual knife return key 836G having an internal cam 890 design and the key receiver 830G can include a protrusion 892 that can extend into the internal cam 890. The manual knife return key 836G and key receiver 830G can be used similar to the manual knife return keys 836C and 836D previously described in that the manual knife return key 836G can only turn the key receiver 830G in one direction (i.e., the direction of retracting the knife 166).

Figure 25O:
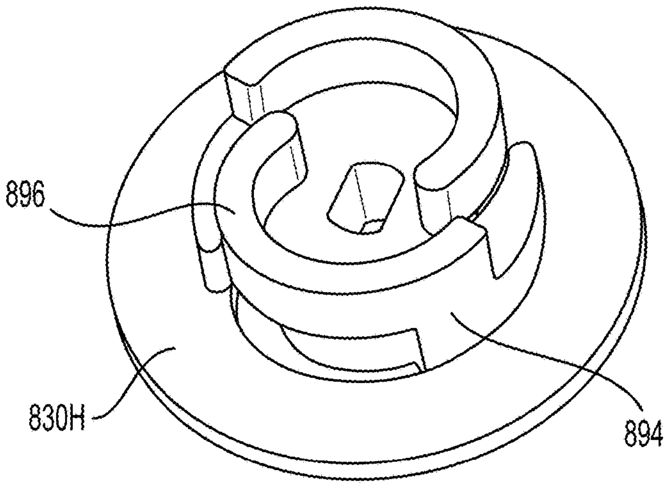
Figure 25P:
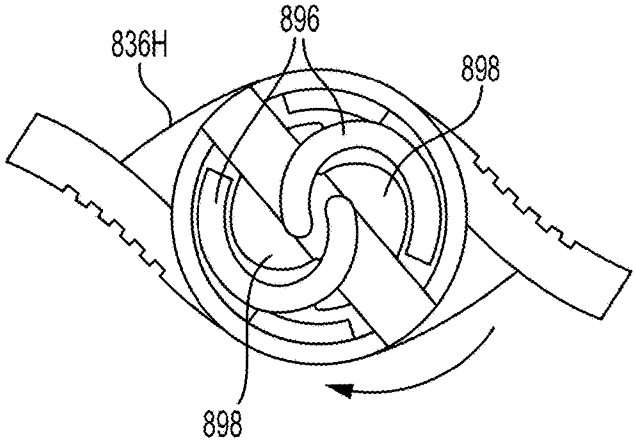
Figure 25Q:
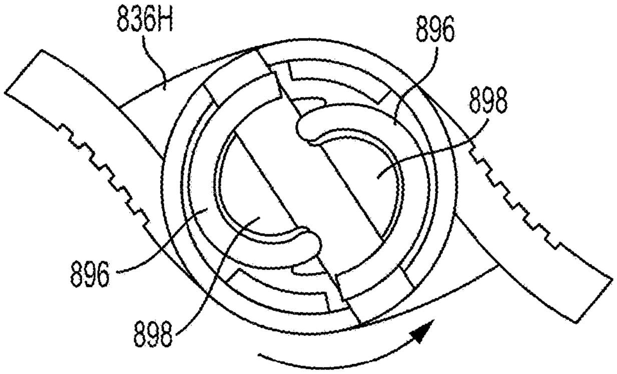

FIGS. 25O, 25P, and 25Q illustrate yet another example of a key receiver 830H and a manual knife return key 836H. The key receive 830H in this example can include supported walls 894 and cantilevered walls 896. The cantilevered walls 896 can be configured to bend out of the path of a key knobs 898 of the manual knife return key 836H when turned in the wrong direction (as shown in FIG. 25Q) but engage with the key knobs 898 when the manual knife return key 836H is turned in the correct direction (as shown in FIG. 25P). That is, the cantilevered walls 896 enable the key receiver 830H to only turn in the direction of the knife 166 retraction. If the user tried to turn the manual knife return key 836H in the wrong direction (i.e., causing the knife 166 to move distally), the cantilevered walls 896 will disengage from the manual knife return key 836H and the user cannot cause the knife 166 to move distally.

Figure 26:
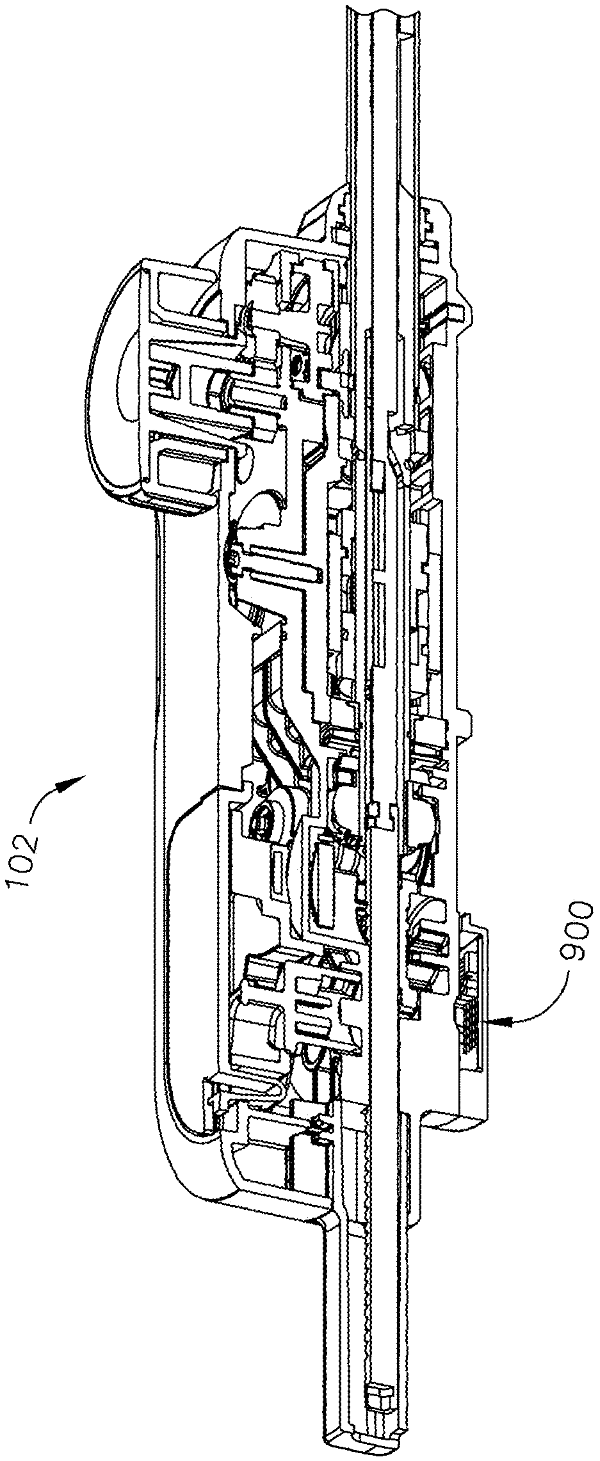
FIG. 26 is a section view of the surgical instrument taken vertically along the longitudinal axis, according to aspects of the present disclosure.

FIG. 26 is a cross-section view of the surgical instrument 100 illustrating electronics 900 of the surgical instrument 100. The electronics 900 can store data such as calibration data such that, when the surgical instrument 100 is first attached to a robotic arm 1100, the control device 1110 of the robot arm 1100 (as described in greater detail here) can recognize the calibration data and control the surgical instrument 100 according to the stored calibration data. That is, the surgical instrument 100 can be calibrated at a factory and then the calibration data can be stored on the electronics 900 to be used by the control device 1110 of the robotic arm 1100 to ensure the surgical instrument 100 is properly controlled.

Fluid Management

Figure 27B:
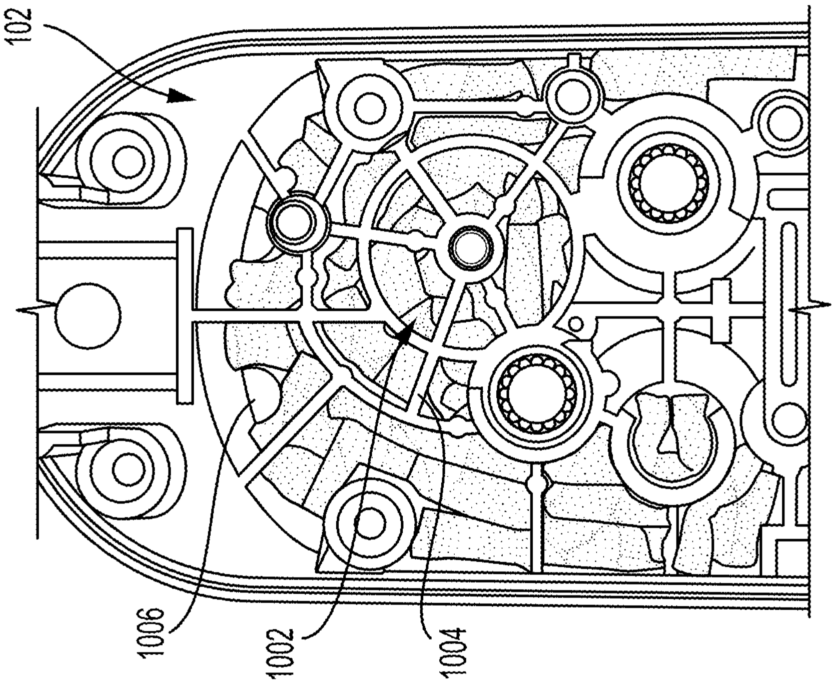
FIG. 27B shows absorbent materials positioned inside cavities.
Figure 27A:
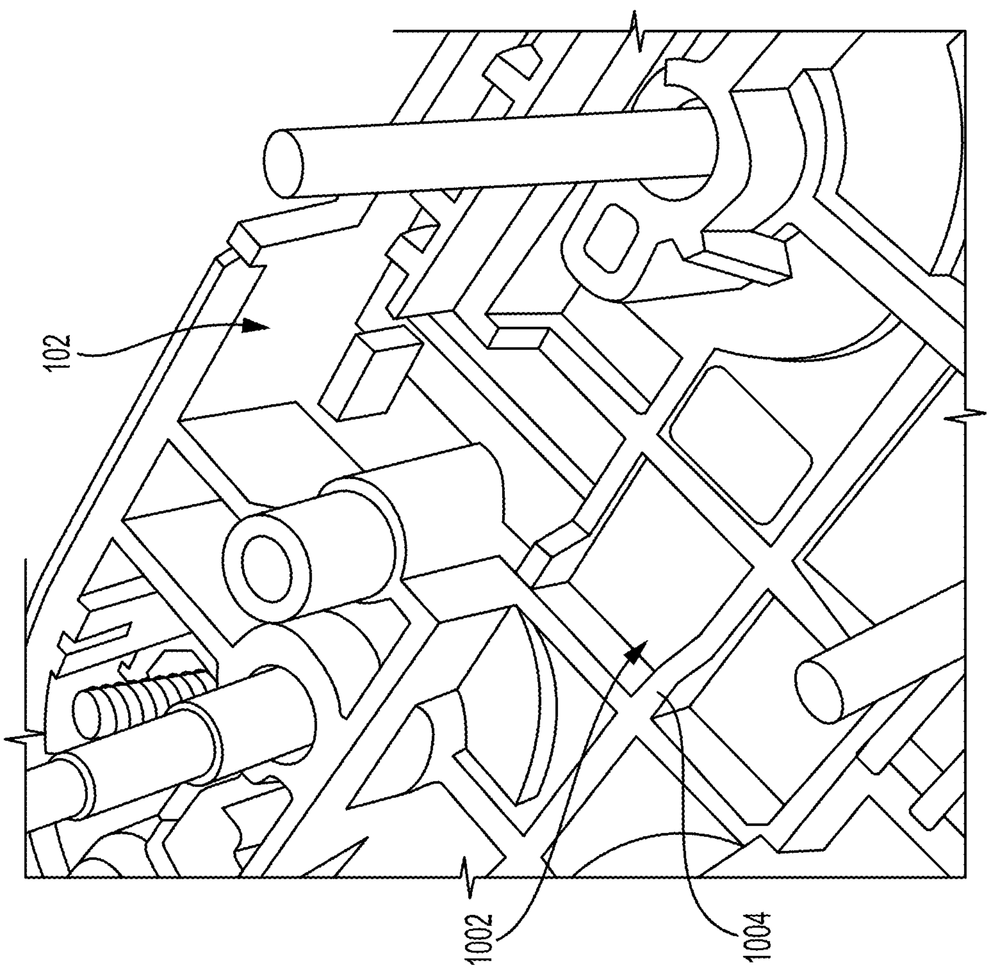
FIG. 27A-27R show features to control fluid egress from a housing, according to aspects of the present disclosure.

The surgical instrument 100 is intended to be subjected to bodily fluid and sterile saline swishes that travel on and through the shaft 604 and housing 102 of the instrument. For example, a primary source of fluid is from a swishing step that clears stray staples and tissue from the end effector 150. A scrub nurse can then hold the surgical instrument 100 to allow draining, but fluid flow should be controlled. The fluid's movement to areas sensitive to fluid, such as components inside the housing 102, can be accelerated by insufflation pressure and gravity. FIGS. 27A-27R show example designs to slow fluid movement. FIGS. 27A-27R show features to control fluid ingress into and egress from the housing 102 described herein, according to aspects of the present disclosure. For instance, a first goal is to prevent fluid from entering the housing 102 at all (i.e., prevent ingress; see FIGS. 27O, 27P, 27Q, and 27R for example solutions to ingress). If fluid does enter the housing 102, a secondary goal is to retain the fluid within the housing 102 (i.e., prevent egress; see FIGS. 27A-27N, and 27Q-27R for example solutions to egress).

Turning now to FIG. 27A, the example shows certain fluid management cavities 1002 surrounded by, or defined by, walls 1004. One way to prevent unintended fluid egress is to modify the housing 102 (one of or both of the first section 110 or second section 112) to have walls 1004 to minimize the overspill of liquid out of bottom of the housing 102. Those walls 1004, in addition to ribs that provide structure to the rest of the housing 102, can be used to create cavities 1002 of space to pool the liquid into predefined areas. The cavities 1002 can also accommodate a material capable of retaining any fluid entering the cavity 1002. FIG. 27B shows absorbents 1006 positioned in individual cavities 1002. The absorbent 1006 can be any type of material to hold the fluid. For example, the absorbent 1006 can be a hydrophilic fiber component that has a high wettability and does not expand greatly in size as it absorbs fluid-such materials can be suited to attract the fluid and hold it via surface tension within the fibrous volume. These materials can include polyethylene, polystyrene, polyvinylchloride, polytetrafluorethylene, polydimethylsiloxane, polyesters, and polyurethanes foams, meshes, fibers and the like.

Figure 27C:
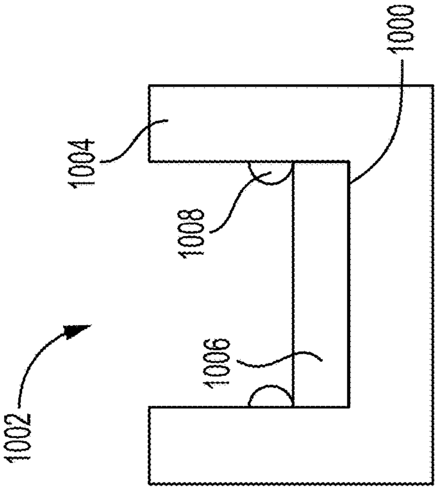
FIGS. 27C, 27D, 27E, 27F, and 27G show example designs for walls of the cavities described with respect to FIG. 27A, according to aspects of the present disclosure.
Figure 27D:
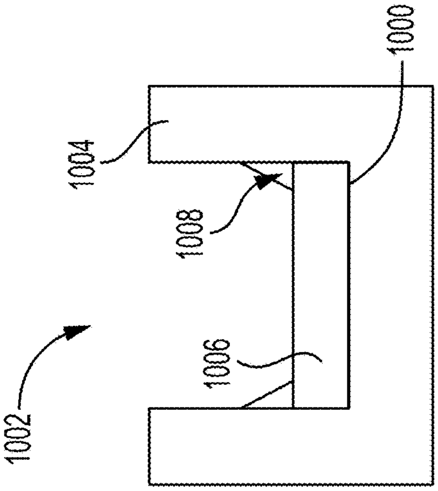
Figure 27E:
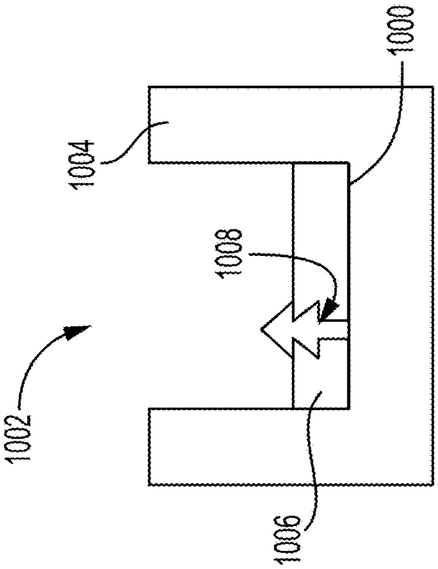
Figure 27F:
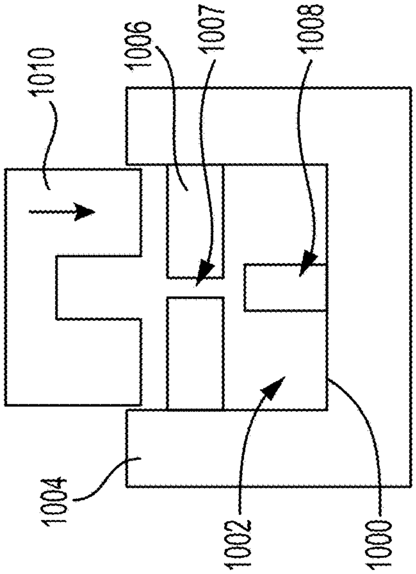
Figure 27G:
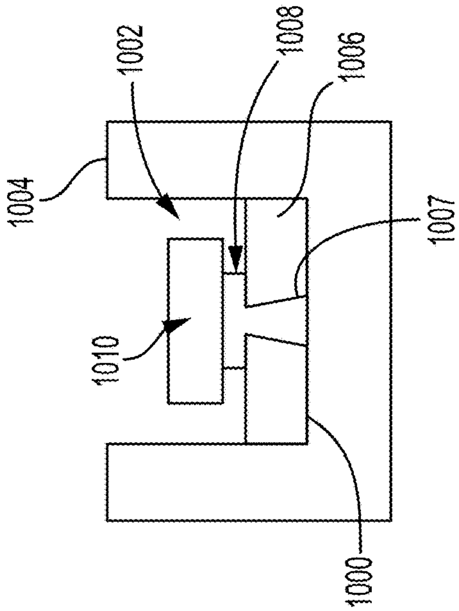

FIGS. 27C-27G show example designs for walls of the cavities 1002 described with respect to FIG. 27A, according to aspects of the present disclosure. In FIG. 27C, the walls 1004 that define each cavity 1002 include retention features 1008, and in the case of this example the retention features 1008 are rounded undercut features. The absorbent 1006 can be positioned in the cavity 1002 and be held in place to an interior surface 1000 of the housing 102 by the rounded retention features 1008 of the adjacent wall 1004. In FIG. 27D, the retention features 1008 are also undercut feature but in this example are one-way undercuts. When inserting the absorbent 1006 into the cavity 1002, the absorbent 1006 will slide down a ramp on one side of the retention features 1008 and be locked into place to an interior surface 1000 of the housing 102 by the flat underside of the undercut retention features 1008. In FIG. 27E, the retention features 1008 include a barb such that, once the absorbent 1006 is inserted into the cavity 1002, the barb will hold the absorbent 1006 in place to an interior surface 1000 of the housing 102. In FIG. 27F, the retention feature 1008 is a pin extending from the base of the cavity 1002. As can be seen an insertion tool 1010 can be used in this example to seat the absorbent 1006. The absorbent 1006 is pushed onto the pin, which is the retention feature 1008 in this example, allowing the pin to slide through an aperture 1007 in the absorbent 1006. Once seated, the insertion tool 1010 can be removed and the pin will hold the absorbent 1006 in place to an interior surface 1000 of the housing 102. In FIG. 27G, the retention feature 1008 is a rivet extending from the base of the cavity 1002. As can be seen, an insertion tool 1010 can be used in this example to actuate the rivet to hold the absorbent 1006 in place to an interior surface 1000 of the housing 102. As will be appreciated, any of the examples shown in FIGS. 27C-27G can be used in combination with any of the other examples.

Figure 27I:
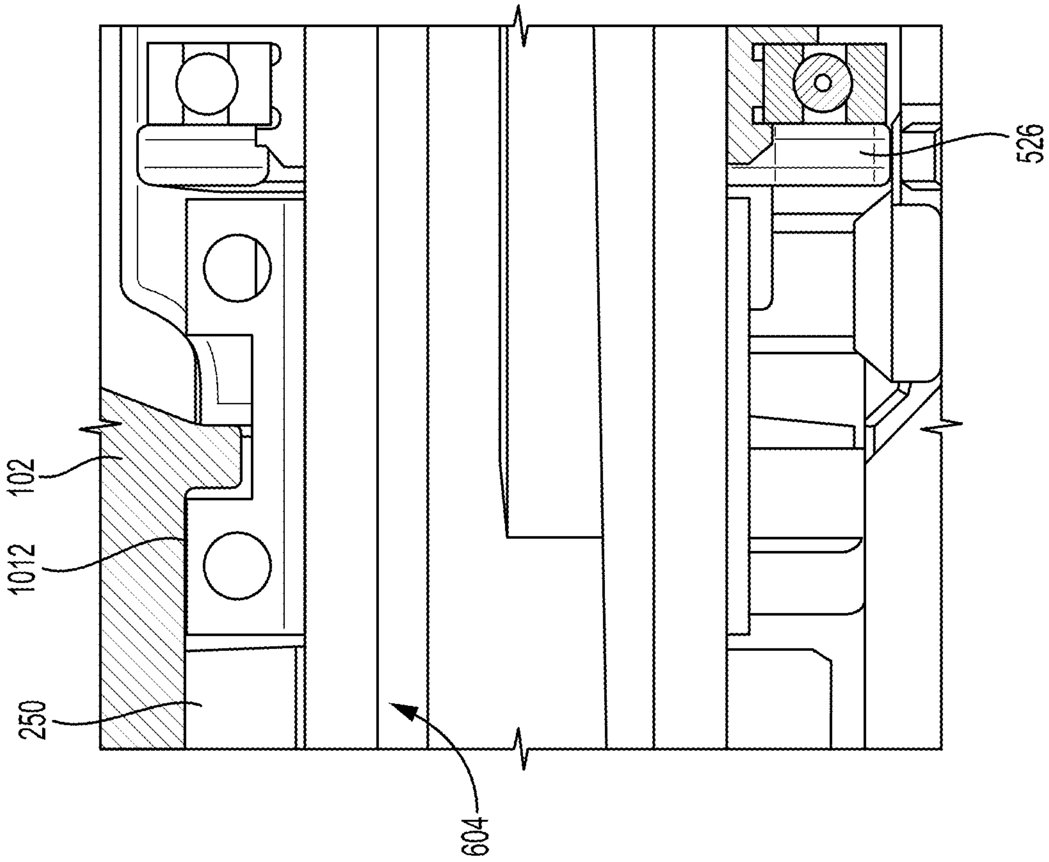
FIG. 27I shows a cross sectional view of the positioning of the sleeve, according to aspects of the present disclosure.
Figure 27H:
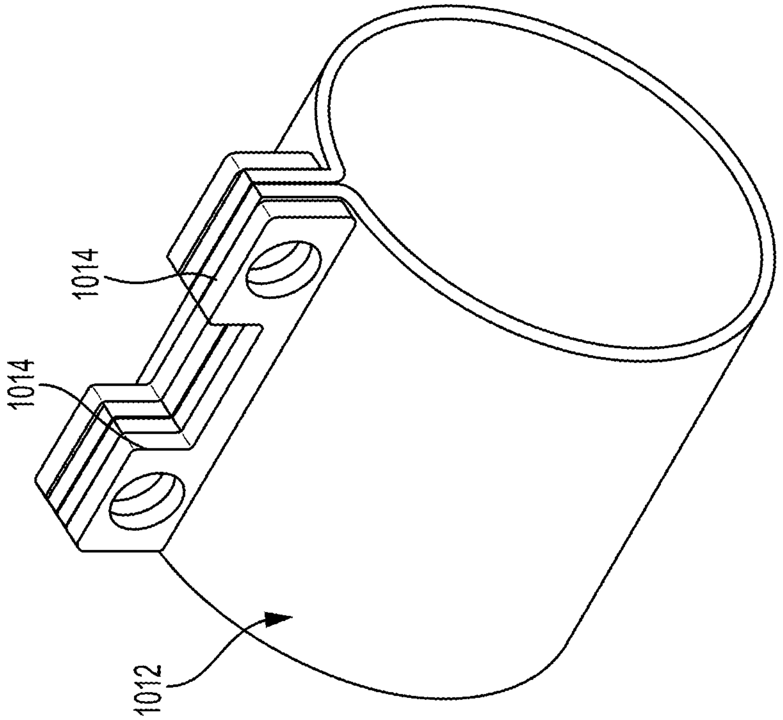
FIG. 27H shows an example fluid management sleeve.

FIG. 27H shows an example fluid management sleeve 1012, according to aspects of the present disclosure. The sleeve 1012 can be positioned such that it is close to a known area for fluid ingress, which is where the nose 1034 of the housing 102 meets the closure tube 212 (see FIG. 2A). The sleeve 1012 can be positioned on the shaft 604 between the closure yoke 250 and the articulation bushings (first articulation bushing 526 is shown in the cross section of FIG. 27I, but the sleeve 1012 could equally be applied to the examples shown with first articulation bushing 426 and second articulation bushing 428). FIG. 27I shows the positioning of the sleeve 1012. As will be appreciated, the respective articulation bushings described herein are designed to move proximally and distally to effect articulation, and as such a length of the sleeve 1012 can be such that it is shorter than a distance between the closure yoke 250 and the most-distal position of the respective articulation bushing(s). The sleeve 1012 can be affixed to the housing 102, for example by use of one or more sinching plates 1014 that can be positioned between grooves within the housing 102. The sleeve 1012 can be made of a hydrophilic fiber component that has a high wettability and does not expand greatly in size as it absorbs fluid-such materials can be suited to attract the fluid and hold it via surface tension within the fibrous volume. These materials can include polyethylene, polystyrene, polyvinylchloride, polytetrafluorethylene, polydimethylsiloxane, polyesters, and polyurethanes foams, meshes, fibers and the like.

Figure 27K:
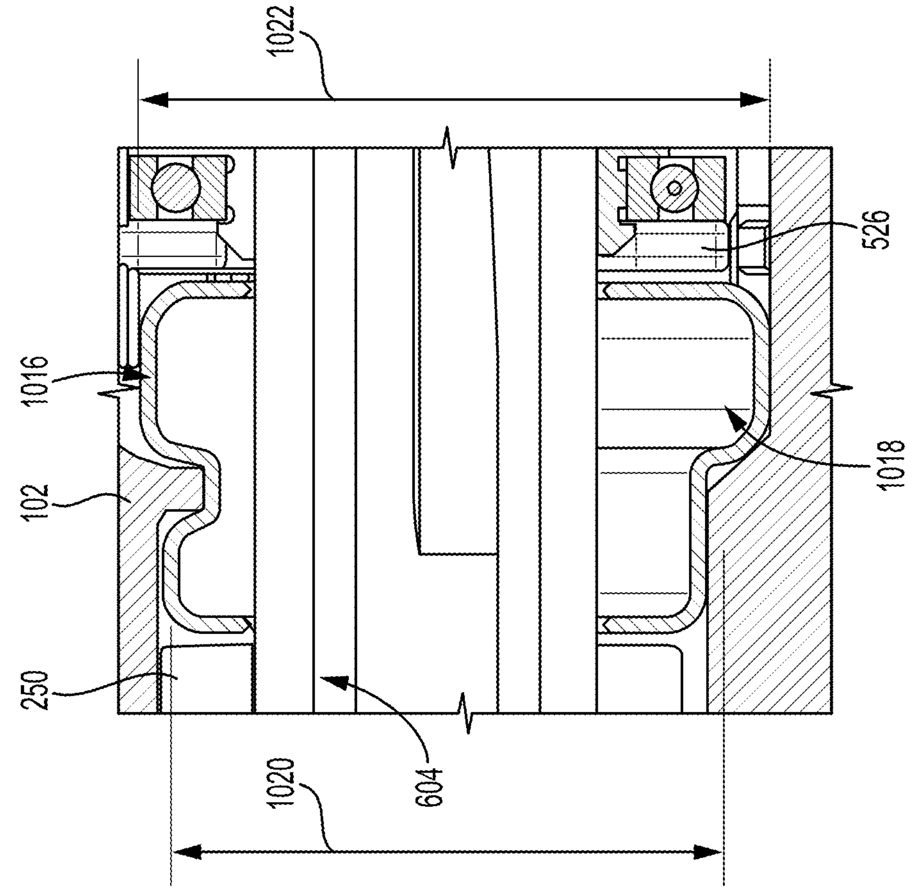
FIG. 27K shows a cross sectional view of the positioning of the collar of FIG. 27J, according to aspects of the present disclosure.
Figure 27J:
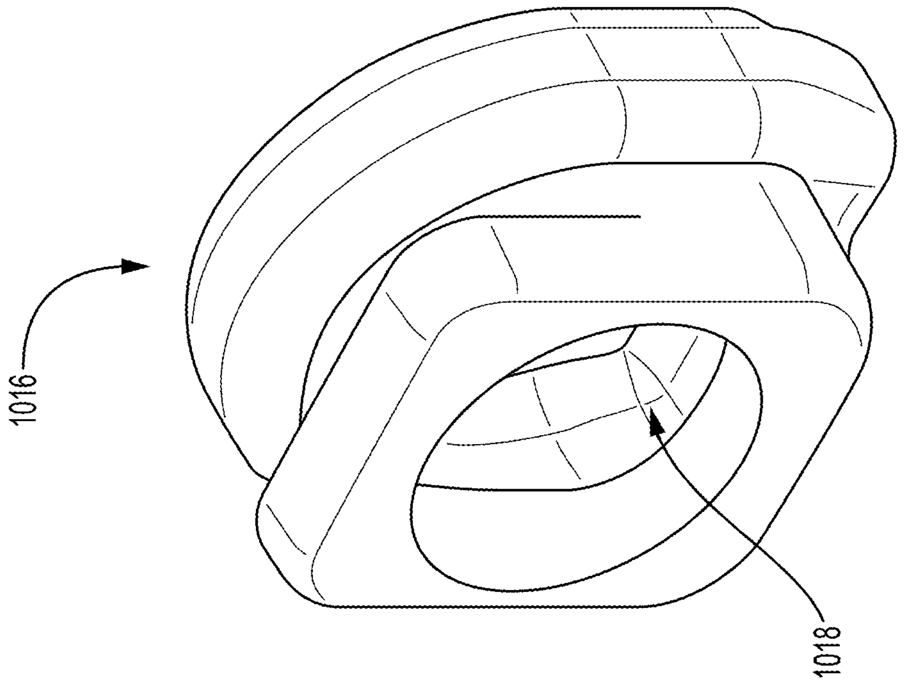
FIG. 27J shows an example fluid management trap collar.
Figure 27L:
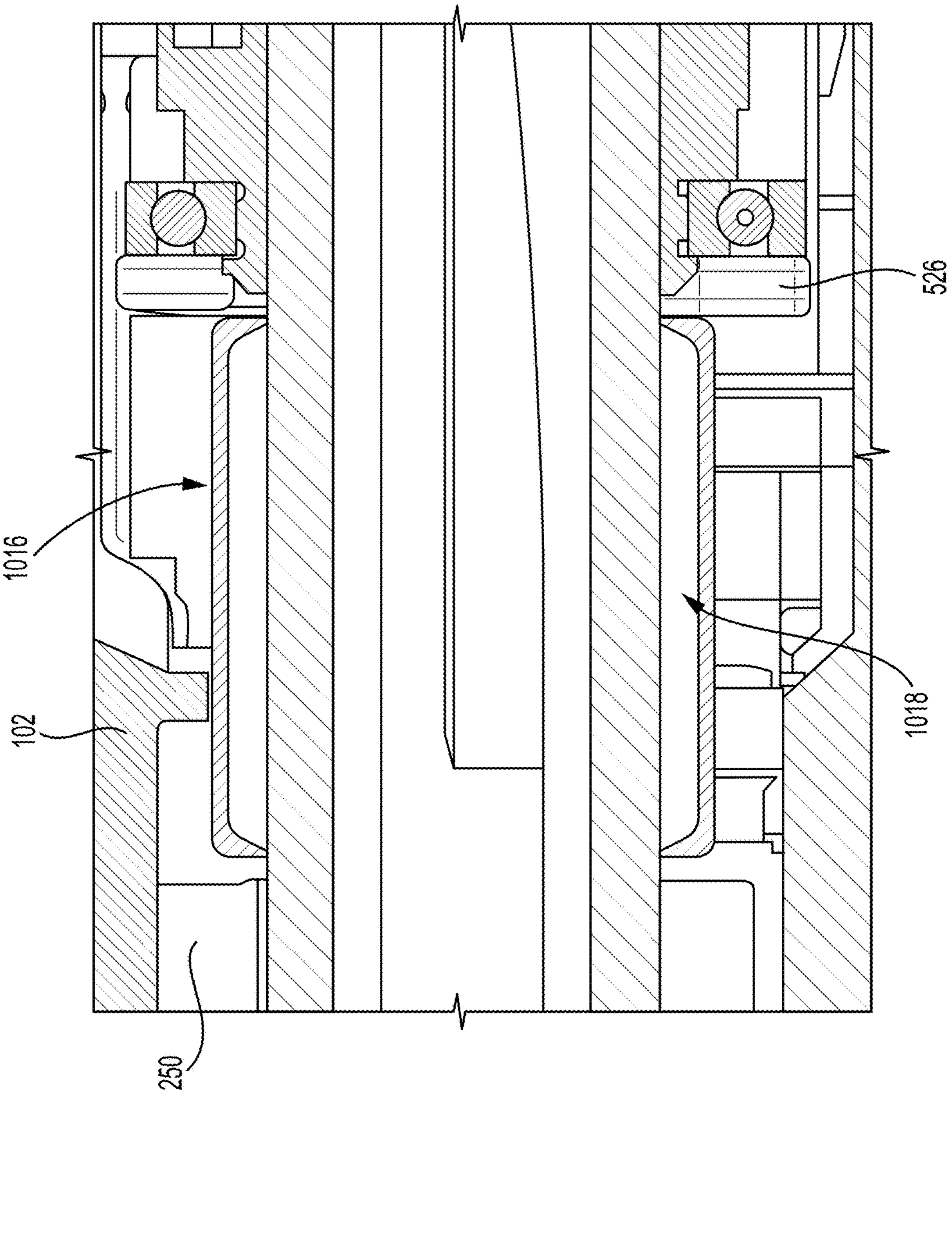
FIG. 27L is a similar example of a trap collar but without a separately defined trap.

FIG. 27J shows an example fluid management trap collar 1016, according to aspects of the present disclosure. The trap collar 1016 can be positioned such that it is close to a known area for fluid ingress, which is where the nose 1034 of the housing 102 meets the closure tube 212 (see FIG. 3). The trap collar 1016 can be positioned on the shaft 604 between the closure yoke 250 and the articulation bushings (first articulation bushing 526 is shown in the cross section of FIG. 27K, but the trap collar 1016 could equally be applied to the examples shown with first articulation bushing 426 and second articulation bushing 428). FIG. 27K shows the positioning of the trap collar 1016. As will be appreciated, the respective articulation bushings described herein are designed to move proximally and distally to effect articulation, and as such a length of the trap collar 1016 can be such that it is shorter than a distance between the closure yoke 250 and the most-distal position of the respective articulation bushing(s). The trap collar 1016 can be made of an elastomeric material that can hold a volume of fluid therein and/or redirect the fluid to a different location within the housing 102. To capture the pooled liquid, the trap collar 1016 encircles the shaft 604. The stretch of the elastomeric material creates a seal against the shaft 604. In the example shown in FIGS. 27J and 27K, the trap collar has a defined trap 1080 wherein a width 1022 of the trap collar 1016 proximate the trap 1018 is larger than a width 1020 of the trap collar 1016 outside of the location of the trap 1018. Fluid can pool into the trap 1018. FIG. 27L is a similar trap collar 1016, but is cylindrical and does not have a separately defined trap 1018—the entire length of the trap collar 1016 can be considered a trap 1018.

Figure 27N:
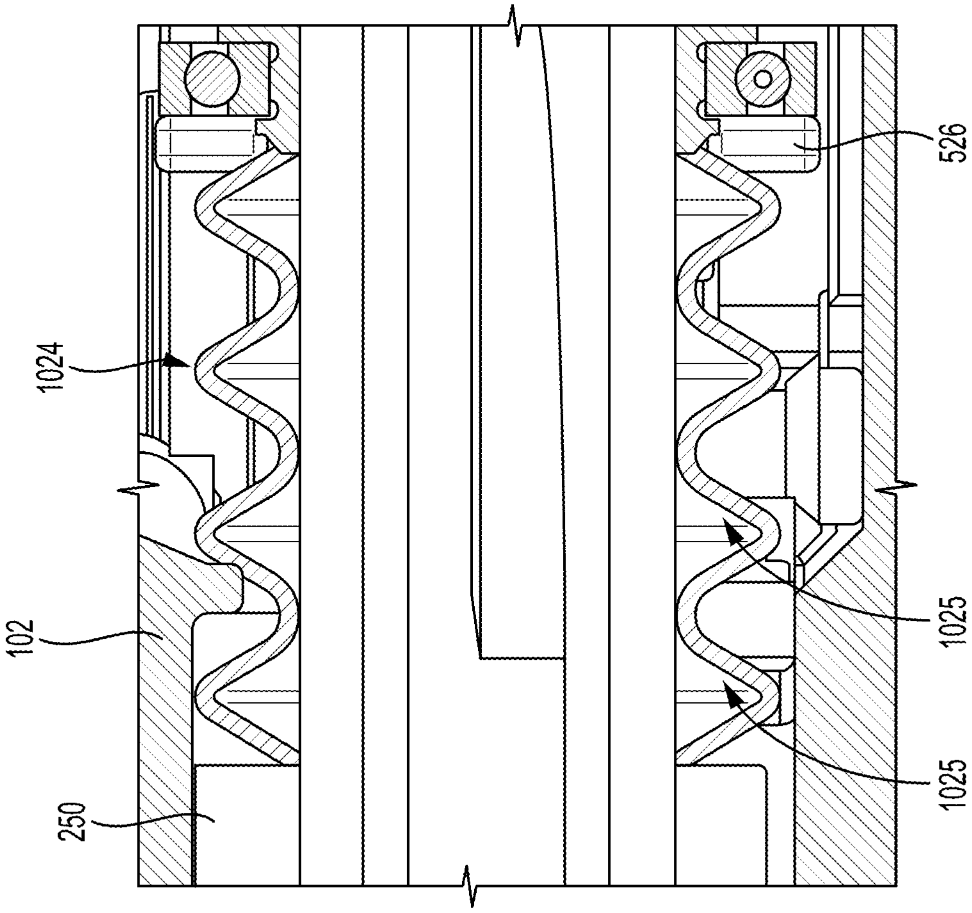
FIG. 27N shows a cross sectional view of the positioning of the collar, according to aspects of the present disclosure.
Figure 27M:
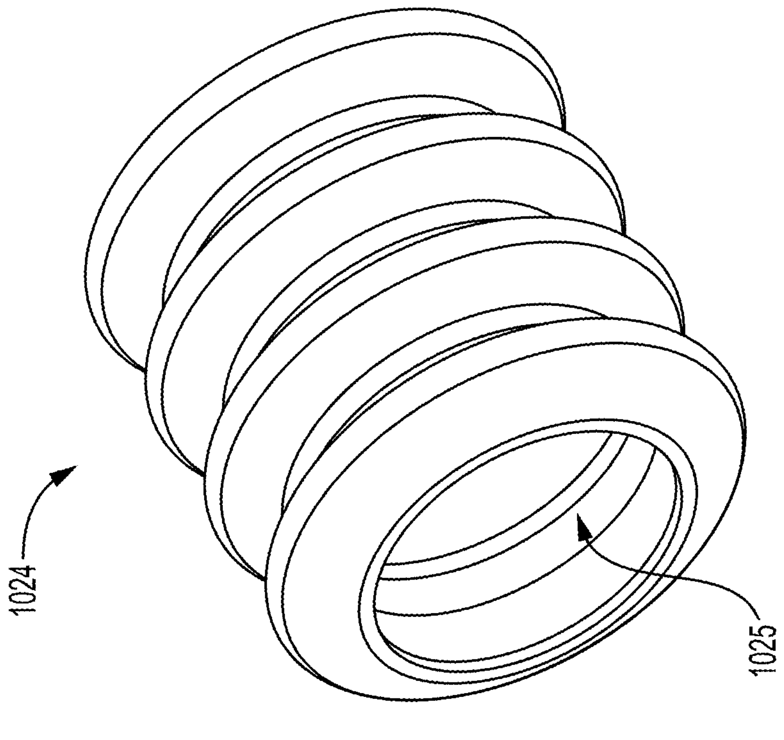
FIG. 27M shows an example fluid management flex collar.

FIG. 27M shows an example fluid management flex collar 1024, according to aspects of the present disclosure. The flex collar 1024 can be positioned such that it is close to a known area for fluid ingress, which is where the nose 1034 of the housing 102 meets the closure tube 212 (see FIG. 3). The flex collar 1024 can be positioned on the shaft 604 between the closure yoke 250 and the articulation bushings (first articulation bushing 526 is shown in the cross section of FIG. 27N, but the flex collar 1024 could equally be applied to the examples shown with first articulation bushing 426 and second articulation bushing 428). FIG. 27N shows the positioning of the flex collar 1024. As will be appreciated, the respective articulation bushings described herein are designed to move proximally and distally to effect articulation. In this example, separate ends of the flex collar 1024 can be connected to the closure yoke 250 and respective articulation bushing(s) 426, 526, and the flex collar 1024 can expand and contract (like an accordion) with the axial movement of the articulation bushing(s) 426, 526. The flex collar 1024 can have an accordion-style shape, providing a plurality of traps 1025 to capture fluid.

Figure 27O:
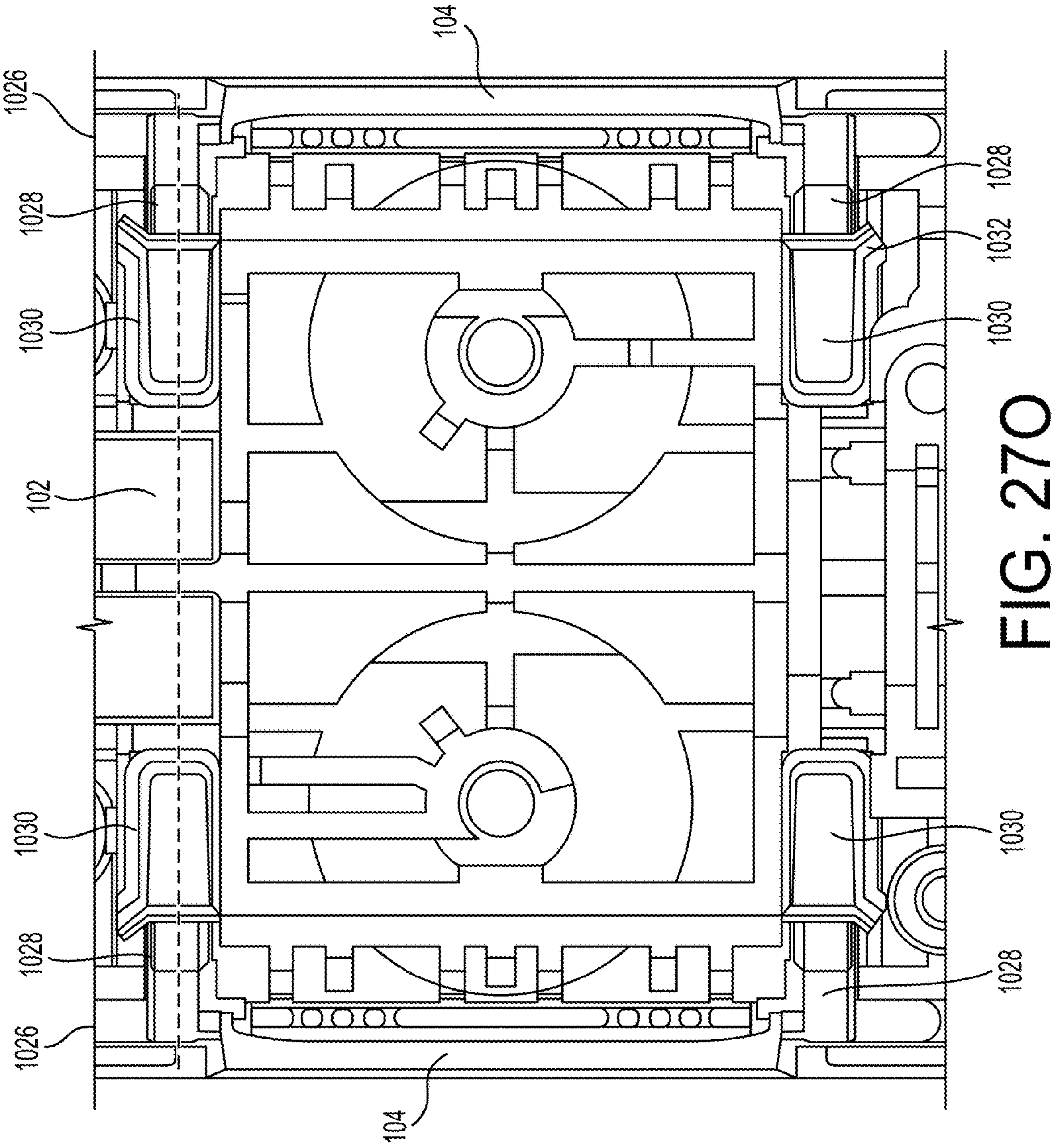
FIG. 27O shows example fluid diverters for a housing, according to aspects of the present disclosure.

FIG. 27O shows example fluid diverters 1030 for a housing 102, according to aspects of the present disclosure. Certain parts of the housing 102 can have openings that can allow fluid to flow into the housing 102. One such opening includes the one or more delatching bodies 1028 in one or more openings 1029 (also shown in FIG. 2A) that help the surgical instrument 100 detach from a robotic arm (not shown). These delatching bodies 1028 are connected to a release hinge 1026, and the release hinge 1026 is connected to the release button 104. Actuation of the release button 104 can, therefore, move the delatching bodies 1028. As such, fluid diverters 1030 can be positioned to cover at least a portion of the delatching bodies 1028 and the holes in the housing 102 that correspond to the delatching bodies 1028. The fluid diverters 1030 can be elastomeric bodies that that can be trapped, glued, welded, etc. in place. When the delatching bodies 1028 need to occupy the same space, the fluid diverters 1030 can flap or stretch to provide space for the delatching bodies 1028. Either position, though, allows the fluid to fill into an adjacent cavity (e.g., the cavities 1002 described with respect to FIG. 27A) and not egress from the housing 102. Each delatching bodies 1028 can channels 1032 that can divert fluid to adjacent cavities.

Figure 27P:
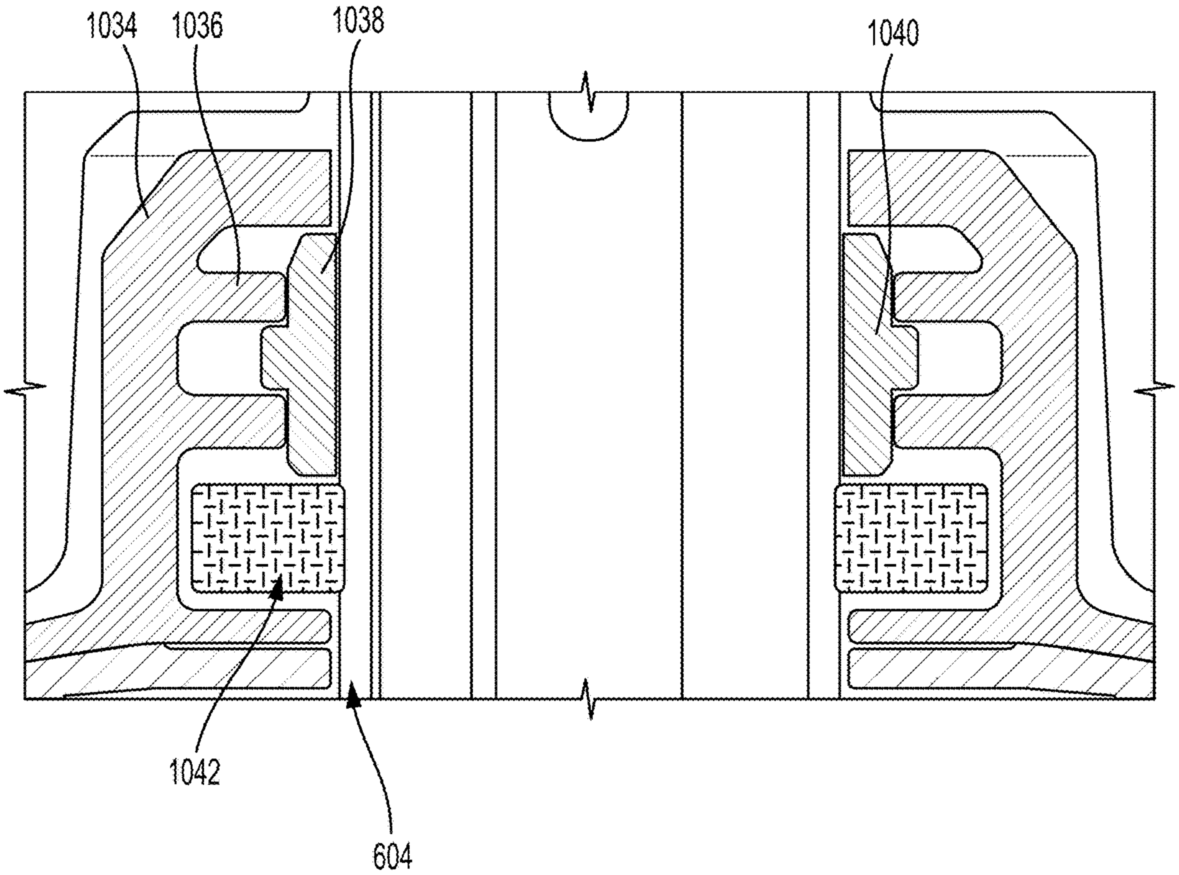
FIG. 27P shows a fluid management bushing for a housing, according to aspects of the present disclosure.
Figure 27R:
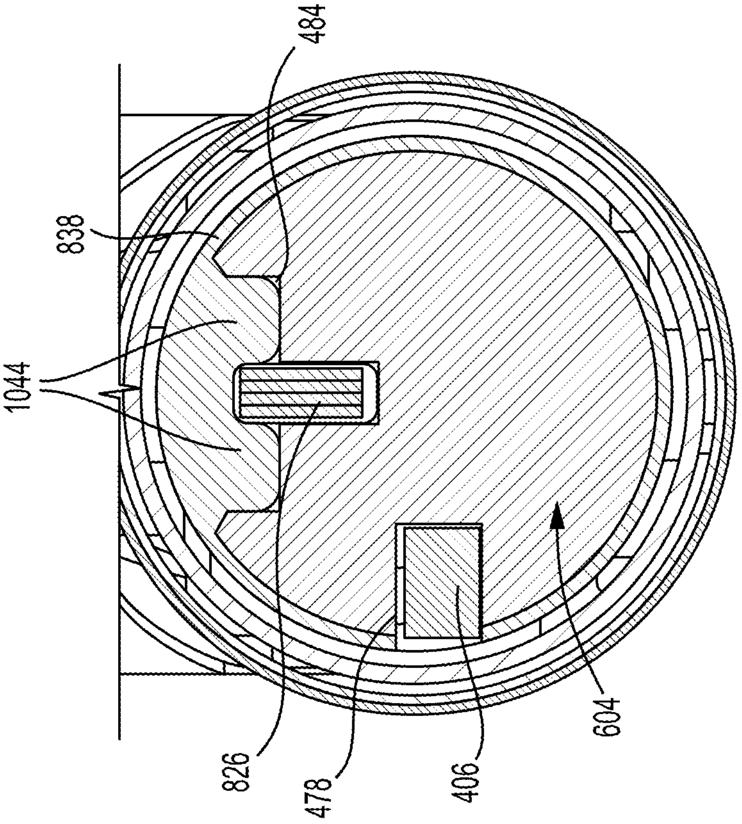

FIG. 27P shows a fluid management bushing 1038 for a housing, according to aspects of the present disclosure. The bushing 1038 can be positioned such that it is close to a known area for fluid ingress, which is where the nose 1034 of the housing 102 provides a tube opening 1035 for the closure tube 212 (see FIG. 3). The example bushing 1038 works like a traditional O-ring that take up the radial gap between the housing 102 and closure tube 212. The bushing 1038 can be positioned between adjacent flanges 1036 in the nose 1034 of the housing 102. The bushing 1038 may also not be a standard O-ring, but can also have bushing flanges 1040 that extend into areas between adjacent flanges 1036 in the nose 1034. Alternatively or additionally, an absorbent ring 1042 can be positioned to surround the closure tube 212 to prevent fluid movement through the nose 1034 of the housing 102. The absorbent ring 1042 can be similar to the absorbent 1006 described herein. An O-ring can also be positioned at any point between the closure tube 212 and the shaft 604.

Figure 27Q:
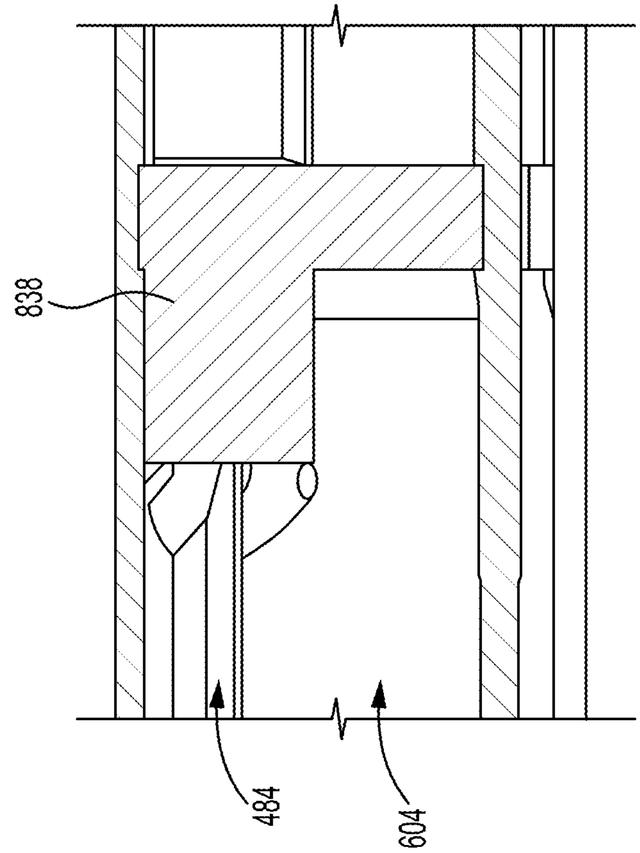
FIG. 27Q shows an example fluid management seal extension for a knife insert retainer.

FIG. 27Q shows an example fluid management seal extension 1044 for a knife insert retainer 838 (see also FIG. 31). FIG. 27R shows a cross sectional view of the positioning of the seal extension 1044, according to aspects of the present disclosure. The challenge with a simple O-ring is that it does not seal where there are discontinuities in the circular diameter of the shaft 604, such as discontinuities for the band slot 484 for the bands 826, or for the rod groove 478 for the articulation rod 406. To accommodate this a seal, for example a seal extending from the knife insert retainer 838, can include one or more seal extensions 1044 extending therefrom. In FIG. 27R, there is a C-shape seal extensions 1044 extending within the band slot 484. The main job of the knife insert retainer 838 is to provide the knife with solid boundaries laterally, to minimize Euler buckling of the bands 826. By adding a feature like "C-shaped" seal extensions 1044 to that section, the seal extensions 1044 will plug the space that fluid can flow near the bands 826.

Control Device and Methods

Figure 28:
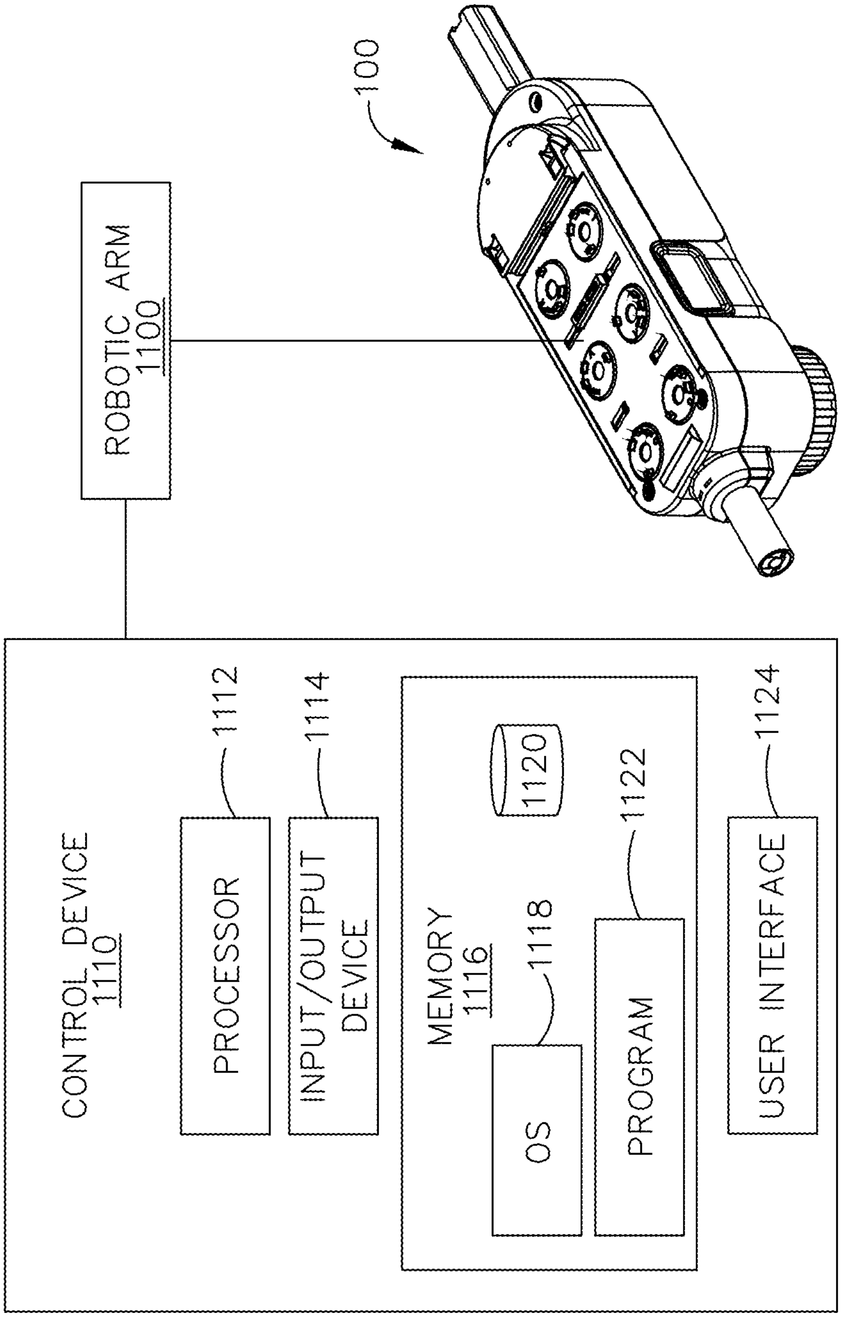
FIG. 28 is a block diagram of a control device, robotic arm, and the surgical instrument, according to aspects of the present disclosure.

FIG. 28 is an illustration of an example control device 1110 for controlling the robotic arm 1100 and the surgical device 100. As shown, the control device 1110 can include a processor 1112; an input/output device; and a memory 1116 containing an operating system (OS) 1118, a storage device 1120, which can be any suitable repository of data, and a program 1122. The input/output device can be configured to receive and to output commands to control the robotic arm 1100 and the surgical device 100. The control device 1110 can include a user interface (U/I) 1124 device for receiving user input data (e.g., from a physician, technician, etc.), such as data representative of a click, a scroll, a tap, a press, movement of a control lever, or typing on an input device that can detect tactile inputs. The control device 1110 can include a display.

The control device 1110 can include a peripheral interface, which can include the hardware, firmware, and/or software that enables communication with various peripheral devices, such as media drives (e.g., magnetic disk, solid state, or optical disk drives), other processing devices, or any other input source used in connection with the instant techniques. The peripheral interface can include a serial port, a parallel port, a general-purpose input and output (GPIO) port, a game port, a universal serial bus (USB), a micro-USB port, a high definition multimedia (HDMI) port, a video port, an audio port, a Bluetooth™ port, a WiFi port, a near-field communication (NFC) port, another like communication interface, or any combination thereof to communicate with other devices via wired or wireless connections or networks, whether local or wide area, private or public, as known in the art. A power source can be configured to provide an appropriate alternating current (AC) or direct current (DC) to power components.

The processor 1112 can include one or more of an application specific integrated circuit (ASIC), programmable logic device, microprocessor, microcontroller, digital signal processor, co-processor or the like or combinations thereof capable of executing stored instructions and operating upon stored data. The memory 1116 can include one or more suitable types of memory (e.g., volatile or non-volatile memory, random access memory (RAM), read-only memory (ROM), programmable read-only memory (PROM), erasable programmable read-only memory (EPROM), electrically erasable programmable read-only memory (EEPROM), magnetic disks, optical disks, floppy disks, hard disks, removable cartridges, flash memory, a redundant array of independent disks (RAID), and the like) for storing files including the operating system 1118, application programs 1122 (including, for example, a web browser application, a widget or gadget engine, and or other applications, as necessary), executable instructions and data. One, some, or all of the processing techniques described herein can be implemented as a combination of executable instructions and data within the memory 1116.

The processor 1112 can be one or more known processing devices, such as a microprocessor from the Pentium™ family manufactured by Intel™, the Turion™ family manufactured by AMD™, or the Cortex™ family or SecurCore™ manufactured by ARM™ to provide just a few examples. The processor 1112 can constitute a single-core or multiplecore processor that executes parallel processes simultaneously. For example, the processor 1112 can be a single-core processor that is configured with virtual processing technologies. One skilled in the art will understand that other types of processor arrangements could be implemented that provide for the capabilities disclosed herein.

The control device 1110 can include one or more storage devices 1120 configured to store information used by the processor 1112 (or other components) to perform at least some of the functions disclosed herein. As an example, the control device 1110 can include memory 1116 that includes instructions to enable the processor 1112 to execute one or more applications, network communication processes, and any other type of application or software known to be available on computer systems. Alternatively, the instructions, application programs, or other software can be stored in an external storage and/or can be available from a remote memory over a network. The one or more storage devices can be a volatile or non-volatile, magnetic, semiconductor, tape, optical, removable, non-removable, or other type of storage device or tangible computer-readable medium.

The control device 1110 can include memory 1116 that includes instructions that, when executed by the processor 1112, perform one or more processes consistent with the functionalities disclosed herein. Methods, systems, and articles of manufacture consistent with disclosed embodiments are not limited to separate programs or computers configured to perform dedicated tasks. For example, the control device 1110 can include memory 1116 that can include one or more programs 1122 to perform one or more functions of the disclosed technology. For example, the control device 1110 can access one or more programs 1122, that, when executed, perform at least one function disclosed herein. One or more programs 1122 can be configured to receive input from a user (e.g., a physician, a technician, etc.) and cause the control device 1110 to output one or more control signals to the robotic arm 1100. The one or more programs 1122 can be configured to cause the user interface 1124 to display images indicative of a function or condition associated with the robotic arm 1100.

The memory 1116 of the control device 1110 can include one or more memory devices that store data and instructions used to perform one or more of the methods and features disclosed herein. The memory 1116 can include software components that, when executed by the processor 1112, perform one or more processes consistent with those disclosed herein. The control device 1110 can include any number of hardware and/or software applications that are executed to facilitate any of the operations. The one or more I/O interfaces 1114 can be utilized to receive or collect data and/or user instructions from a wide variety of input devices. Received data can be processed by one or more computer processors 1112 as desired in various implementations of the disclosed technology and/or stored in one or more memory devices.

While the control device 1110 has been described above for implementing the techniques described herein, those skilled in the art will appreciate that other functionally equivalent techniques can be employed. For example, as known in the art, some or all of the functionality implemented via executable instructions can also be implemented using firmware and/or hardware devices such as application specific integrated circuits (ASICs), programmable logic arrays, state machines, etc. Furthermore, the control device 1110 can include a greater or lesser number of components than those illustrated and/or described above.

Figure 29:
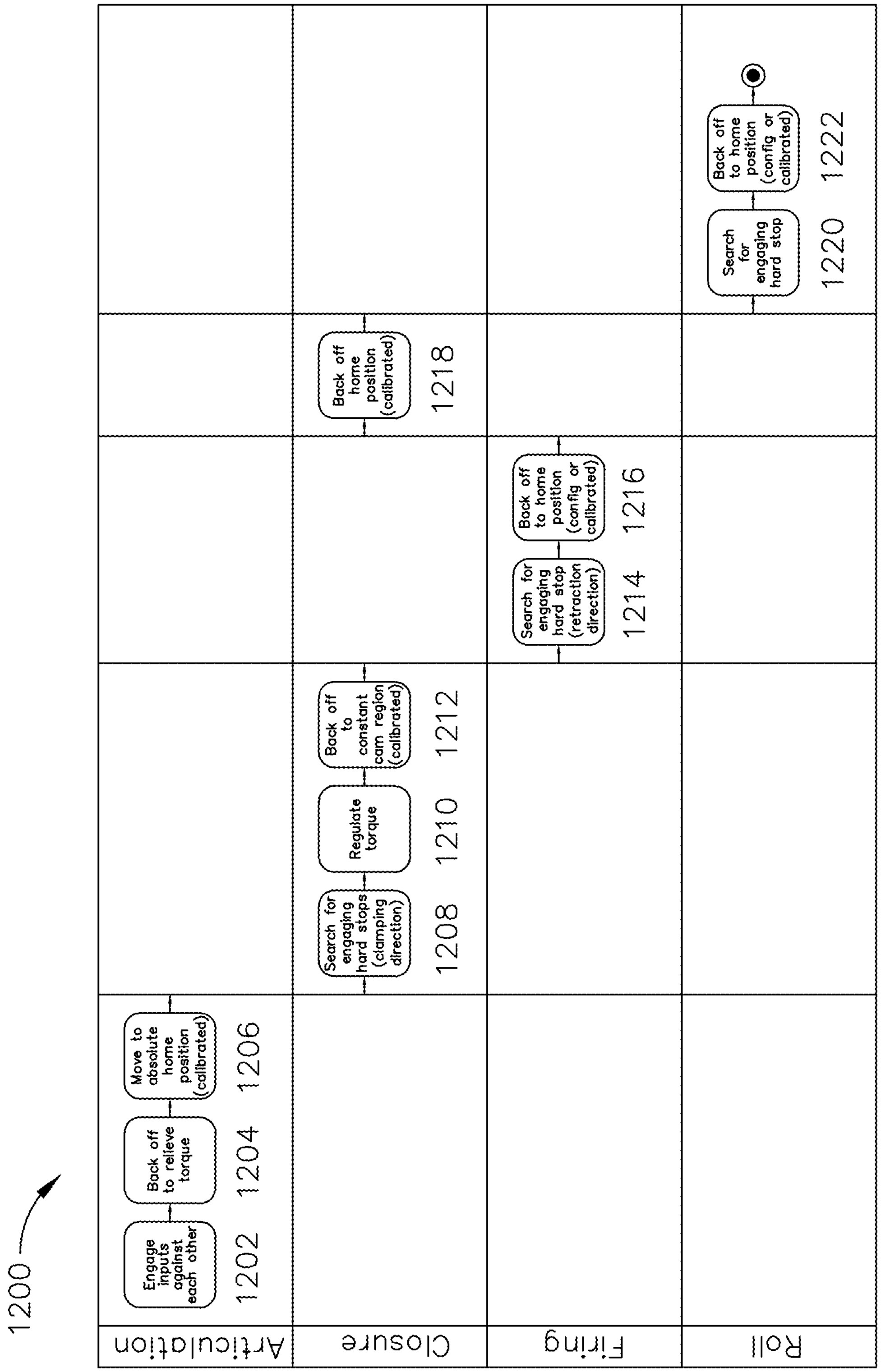
FIG. 29 is a flow chart depicting a method of engaging and homing the surgical instrument, according to aspects of the present disclosure.

Turning now to FIG. 29, a method 1200 of engaging and homing the surgical instrument 100 is shown and described. The term "engaging" refers to the act of aligning and mating the input pucks 202-802 of the surgical instrument 100 with corresponding pucks on a sterile adapter and the robotic arm 1100. Although not shown, the sterile adapter can be a component configured to interface with the surgical instrument 100 and the robotic arm 1100 and to keep the robotic arm 1100 sterile. The term "homing" refers to defining which motor positions correspond to zero joint positions and moving the joints to those positions (i.e., moving the joint to a home position).

As shown in FIG. 29, the method 1200 includes engaging and homing several of the subsystems shown and described herein. For example, the method 1200 can be utilized after first attaching the surgical instrument 100 to a robotic arm 1100. The method 1200 can include engaging and homing the articulation subsystem 400, the closure subsystem 200, the transection subsystem 800, and the roll subsystem 600. Although shown and described as being performed in a particular order, it will be understood that the method 1200 is not so limited and can be performed in various orders and include other intervening steps not shown and described herein.

The method 1200 includes engaging 1202 inputs (e.g., first and second articulation input pucks 402, 404) of the articulation subsystem 400 such that the inputs, through the various other components of the articulation subsystem 400, provide opposing forces on each other. For example, if the articulation subsystem 400 includes two racks 414, 418 the method 1200 can include turning the first articulation input puck 402 and the second articulation input puck 404 in opposite directions. On the other hand, if the articulation subsystem 400 includes a single rack 414C, the method 1200 can include turning the first articulation input puck 402 and the second articulation input puck 404 in the same direction. By turning the first articulation input puck 402 and the second articulation input puck 404 in directions to cause opposing forces on each other, the control device 1110 can detect when the gears of the articulation subsystem 400 have bottomed out (e.g., via torque sensors, force sensors, or other suitable sensors) and the first articulation input puck 402 and the second articulation input puck 404 can engage with the corresponding pucks of the robotic arm 1100 and the sterile adapter. Stated otherwise, the method 1200 can include rotating a first input puck and a second input puck of the robotic 1100 arm until a predetermined threshold indicator on both the first input puck and the second input puck is detected, the first input puck and the second input puck being in mechanical communication with an articulation subsystem of the surgical instrument. The threshold indicator, for example, can be a threshold force, a threshold current, a threshold voltage, or other similar indicator.

The method 1200 includes turning 1204 the first articulation input puck 402 and the second articulation input puck 404 to relieve torque and moving 1206 the first articulation input puck 402 and the second articulation input puck 404 to a predetermined articulation home position.

The method 1200 includes turning 1208 the first closure puck 202 and the second closure puck 204 until the control device 1110 determines that the closure subsystem 200 has encountered a hard stop (e.g., the anvil 152 is fully closed). Stated otherwise, the method 1200 can include rotating one or more pucks of the closure subsystem until a second predetermined threshold indicator is detected. The threshold indicator, for example, can be a threshold force, a threshold current, a threshold voltage, or other similar indicator. In doing so, the first closure puck 202 and the second closure puck 204 engage with the corresponding pucks of the robotic arm 1100 and the sterile adapter and the control device 1110 will be able to determine the position of the first closure puck 202 and the second closure puck 204. The method 1200 includes regulating 1210 the torque by causing the first closure puck 202 and the second closure puck 204 to rotate only to a predetermined force (e.g., as detected by torque sensors, force sensors, or other suitable sensors) and moving 1212 the closure subsystem 200 to the constant force region 282.

The method 1200 includes moving 1214 the transection puck 802 of the transection subsystem 800 in a retraction direction until a hard stop is detected (e.g., as detected by torque, force, current, or other suitable sensors). The hard stop can be or include a stop at an end of travel of the firing rack 816, a stop feature formed into the knife 126, the distal hard stop 819, or other similar components to determine that the transection subsystem 800 has fully retracted. Stated otherwise, the method 1200 includes rotating an input puck of the transection subsystem until a third predetermined threshold indicator is detected. The threshold indicator, for example, can be a threshold force, a threshold current, a threshold voltage, or other similar indicator. In doing so, the transection puck 802 engages with the corresponding pucks of the robotic arm 1100 and the sterile adapter and the control device 1110 will be able to determine the position of the transection puck 802. The method 1200 includes backing off 1216 or otherwise moving the transection puck 802 in an opposite direction to a predetermined transection home position. As will be appreciated, determining the home position of the transection subsystem 800 while the closure subsystem 200 is in the constant force region 282 can help to ensure the home position of the transection subsystem 800 is determined while the surgical instrument 100 is in a clinically relevant position.

Once engaging and homing of the transection subsystem 800 is complete, the method 1200 further includes backing off 1218 or otherwise moving the first closure puck 202 and the second closure puck 204 of the closure subsystem 200 in an opposite direction to a predetermined closure home position.

The method 1200 includes moving 1220 the roll input puck 602 until a hard stop is detected (e.g., as detected by torque, force, or other suitable sensors). Stated otherwise, the method 1200 includes rotating an input puck of the roll subsystem until a predetermined threshold indicator is detected. The threshold indicator, for example, can be a threshold force, a threshold current, a threshold voltage, or other similar indicator. The hard stop, for example, can be or include the housing tab 626 that causes the roll system 600 to stop rotating. In doing so, the roll input puck 602 will engage with the corresponding pucks of the robotic arm 1100 and the sterile adapter and the control device 1110 will be able to determine the position of the roll input puck 602. The method 1200 includes backing off 1222 or otherwise moving the roll input puck 602 in an opposite direction to a predetermined roll home position.

Figure 30:
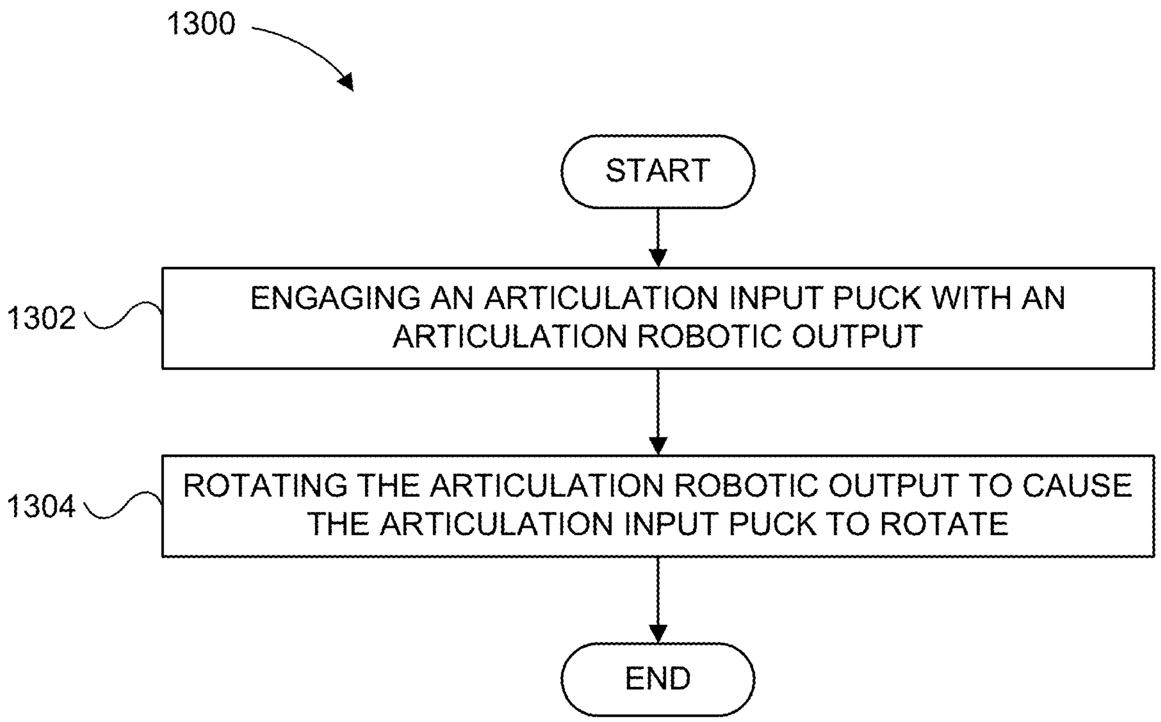
FIG. 30 is a flow chart depicting a method of operating a closure subsystem of a surgical instrument, according to aspects of the present disclosure.

Turning now to FIG. 30, a method 1300 of operating an articulation subsystem (e.g., articulation subsystem 400) of a surgical instrument 100 is shown and described. The method 1300 includes engaging 1302 an articulation input puck (e.g., articulation input puck 402) with an articulation robotic output (e.g., an output of robotic arm 1100) and rotating 1304 the articulation robotic output to cause the articulation input puck to rotate. Rotation of the articulation input puck causes movement of an articulation bushing (e.g., articulation bushing 426, 428, 429) between a distal position and a proximal position to actuate an articulation rod (e.g., articulation rod 406A, 407A, 406B, or 407B). Furthermore, actuation of the articulation rod causes an end effector (e.g. end effector 150) to pivot about an articulation pivot point (e.g., articulation pivot point 466). Method 1300 can end after rotating step 1304, or other steps can be performed in accordance with the examples outlined herein.

Any of the closure subsystems 200, articulation subsystems 400, roll subsystems 600, or transection subsystems 800 described herein can be, respectively, substituted by or combined with any of the closure subsystems 200, articulation subsystems 400, roll subsystems 600, or transection subsystems 800 described in U.S. Provisional Application No. 63/514,972 or those described in U.S. Provisional Application No. 63/634,201, both of which are incorporated herein by reference in their entireties. Any of the end effectors 150 described herein can be substituted by or combined with any of the end effectors 150 described in U.S. Provisional Application No. 63/514,972 or those described in U.S. Provisional Application No. 63/634,201, both of which are incorporated herein by reference in their entireties.

CLAUSES

Examples of the present disclosure can be implemented by any of the following numbered clauses:

Clause 1: An articulation subsystem (400) for a surgical instrument (100) comprising: a rotatable shaft (604) having a longitudinal axis (474); a distal channel retainer (408) coupled to an end effector (150), the distal channel retainer (408) being pivotable about an articulation pivot point (466); an articulation bushing (426, 428) slidable between a proximal position and a distal position along the longitudinal axis (474) of the rotatable shaft (604); an articulation rod (406A, 407A, 406B, or 407B) extending distally from the articulation bushing (426, 428, 429) and coupled at a distal end (472) to the distal channel retainer (408); and a rack (414A, 418A, 414B, 418B, or 414C) movable with respect to the longitudinal axis (474) of the rotatable shaft (604), wherein movement of the rack (414) with respect to the longitudinal axis (474) imparts an axial force onto the articulation bushing (426, 428, 429) moving the articulation bushing (426, 428, 429) between the proximal position and the distal position, and wherein movement of the articulation bushing (426, 428, 429) between the distal position and the proximal position actuates the articulation rod (406A, 407A, 406B, or 407B) causing the distal channel retainer (408) to pivot about the articulation pivot point (466).

Clause 2: The articulation subsystem (400) according to Clause 1, wherein the articulation bushing (426, 428, 429) is rotationally independent of the rack (414A, 418A, 414B, 418B, or 414C).

Clause 3: The articulation subsystem (400) according to Clause 1 or Clause 2 further comprising a rack gear (434) engaged with the rack (414A, 418A, 414B, 418B, or 414C), rotation of the rack gear (434) moving the rack (414A, 418A, 414B, 418B, or 414C) with respect to the longitudinal axis (474).

Clause 4: The articulation subsystem (400) according to Clause 3 further comprising: an articulation input puck (402) engageable with an articulation robotic output; an articulation drive shaft (432) extending from the articulation input puck (402) and comprising a drive gear (430); and a compound gear (442) engaged with the drive gear (430) and the rack gear (434), wherein rotation of the articulation input puck (402) rotates the rack gear (434) moving the rack (414A, 418A, 414B, 418B, or 414C) with respect to the longitudinal axis (474).

Clause 5: The articulation subsystem (400) according to Clause 4, wherein the rack gear (434) is a tube gear, and the articulation drive shaft (432) is positioned within the rack gear (434).

Clause 6: The articulation subsystem (400) according to any of Clauses 3 to 5, wherein the rack (414A, 418A) is positioned at least partially on a side of the rack gear (434) opposite the rotatable shaft (604).

Clause 7: The articulation subsystem (400) according to any of Clauses 3 to 5, wherein the rack (414B, 418B, 414C) is positioned at least partially between the rack gear (434) and the rotatable shaft (604).

Clause 8: The articulation subsystem (400) according to any of Clauses 3 to 7, wherein the rack gear (434) is a first rack gear, the articulation subsystem further comprising: a second rack gear (440) engaged with the rack (414C), rotation of the first rack gear (434) and the second rack gear (440) together moving the rack (414C) with respect to the longitudinal axis (474).

Clause 9: The articulation subsystem (400) according to Clause 8, wherein the first rack gear (434) and the second rack gear (440) simultaneously rotate in opposite directions to cause the rack (414C) to move with respect to the longitudinal axis (474).

Clause 10: The articulation subsystem (400) according to any one of Clauses 1 to 9, wherein the articulation bushing is a first articulation bushing (426), the rack is a first rack (414A, 414B), and the articulation rod is a first articulation rod (406A, 406B), the articulation subsystem further comprising: a second articulation bushing (428) slidable between a second proximal position and a second distal position along the longitudinal axis (474) of the rotatable shaft (604); and a second rack (418A, 418B) movable with respect to the longitudinal axis (474) of the rotatable shaft (604), wherein movement of the second rack (418A, 418B) with respect to the longitudinal axis (474) imparts an axial force onto the second articulation bushing (428) to move the second articulation bushing (428) between the second proximal position and the second distal position, wherein movement of the second articulation bushing (428) between the second distal position and the second proximal position actuates a second articulation rod (406) causing the distal channel retainer (408) to pivot about the articulation pivot point (466).

Clause 11: The articulation subsystem (400) according to Clause 10, wherein movement of the first articulation bushing (426) from the distal position to the proximal position actuates the distal channel retainer (408) in a first direction, and wherein movement of the second articulation bushing (428) from the second distal position to the second proximal position actuates the distal channel retainer (408) in a second direction.

Clause 12: The articulation subsystem (400) according to Clause 10 or Clause 11 further comprising a second rack gear (440) engaged with the second rack (418A, 418B), rotation of the second rack gear (440) moving the second rack (418) with respect to the longitudinal axis (474).

Clause 13: The articulation subsystem (400) according to Clause 12 further comprising: a second articulation input puck (404) engageable with a second articulation robotic output; a second articulation drive shaft (438) extending from the second articulation input puck (404) and comprising a second drive gear (436); and a proximal compound gear (442) engaged with the second drive gear (436) and the second rack gear (440), rotation of the second articulation input puck (404) rotates the second rack gear (440) moving the second rack (418A, 418B) with respect to the longitudinal axis (474).

Clause 14: The articulation subsystem (400) according to Clause 11, wherein the second rack gear (440) is a tube gear, and the second articulation drive shaft (438) is positioned within the second rack gear (440).

Clause 15: The articulation subsystem (400) according to any of Clauses 10 to 14, wherein the first rack (414) is positioned at least partially on a side of the first rack gear (434) opposite the rotatable shaft (604) and the second rack (418) is positioned at least partially on a side of the second rack gear (440) opposite the rotatable shaft (604).

Clause 16: The articulation subsystem (400) according to any of Clauses 8 to 12, wherein the first rack (414) is positioned at least partially between the first rack gear (434) and the rotatable shaft (604) and the second rack (418) is positioned at least partially between the second rack gear (440) and the rotatable shaft (604).

Clause 17: The articulation subsystem (400) according to any one of Clauses 1 to 16, wherein the articulation rod (406A, 406B, 407A, or 407B) is slidable through a rod groove (478) in the rotatable shaft (604).

Clause 18: A closure subsystem (200) for a surgical instrument (100) comprising: a first closure input puck (202) engageable with a first closure robotic output; a cam gear (210) rotatably engaged with the first closure input puck (202); and a yoke pin (216) coupled to a closure tube (212) and movable from a first position to a second position in response to a rotation of the cam gear (210), wherein movement of the yoke pin (216) from the first position to the second position translates the closure tube (212) distally onto an anvil ramp (154) of an anvil (152).

Clause 19: The closure subsystem (200) according to Clause 18, wherein the cam gear (210) comprises a cam track (214), and the yoke pin (216) is positioned within the cam track (214).

Clause 20: The closure subsystem (200) according to Clause 19, wherein the cam track (214) comprises a first zone (222) and a closure zone (224), wherein rotation of the cam gear (210) provides a non-linear movement profile to the yoke pin (216) through the first zone (222) and at least a portion of the closure zone (224).

Clause 21: The closure subsystem (200) according to Clause 20, wherein rotation of the cam gear (210) through the first zone (222) provides faster distal movement of the yoke pin (216) than rotation of the cam gear (210) through the closure zone (224), and rotation of the cam gear (210) through the closure zone (224) provides a greater mechanical advantage to the yoke pin (216) than rotation of the cam gear (210) through the first zone (222).

Clause 22: The closure subsystem (200) according to Clause 20 or Clause 21, wherein the cam track (214) is polynomial in shape and includes a non-linear portion and a constant radius portion.

Clause 23: The closure subsystem (200) according to any one of Clauses 20 to 22, wherein the cam track (214) is a logarithmic spiral.

Clause 24: The closure subsystem (200) according to Clause 18 further comprising a second closure input puck (204) engageable with a second closure robotic output, wherein the cam gear (210) is rotatably engaged with the second closure input puck (204).

Clause 25: The closure subsystem (200) according to Clause 24 further comprising: a first input rod (203) extending from the first closure input puck (202); a first spur gear (206) connected to the first input rod (203) and rotatably engaged with the cam gear (210), the first spur gear (206) turnable by rotation of the first closure input puck (202); a second input rod (205) extending from the second closure input puck (204); and a second spur gear (208) connected to the second input rod (205) and rotatably engaged with the cam gear (210), the second spur gear (208) turnable by rotation of second closure input puck (204).

Clause 26: The closure subsystem (200) according to Clause 18 further comprising a closure yoke (250), wherein the yoke pin (216) extends from the closure yoke (250) and the closure yoke (250) moves with the yoke pin (216).

Clause 27: The closure subsystem (200) according to Clause 26 further comprising a rotatable shaft (604) disposed within the closure yoke (250), the rotatable shaft (604) being rotationally independent of the closure yoke (250).

Clause 28: The closure subsystem (200) according to Clause 18 further comprising a manual closure handle (234) and a manual closure spur gear (230), the manual closure spur gear (230) being turnable by rotation of the manual closure handle (234) and configured to cause rotation of the cam gear (210).

Clause 29: The closure subsystem (200) according to Clause 28, wherein the manual closure handle (234) comprises a manual closure handle grip (236) engaged with the manual closure spur gear (230) and a manual closure handle clip (238) configured to secure the manual closure handle 234) to an enclosure of the surgical instrument (100).

Clause 30: A roll subsystem (600) for a surgical instrument (100) comprising: a rotatable shaft (604) having a longitudinal axis; a first roll input puck (602) engagable with a roll robotic output; a worm gear (608) coupled to and rotatable by the first roll input puck (602); and a worm follower (610) coupled to the rotatable shaft (604), wherein rotation of the first roll input puck (602) causes the worm gear (608) to rotate the worm follower (610) and thereby roll the rotatable shaft (604) about its longitudinal axis.

Clause 31: The roll subsystem (600) according to Clause 30 further comprising a roll stop bushing (618) engaged with the rotatable shaft (604) and comprising a stop (620).

Clause 32: The roll subsystem (600) according to Clause 31 further comprising an outer housing (102) comprising a housing tab (626), the stop (620) contactable with the housing tab (626) providing a degree of rotation for the rotatable shaft (604).

Clause 33: The roll subsystem (600) according to Clause 32 further comprising a follower bushing (622) comprising a follower bushing stop (624), the follower bushing stop (624) contactable with the stop (620) providing the degree of rotation for the rotatable shaft (604).

Clause 34: The roll subsystem (600) according to any of Clauses 30 to 33 further comprising: a stabilization plate (612); a roll bearing plate (616); and a roll bearing (614) disposed between the stabilization plate (612) and the roll bearing plate (616).

Clause 35: The roll subsystem (600) according to any one of Clauses 30-34, wherein the first roll input puck (602) comprises an input shaft (605) extending at least partially through the worm gear (608), the input shaft (605) comprising a flat section (772) positioned to correspond to a worm drive flat (770) of the worm gear (608).

Clause 36: The roll subsystem (600) according to any one of Clauses 30-35, wherein the worm follower (610) comprises a first anti-backlash feature (756, 762, 766), wherein the rotatable shaft (604) comprises a second anti-backlash feature (758, 764, 768), and wherein the first anti-backlash feature (756, 762, 766) is configured to engage with the second anti-backlash feature (758, 764, 768).

Clause 37: The roll subsystem (600) according to any one of Clauses 30-36, wherein the worm follower (610) comprises a first gear flat (756A), the rotatable shaft (604) comprises a first shaft flat (758A), and the first gear flat (756A) is configured to engage with the first shaft flat (758A) to reduce backlash as the worm gear (608) actuates the worm follower (610).

Clause 38: The roll subsystem (600) according to Clause 37, wherein the worm follower (610) comprises a second gear flat (756B), the rotatable shaft (604) comprises a second shaft flat (758B), and wherein the second gear flat (756B) is configured to engage with the second shaft flat (758B) to reduce backlash as the worm gear (608) actuates the worm follower (610).

Clause 39: The roll subsystem (600) according to Clause 37 or Clause 39, wherein first shaft flat (758A) comprises a rod groove (478) sized to accept an articulation rod (406) therethrough.

Clause 40: The roll subsystem (600) according to any one of Clauses 37 to 39, wherein a first end of the first gear flat (756A) is rounded and inwardly turned so as to come to a singular point (760), a first end of the second gear flat (756B) is rounded and inwardly turned so as to come to the singular point (760), and wherein the singular point (760) contacts the rotatable shaft (604).

Clause 41: The roll subsystem (600) according to Clause 40, wherein a portion of the worm follower (610) between the first gear flat (756A) and the singular point (760) is separated from the rotatable shaft (604) by a first gap (761A), and wherein a portion of the worm follower (610) between the second gear flat (756B) and the singular point (760) is separated from the rotatable shaft (604) by a second gap (761B).

Clause 42: The roll subsystem (600) according to any one of Clauses 30 to 40, wherein the worm follower (610) comprises a first key (792), the rotatable shaft (604) comprises a first keyway (764), and first key (792) is configured to engage with the first keyway (764) to reduce backlash as the worm gear (608) actuates the worm follower (610).

Clause 43: The roll subsystem (600) according to any one of Clauses 30 to 41, wherein the worm follower (610) comprises a first key (792), the rotatable shaft (604) comprises a first keyway (764), and the first key (792)

is configured to engage with the first keyway (764) to reduce backlash as the worm gear (608) actuates the worm follower (610).

Clause 44: The roll subsystem (600) according to any one of Clauses 30 to 43, wherein: the worm follower (610) has a first portion with a first wall thickness (767A) and a second portion with a second wall thickness (767B), the first wall thickness (767A) being thicker than the second wall thickness (767B) thereby forming a gear step (766); the rotatable shaft (604) has a first portion with a first wall thickness (769A) and a second portion with a second wall thickness (769B), the first wall thickness (769A) being thicker than the second wall thickness (7679) thereby forming a shaft step (768); and the gear step (766) is configured to engage with the shaft step (768) to reduce backlash as the worm gear (608) actuates the worm follower (610).

Clause 45: The roll subsystem (600) according to any one of Clauses 30 to 44 further comprising a thrust block (712) positioned distal to the worm follower (610), the thrust block (712) engaging at least a portion of a housing (102).

Clause 46: The roll subsystem (600) according to Clause 45, wherein the thrust block (712) has a thickness of greater than 1.0 cm.

Clause 47: A transection subsystem (800) for a surgical instrument (100) comprising: a rotatable shaft (604) having a lumen (606); a firing rod (820) extending at least partially through the lumen (606); a firing rack (816) coupled to a proximal end of the firing rod (820), the firing rod (820) being rotationally independent of the firing rack (816); and a firing gear (814) engaged with the firing rack (816), wherein rotation of the firing gear (814) moves the firing rack (816) and the firing rod (820) axially.

Clause 48: The transection subsystem (800) according to Clause 47 further comprising a transection input puck (802) engageable with a first transection robotic output, wherein rotation of the firing gear (814) is dependent on rotation of the transection input puck (802).

Clause 49: The transection subsystem (800) according to Clause 48 further comprising: a transection drive shaft (804) coupled to the transection input puck (802); a transection spur gear (806) coupled to the transection drive shaft (804); a transection ramp gear (808) engaged with the transection spur gear (806); a ramp gear shaft (810) coupled to the transection ramp gear (808); and a speed gear (812) engaged with the ramp gear shaft (810).

Clause 50: The transection subsystem (800) according to any one of Clauses 47 to 49, wherein: the firing rack (816) defines a slot (824); the firing rod (820) comprises a T-shaped tab (822); and the T-shaped tab (822) is engaged with the slot (824) to enable rotation of the firing rod (820) with respect to the firing rack (816) while maintaining a longitudinal connection.

Clause 51: The transection subsystem of any one of Clauses 47 to 50 further comprising: a key receiver (830) in mechanical communication with the firing gear (814); and a key (836) configured to engage with the key receiver (830), wherein rotating the key (836) when engaged with the key receiver (830) causes the key receiver (830) and the firing gear (814) to rotate, thereby moving the firing rod (820) axially.

Clause 52: The transection subsystem of Clause 51, the key receiver (830) comprising one or more unidirectional ramps (831); and the key (836) comprising one or more corresponding unidirectional ramps configured to engage with the unidirectional ramps in a first direction and to slide along the unidirectional ramps in a second direction.

Clause 53: The transection subsystem of Clause 52, further comprising a spring (880) configured to permit the key receiver 830 to move away from the key (836) when the key (836) is rotated in the second direction.

Clause 54: The transection subsystem of any one of Clauses 51-53, the key (836) comprising one or more locking tabs (839) configured to attach the key (836) to the key receiver (830).

Clause 55: The transection subsystem of Clause 51, the key comprising threads (840) configured to engage with a housing (102) of the surgical instrument (100).

Clause 56: The transection subsystem of Clause 55, wherein, when the key (836) is turned in a first direction, the threads (840) cause the key (836) to move toward the key receiver (830) and, when the key (836) is turned in a second direction, the threads (840) cause the key (836) to move away from the key receiver (830).

Clause 57: The transection subsystem of any of Clauses 51-56 further comprising a tether (844) attached to the key (836) and a housing 102 of the medical device (100).

Clause 58: The transection subsystem of Clause 51, wherein the key (836) comprises a cam surface (850) and the key receiver (830) comprises a spline (852) configured to engage with the cam surface.

Clause 59: The transection subsystem of Clause 51, wherein the key (836) comprises a cam surface (850) and the key receiver (830) comprises a protrusion (892) configured to engage with the cam surface.

Clause 60: A method comprising: attaching a surgical instrument to a robotic arm; rotating a first input puck and a second input puck of the robotic arm until a predetermined threshold indicator on both the first input puck and the second input puck is detected, the first input puck and the second input puck being in mechanical communication with an articulation subsystem of the surgical instrument; and rotating the first input puck and the second input puck to a predetermined articulation home position.

Clause 61: The method of Clause 60 further comprising: rotating a third input puck until a second predetermined threshold indicator is detected, the third input puck being in mechanical communication with a closure subsystem of the surgical instrument; and rotating the third input puck until the closure subsystem is in a constant region of the closure subsystem.

Clause 62: The method of Clause 60 or 61 further comprising: rotating a fourth input puck until a third predetermined threshold indicator is detected, the fourth input puck being in mechanical communication with a transection subsystem of the surgical instrument; and rotating the fourth input puck to a predetermined transection home position.

Clause 63: The method of Clause 62 further comprising: rotating the third input puck to a predetermined closure home position.

Clause 64: The method of any one of Clauses 60-63 further comprising: rotating a fifth input puck until a fourth predetermined threshold indicator is detected, the fifth input puck being in mechanical communication with a roll subsystem of the surgical instrument; and rotating the fifth input puck to a predetermine roll home position.

Clause 65: A housing (102) for a surgical instrument (100) configured to engage with a robotic arm, the housing comprising: a first opening (1029) positioned to be engaged with at least a portion of a robotic arm; a second opening (1035) positioned proximate a rod (212, 604) extending from within the housing; and a fluid management system positioned within the housing (102) proximate one of the first opening (1029) or the second opening (1035), the fluid management system being configured to hold or divert fluid within the housing (102).

Clause 66: The housing (102) according to Clause 65, wherein the fluid management system comprises one or more walls (1004) forming a cavity (1002) within the housing (102) to hold or divert the fluid.

Clause 67: The housing (102) according to Clause 66, further comprising an absorbent (1006) positioned within the cavity (1002).

Clause 68: The housing (102) according to Clause 67, wherein the one or more walls (1004) comprises a retention feature (1008) configured to secure the absorbent (1006) within the cavity (1002).

Clause 69: The housing (102) according to Clause 68, wherein the retention feature (1008) is a rounded undercut positioned such that the absorbent (1006) rests between the retention feature (1008) and an interior surface (1100) of the housing (102).

Clause 70: The housing (102) according to Clause 68, wherein the retention feature (1008) is a one-way-ramp undercut positioned such that the absorbent (1006) rests between the retention feature (1008) and an interior surface (1100) of the housing (102).

Clause 71: The housing (102) according to Clause 68, wherein the retention feature (1008) is a barb positioned on an interior surface (1100) of the housing (102).

Clause 72: The housing (102) according to Clause 68, wherein the retention feature (1008) is a pin, and the absorbent (1006) comprises an aperture (1007) sized to accept the pin therethrough.

Clause 73: The housing (102) according to Clause 68, wherein the retention feature (1008) is a rivet positioned to attach the absorbent (1006) to an interior surface (1100) of the housing (102).

Clause 74: The housing (102) according to Clause 65, wherein the fluid management system comprises a fluid diverter (1030) positioned proximate the first opening (1029).

Clause 75: The housing (102) according to Clause 74, wherein the fluid management system further comprises one or more walls (1004) forming a cavity (1002) within the housing (102) to hold or divert the fluid, and wherein the fluid diverter (1030) comprises a channel (1032) configured to divert fluid into the cavity (1002).

Clause 76: The housing (102) according to Clause 75, further comprising an absorbent (1006) positioned within the cavity (1002).

Clause 77: The housing (102) according to any one of Clauses 74 to 76 further comprising a delatching body 1028 positioned within a delatch opening (1029) of the housing (102).

Clause 78: The housing (102) according to Clause 77, further comprising a release button (104) connected to the delatching body (1028) by a release hinge (1026), wherein the delatching body (1028) is configured to be actuated by the release button (104).

Clause 79: The housing (102) according to Clause 78, wherein the fluid diverter (1030) comprises an elastomeric material and is configured to stretch with the delatching body (1028).

Clause 80: The housing (102) according to any one of Clauses 65-79 further comprising a nose (1034) positioned proximate the rod (212, 604), wherein the fluid management system comprises a shaft bushing (1038) surrounding the rod (212, 604), and engaging with the nose (1034).

Clause 81: The housing (102) according to any one of Clauses 65-80 further comprising a nose (1034) positioned proximate the rod (212, 604), wherein the fluid management system comprises an absorbent ring positioned proximate the nose (1034).

Clause 82: The housing (102) according to any one of Clauses 65-81, wherein the surgical instrument (100) further comprises a knife insert retainer (838), wherein the rod (604) comprises a slot (824), the knife insert retainer (838) comprising an elastomeric seal extension (1044) extending into the slot (824).

Clause 83: The housing (102) according to any one of Clauses 65-82, wherein the fluid management system comprises a sleeve (1114) surrounding the rod (212, 604), the sleeve comprising an absorbent material.

Clause 84: The housing (102) according to Clause 83, wherein the sleeve (1114) is connected to the housing (102) by a sinching plate (1114).

Clause 85: The housing (102) according to any one of Clauses 65-84, wherein the fluid management system comprises a collar (1016, 1024) surrounding the rod (212, 604).

Clause 86: The housing (102) according to Clause 85, wherein the collar (1016) comprises a trap (1018) to pool fluid therein.

Clause 87: The housing (102) according to Clause 86, wherein the collar (1024) comprises a plurality of traps (1025) to pool fluid therein.

Clause 88: A surgical instrument (100) comprising: a housing (102); a closure subsystem (200) engaged with a shaft (604); an articulation subsystem (400) movable along the shaft (604) and independently of the closure subsystem (200); and a fluid management system positioned between the closure subsystem (200) and the articulation subsystem (400) and in contact with the shaft (604).

Clause 89: The surgical instrument (100) according to Clause 88, wherein the fluid management system comprises a sleeve (1114) surrounding the shaft (604), the sleeve (1114) comprising an absorbent material.

Clause 90: The surgical instrument (100) according to Clause 88, wherein the sleeve (1114) is connected to the housing (102) by a sinching plate (1114).

Clause 91: The surgical instrument (100) according to Clause 88 or Clause 89, wherein the fluid management system comprises a collar (1016, 1024) surrounding the shaft (604).

Clause 92: The surgical instrument (100) according to Clause 91, wherein the collar (1016) comprises a trap (1018) to pool fluid therein.

Clause 93: The surgical instrument (100) according to Clause 91, wherein the collar (1024) comprises a plurality of traps (1025) to pool fluid therein.

Clause 94: The surgical instrument (100) according to Clause 93, wherein the collar (1016) is attached at a first end to the closure subsystem (200) and at a second end to the articulation subsystem (400).

Clause 95: The surgical instrument (100) according to Clause 94, comprising the closure subsystem (200) of any one of Clauses 18 to 29 and the articulation subsystem (400) of any one of Clauses 1 to 17.

Clause 96: An articulation subsystem (400) for a surgical instrument (100) comprising: a rotatable shaft (604) having a longitudinal axis (474); an articulation rod (406) extending along the longitudinal axis (474) of the rotatable shaft (604) and rotationally coupled to the rotatable shaft (604); a first articulation bushing (426) slidable from a first position to a second position along the longitudinal axis (474) of the rotatable shaft (604), the first articulation bushing (426) being rotationally coupled to the rotatable shaft (604); a first rack (414) movable with respect to the longitudinal axis (474) of the rotatable shaft (604), the first rack (414) being rotationally independent of the rotatable shaft (604) and the first articulation bushing (426); and a first rack gear (434) engaged with the first rack (414), wherein rotation of the first rack gear (434) moves the first rack (414) with respect to the longitudinal axis (474), and wherein movement of the first rack (414) with respect to the longitudinal axis (474) imparts an axial force onto the first articulation bushing (426) moving the first articulation bushing (426) from the first position to the second position.

Clause 97: A closure subsystem comprising: a cam gear (210) comprising a cam track (214); and a yoke pin (216) coupled to a closure tube (212) and movable from a first position to a second position in response to a rotation of the cam gear (210), the yoke pin (216) extending into the cam track (214), wherein the cam track (214) is shaped to provide a non-linear movement profile of the yoke pin (216) and comprises an open position (272), a high speed compression region (274), a high force region (278), and a constant force region (282), wherein the high speed compression region (274), the high force region (278), and the constant force region (282) each have different curvatures, and wherein the constant force region (282) is shaped such that the yoke pin (216) remains stationary when tracking through the constant force region (282) as the cam gear (210) rotates.

Clause 98: A surgical instrument (100) comprising: the articulation subsystem (400) according to any one of Clauses 1 to 17 or 96; and the closure subsystem (200) according to any one of Clauses 18 to 29.

Clause 99: A surgical instrument (100) comprising: the closure subsystem (200) according to any one of Clauses 18 to 29; and the roll subsystem (600) according to any one of Clauses 30 to 46.

Clause 100: A surgical instrument (100) comprising: the closure subsystem (200) according to any one of Clauses 18 to 29; and the transection subsystem (800) according to any one of Clauses 47 to 58.

Clause 101: A surgical instrument (100) comprising: the articulation subsystem (400) according to any one of Clauses 1 to 17 or 96; and the roll subsystem (600) according to any one of Clauses 30 to 46.

Clause 102: A surgical instrument (100) comprising: the articulation subsystem (400) according to any one of Clauses 1 to 17 or 96; and the transection subsystem (800) according to any one of Clauses 47 to 58.

Clause 103: A surgical instrument (100) comprising: the roll subsystem (600) according to any one of Clauses 30 to 46; and the transection subsystem (800) according to any one of Clauses 47 to 58.

Clause 104: A surgical instrument (100) comprising: the closure subsystem (200) according to any one of Clauses 18 to 29; the articulation subsystem (400) according to any one of Clauses 1 to 17 or 96; the roll subsystem (600) according to any one of Clauses 30 to 46; and the transection subsystem (800) according to any one of Clauses 47 to 58.

Clause 105: A method of operating an articulation subsystem (400) of a surgical instrument (100), the method comprising: engaging an articulation input puck (402) with an articulation robotic output; and rotating the articulation robotic output to cause the articulation input puck (402) to rotate, wherein rotation of the articulation input puck (402) causes movement of an articulation bushing (426, 428, 429) between a distal position and a proximal position to actuate an articulation rod (406A, 407A, 406B, or 407B), and wherein actuation of the articulation rod (406A, 407A, 406B, or 407B) causes an end effector (150) to pivot about an articulation pivot point (466).

Clause 106: The method of Clause 105 further comprising rotating the articulation robotic output until a predetermined threshold indictor is detected.

Clause 107: The method of Clause 106 further comprising rotating the articulation robotic output to a predetermined home position, the predetermined home position being based at least in part on detecting the predetermined threshold indictor.

Clause 108: The method of Clause 106 or Clause 107, wherein the predetermined threshold indicator comprises a threshold force.

Clause 109: The method of Clause 106 or Clause 107, wherein the predetermined threshold indicator comprises a threshold current.

Clause 110: The method of Clause 106 or Clause 107, wherein the predetermined threshold indicator comprises a threshold voltage.

Clause 111: The method of any one of Clauses 105-110, wherein the articulation input puck (402) comprises a first articulation input puck (402), the articulation robotic output comprises a first articulation robotic output, and the articulation subsystem further comprises a second articulation input puck (404), the method further comprising: engaging the second articulation input puck (404) with a second articulation robotic output; and rotating both the first articulation robotic output and the second articulation robotic output to cause both the first articulation input puck (402) and the second articulation input puck (404) to rotate, wherein rotation of the first articulation input puck (402) and the second articulation input puck (404) together causes movement of an articulation bushing (426, 428, 429) between a distal position and a proximal position to actuate the articulation rod (406A, 407A, 406B, or 407B).

Clause 112: The method of Clause 111 further comprising rotating the first articulation input puck and the second articulation input puck until a predetermined threshold indicator on both the first input puck and the second input puck.

Clause 113: The method of Clause 112 further comprising rotating the first input puck and the second input puck to a predetermined articulation home position.

Clause 114: The method of any one of Clauses 105-113, wherein the articulation subsystem comprises: a rack (414A, 418A, 414B, 418B, or 414C) movable with respect to a longitudinal axis (474), the rack (414A, 418A, 414B, 418B, or 414C) being engaged with the articulation bushing (426, 426, 429); wherein rotation of the articulation input puck (402) causes movement of the rack (414A, 418A, 414B, 418B, or 414C), thereby moving the articulation bushing (426, 428, 429) between the proximal position and the distal position.

Clause 115: The method of Clause 114, wherein the articulation bushing (426, 428, 429) is rotationally independent of the rack (414A, 418A, 414B, 418B, or 414C).

Clause 116: The method of Clause 114 or Clause 115, wherein the articulation subsystem further comprises a rack gear (434) engaged with the rack (414A, 418A, 414B, 418B, or 414C), rotation of the rack gear (434) moving the rack (414A, 418A, 414B, 418B, or 414C) with respect to the longitudinal axis (474).

Clause 117: The method of Clause 116, wherein the articulation subsystem further comprises: an articulation drive shaft (432) extending from the articulation input puck (402) and comprising a drive gear (430); and a compound gear (442) engaged with the drive gear (430) and the rack gear (434), wherein rotation of the articulation input puck (402) rotates the rack gear (434) moving the rack (414A, 418A, 414B, 418B, or 414C) with respect to the longitudinal axis (474).

Clause 118: The method according to any one of Clauses 114 to 117, wherein the articulation bushing is a first articulation bushing (426), the rack is a first rack (414A, 414B), and the articulation rod is a first articulation rod (406A, 406B), the articulation subsystem further comprising: a second articulation bushing (428) slidable between a second proximal position and a second distal position along the longitudinal axis (474); and a second rack (418A, 418B) movable with respect to the longitudinal axis (474), wherein movement of the second rack (418A, 418B) with respect to the longitudinal axis (474) imparts an axial force onto the second articulation bushing (428) to move the second articulation bushing (428) between the second proximal position and the second distal position, wherein movement of the second articulation bushing (428) between the second distal position and the second proximal position actuates a second articulation rod (406) causing the end effector (150) to pivot about the articulation pivot point (466).

Clause 119: The method of Clause 118, wherein movement of the first articulation bushing (426) from the distal position to the proximal position actuates the end effector (150) in a first direction, and wherein movement of the second articulation bushing (428) from the second distal position to the second proximal position actuates the end effector (150) in a second direction.

The invention is not necessarily limited to the examples described, which can be varied in construction and detail. The terms "distal" and "proximal" are used throughout the preceding description and are meant to refer to a positions and directions relative to a treating physician. As such, "distal" or distally" refer to a position distant to or a direction away from the physician. Similarly, "proximal" or "proximally" refer to a position near or a direction towards the physician. Furthermore, the singular forms "a," "an," and "the" include plural referents unless the context clearly dictates otherwise. Furthermore, the use of "couple", "coupled", or similar phrases should not be construed as being limited to a certain number of components or a particular order of components unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

What is claimed is:

1. A method of operating an articulation subsystem of a surgical instrument, the method comprising:

engaging an articulation input puck with an articulation robotic output;

rotating the articulation robotic output to cause the articulation input puck to rotate; and rotating the articulation robotic output until a predetermined threshold indicator is detected, wherein rotation of the articulation input puck causes movement of an articulation bushing between a distal position and a proximal position to actuate an articulation rod, and wherein actuation of the articulation rod causes an end effector to pivot about an articulation pivot point.

2. The method of claim 1 further comprising rotating the articulation robotic output to a predetermined home position, the predetermined home position being based at least in part on detecting the predetermined threshold indicator.

3. The method of claim 1, wherein the predetermined threshold indicator comprises a threshold force.

4. The method of claim 1, wherein the predetermined threshold indicator comprises a threshold current.

5. The method of claim 1, wherein the predetermined threshold indicator comprises a threshold voltage.

6. The method of claim 1, wherein the articulation input puck comprises a first articulation input puck, the articulation robotic output comprises a first articulation robotic output, and the articulation subsystem further comprises a second articulation input puck, the method further comprising:

engaging the second articulation input puck with a second articulation robotic output; and rotating both the first articulation robotic output and the second articulation robotic output to cause both the first articulation input puck and the second articulation input puck to rotate, wherein rotation of the first articulation input puck and the second articulation input puck together causes movement of an articulation bushing between a distal position and a proximal position to actuate the articulation rod.

7. The method of claim 6 further comprising rotating the first articulation input puck and the second articulation input puck until the predetermined threshold indicator is detected.

8. The method of claim 7 further comprising rotating the first articulation input puck and the second articulation input puck to a predetermined articulation home position.

9. The method of claim 1, wherein the articulation subsystem comprises:

a rack movable with respect to a longitudinal axis, the rack being engaged with the articulation bushing;

wherein rotation of the articulation input puck causes movement of the rack, thereby moving the articulation bushing between the proximal position and the distal position.

10. The method of claim 9, wherein the articulation bushing is rotationally independent of the rack.

11. The method of claim 9, wherein the articulation subsystem further comprises a rack gear engaged with the rack, rotation of the rack gear moving the rack with respect to the longitudinal axis.

12. The method of claim 11, wherein the articulation subsystem further comprises:

an articulation drive shaft extending from the articulation input puck and comprising a drive gear; and a compound gear engaged with the drive gear and the rack gear, wherein rotation of the articulation input puck rotates the rack gear moving the rack with respect to the longitudinal axis.

13. The method of claim 9, wherein the articulation bushing is a first articulation bushing, the rack is a first rack, and the articulation rod is a first articulation rod, the articulation subsystem further comprising:

a second articulation bushing slidable between a second proximal position and a second distal position along the longitudinal axis; and a second rack movable with respect to the longitudinal axis, wherein movement of the second rack with respect to the longitudinal axis imparts an axial force onto the second articulation bushing to move the second articulation bushing between the second proximal position and the second distal position, wherein movement of the second articulation bushing between the second distal position and the second proximal position actuates a second articulation rod causing the end effector to pivot about the articulation pivot point.

14. The method of claim 13, wherein movement of the first articulation bushing from the distal position to the proximal position actuates the end effector in a first direction, and wherein movement of the second articulation bushing from the second distal position to the second proximal position actuates the end effector in a second direction.

15. A method comprising:

attaching a surgical instrument to a robotic arm;

rotating a first input puck and a second input puck of the robotic arm until a predetermined threshold indicator on both the first input puck and the second input puck is detected, the first input puck and the second input puck being in mechanical communication with an articulation subsystem of the surgical instrument; and rotating the first input puck and the second input puck to a predetermined articulation home position.

16. The method of claim 15 further comprising:

rotating a third input puck until a second predetermined threshold indicator is detected, the third input puck being in mechanical communication with a closure subsystem of the surgical instrument; and rotating the third input puck until the closure subsystem is in a constant region of the closure subsystem.

17. The method of claim 16 further comprising:

rotating a fourth input puck until a third predetermined threshold indicator is detected, the fourth input puck being in mechanical communication with a transection subsystem of the surgical instrument; and rotating the fourth input puck to a predetermined transection home position.

18. The method of claim 17 further comprising:

rotating the third input puck to a predetermined closure home position.

19. The method of claim 15 further comprising:

rotating a fifth input puck until a fourth predetermined threshold indicator is detected, the fifth input puck being in mechanical communication with a roll subsystem of the surgical instrument; and rotating the fifth input puck to a predetermine roll home position.

20. A method of operating an articulation subsystem of a surgical instrument, the method comprising:

engaging a first articulation input puck and with a first articulation robotic output;

engaging a second articulation input puck and with a second articulation robotic output; and rotating both the first articulation robotic output and the second articulation robotic output to cause both the first articulation input puck and the second articulation input puck to rotate, wherein the first articulation robotic output and the second articulation robotic output are rotated until a predetermined threshold indicator is detected, wherein rotation of the first articulation input puck and the second articulation input puck together causes movement of an articulation bushing between a distal position and a proximal position to actuate an articulation rod, and wherein actuation of the articulation rod causes an end effector to pivot about an articulation pivot point.

* * * * *